United States Patent
Crowe et al.

(10) Patent No.: US 11,684,677 B2
(45) Date of Patent: Jun. 27, 2023

(54) COMPOSITIONS

(71) Applicant: Sorriso Pharmaceuticals, Inc., San Diego, CA (US)

(72) Inventors: Scott Crowe, Cambridge (GB); Kevin Roberts, Cambridge (GB); Tim Carlton, Cambridge (GB); Luana Maggiore, Cambridge (GB); Marion Cubitt, Cambridge (GB); Mike West, Cambridge (GB); Keith Ray, Cambridge (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 240 days.

(21) Appl. No.: 16/366,454

(22) Filed: Mar. 27, 2019

(65) Prior Publication Data

US 2019/0307891 A1 Oct. 10, 2019

Related U.S. Application Data

(63) Continuation-in-part of application No. PCT/EP2017/074828, filed on Sep. 29, 2017.

(30) Foreign Application Priority Data

Sep. 30, 2016 (EP) ..................................... 16191988

(51) Int. Cl.
| | | |
|---|---|---|
| *A61P 1/00* | (2006.01) | |
| *A61K 9/00* | (2006.01) | |
| *C07K 16/24* | (2006.01) | |
| *C07K 16/28* | (2006.01) | |
| *A61K 39/00* | (2006.01) | |
| *A61K 47/68* | (2017.01) | |
| *A61K 47/65* | (2017.01) | |

(52) U.S. Cl.
CPC ........ *A61K 47/6849* (2017.08); *A61K 9/0053* (2013.01); *A61K 47/65* (2017.08); *A61K 47/6845* (2017.08); *A61P 1/00* (2018.01); *C07K 16/241* (2013.01); *C07K 16/2866* (2013.01); *A61K 2039/505* (2013.01); *A61K 2039/507* (2013.01); *A61K 2039/542* (2013.01); *C07K 2317/21* (2013.01); *C07K 2317/31* (2013.01); *C07K 2317/55* (2013.01); *C07K 2317/565* (2013.01); *C07K 2317/569* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 10,633,438 B2 * | 4/2020 | Crowe | .................... A61K 45/06 |
| 10,772,839 B2 * | 9/2020 | Crowe | .................... A61K 9/20 |
| 10,980,748 B2 * | 4/2021 | Crowe | .................... A61K 9/14 |
| 2006/0034833 A1 | 2/2006 | Beirnaert | |
| 2006/0034845 A1 | 2/2006 | Silence et al. | |
| 2007/0042399 A1 | 2/2007 | Wright et al. | |
| 2007/0077249 A1 | 4/2007 | Silence et al. | |
| 2007/0178082 A1 | 8/2007 | Silence et al. | |
| 2007/0237769 A1 | 10/2007 | Silence et al. | |
| 2010/0137213 A1 | 6/2010 | Fernandez et al. | |
| 2014/0186365 A1 | 7/2014 | Robinson et al. | |
| 2015/0337035 A1 | 11/2015 | Anderson et al. | |
| 2016/0264659 A1 | 9/2016 | Heavner et al. | |
| 2017/0022271 A1 | 1/2017 | Hoffman et al. | |
| 2018/0009881 A1 * | 1/2018 | Crowe | .................... A61P 37/00 |
| 2019/0092855 A1 * | 3/2019 | Crowe | .................... A61P 29/00 |

FOREIGN PATENT DOCUMENTS

| | | |
|---|---|---|
| WO | 9102078 A1 | 2/1991 |
| WO | 92/01047 A1 | 1/1992 |
| WO | 94/04678 A1 | 3/1994 |
| WO | 94/025591 A1 | 11/1994 |
| WO | 96/34103 A1 | 10/1996 |
| WO | 99/23221 A2 | 5/1999 |
| WO | 2002/012502 A2 | 2/2002 |
| WO | 02/48382 A2 | 6/2002 |
| WO | 2004/009776 A2 | 1/2004 |
| WO | 2004/037205 A2 | 5/2004 |
| WO | 2004/041862 A2 | 5/2004 |
| WO | 2004/041863 A2 | 5/2004 |
| WO | 2004/041865 A2 | 5/2004 |
| WO | 2004/041867 A2 | 5/2004 |
| WO | 2006/122786 A2 | 11/2006 |
| WO | 2006/122787 A1 | 11/2006 |
| WO | 2007/025977 A2 | 3/2007 |
| WO | 2007/048022 A2 | 4/2007 |
| WO | 2007/070948 A1 | 6/2007 |
| WO | 2007/104529 A2 | 9/2007 |
| WO | 2008/020079 A1 | 2/2008 |
| WO | 2008/049897 A1 | 5/2008 |

(Continued)

OTHER PUBLICATIONS

Bannas et al.,Front. Immunol., 8:1603. doi: 10.3389/fimmu.2017.01603 (2017).*
Kim, Youngkyun, et al.,"A Dual Target-directed Agent against Interleukin-6 Receptor and Tumor Necrosis Factror ameliorates experimental arthritis," Scientific Reports, 6:20150, pp. 1-12 (Feb. 4, 2016).
Yan, Junrong, et al., "Construction of a synthetic phage-displayed Nanobody library with CDR3 regions randomized by trinucleotide cassettes for diagnostic applications," Journal of Translational Medicine, 12:343, pp. 1-12 (2014).
Kamm, Michael A., et al., "Practical Application of Anti-TNF Therapy for Luminal Crohn's Disease," Inflammatory Bowel Diseases, vol. 17, No. 11, pp. 2366-2391 (Nov. 2011).

(Continued)

*Primary Examiner* — Marianne P Allen
(74) *Attorney, Agent, or Firm* — Wilson Sonsini Goodrich & Rosati

(57) ABSTRACT

There is provided inter alia a composition comprising a TNF-alpha binding polypeptide and an IL-6R binding polypeptide.

14 Claims, 14 Drawing Sheets

Specification includes a Sequence Listing.

(56) References Cited

FOREIGN PATENT DOCUMENTS

| WO | 2008/101985 A2 | 8/2008 |
| --- | --- | --- |
| WO | 2008/124170 A2 | 10/2008 |
| WO | 2008/144753 A2 | 11/2008 |
| WO | 2008/149143 A2 | 12/2008 |
| WO | 2009/021754 A2 | 2/2009 |
| WO | 2009/046168 A1 | 4/2009 |
| WO | 2010/020811 A1 | 2/2010 |
| WO | 2010/045506 A2 | 4/2010 |
| WO | 2010/056550 A1 | 5/2010 |
| WO | 2010/077422 A2 | 7/2010 |
| WO | 2010/115998 A2 | 10/2010 |
| WO | 2011/083175 A1 | 7/2011 |
| WO | 2011/135040 A1 | 11/2011 |
| WO | 2011/139629 A2 | 11/2011 |
| WO | 2012/007880 A2 | 1/2012 |
| WO | 2012/078878 A2 | 6/2012 |
| WO | 2012/131053 A1 | 10/2012 |
| WO | 2012/175741 A2 | 12/2012 |
| WO | 2013/024059 A2 | 2/2013 |
| WO | 2013/058833 A1 | 4/2013 |
| WO | 2013/064701 A2 | 5/2013 |
| WO | 2013/085893 A1 | 6/2013 |
| WO | 2014/064287 A1 | 5/2014 |
| WO | 2015/065987 A1 | 5/2015 |
| WO | 2015/144852 A1 | 10/2015 |
| WO | 2016/065323 A2 | 4/2016 |
| WO | 2016/103093 A1 | 6/2016 |
| WO | 2016/156468 A1 | 10/2016 |
| WO | 2016/162537 A1 | 10/2016 |
| WO | WO 2016/156465 * | 10/2016 |
| WO | 2016/202411 A1 | 12/2016 |
| WO | 2016/202414 A1 | 12/2016 |
| WO | 2016/202415 A1 | 12/2016 |
| WO | 2017/125578 A1 | 7/2017 |

OTHER PUBLICATIONS

Siontorou, Christina G, "Nanobodies as novel agents for disease diagnosis and therapy," International Journal of Nanomedicine, 8, pp. 4215-4227 (2013).

Baumgart, Daniel C, et al., "Crohn's disease," The Lancet 380, vol. 380, pp. 1590-1605 (Nov. 3, 2012).

Danese, Silvio, "New therapies for inflammatory bowel disease: from the bench to the bedside," Gut, vol. 61, No. 6, pp. 918-932 (Jun. 2012).

Shealy, David, et al., "Characterization of golimumab, a human monoclonal antibody specific for human tumor necrosis factor," mAbs, vol. 2, Issue 4, pp. 428-439 (Jul./Aug. 2010).

Van Deventer, S J H, "Anti-TNF antibody treatment of Crohn's disease," Ann Rheum Dis, 58:(Suppl I):I114-I120, (Nov. 1999).

Coppieters, Ken, et al., "Formatted Anti-Tumor Necrosis Factor & VHH Proteins Derived From Camelids Show Superior Potency and Targeting to Inflamed Joints in a Murine Model of Collagen-Induced Arthritis," Arthritis & Rheumatism, vol. 54, No. 6, pp. 1856-1866 (Jun. 2006).

Padlan, Eduardo A, "Anatomy of the Antibody Molecule," Molecular Immunology, vol. 31, No. 3, pp. 169-217, (1994).

Muyldermans, Serge, "Nanobodies: Natural Single-Domain Antibodies," Annual Review of Biochemistry, vol. 82, pp. 775-797 (2013).

Muyldermans, S., et al., "Sequence and structure of VH domain from naturally occurring camel heavy chain immunoglobulins lacking light chains," Protein Engineering, vol. 7, No. 9, pp. 1129-1135 (1994).

Hamers-Casterman, C, et al., "Naturally occuring antibodies devoid of light chains," Nature, vol. 363, pp. 446-448, (Jun. 3, 1993).

Ward, E. Sally, et al., "Binding activities of a repertoire of single immunoglobulin variable domains secreted from *Escherichia coli*," Nature, vol. 341, pp. 544-546 (Oct. 12, 1989).

Roux, Kenneth H. et al., "Structural analysis of the nurse shark (new) antigen receptor (NAR): Molecular convergence of the NAR and unusual mammalian immunoglobulins," Proc. Natl. Acad. Sci. USA, vol. 95 pp. 11804-11809, (Sep. 1998).

Griffiths, Katherine, et al., "Shark Variable New Antigen Receptor (VNar) Single Domain Antibody Fragments: Stability and Diagnostic Applications," Antibodies, 2, pp. 66-81, (2013).

Mccoy, Laura E., et al., "Neutralisation of HIV-1 cell-cell spread by human and llama antibodies," Retrovirology, 11:83, pp. 1-15 (2014).

Hendrickson, Barbara A., et al., "Clinical Aspects and Pathophysiology of Inflammatory Bowel Disease," Clinical Microbiology Reviews, vol. 15, No. 1, pp. 79-94 (2002).

Ortonne, J.-P, "Recent developments in the understanding of the pathogenesis of psoriasis," British Journal of Dermatology, 140 (Suppl. 54): pp. 1-7 (1999).

Kohler, G, et al., "Continuous cultures of fused cells secreting antibody of predefined specificity," Nature, vol. 256, pp. 495-497 (Aug. 7, 1975).

Nelson, P N, et al., "Monoclonal antibodies," J Clin Pathol: Mol Pathol, 53, pp. 111-117 (Feb. 8, 2000).

Chomczynski, Piotr, et al., "Single-Step Method of RNA Isolation by Acid Guanidinium Thiocyanate-Phenol-Chloroform Extraction," Analytical Biochemistry, 162, pp. 156-159 (1987).

Arbabi-Ghahroudi, M., et al., "Selection and Identification of single domain antibody fragments from camel heavy-chain antibodies," FEBS, Letters 414, pp. 521-526 (1997).

Tanha, Jamshid, et al. "Selection by phage display of llama conventional VH fragments with heavy chain antibody VHH properties," Journal of Immunological Methods, 263, pp. 97-109 (2002).

Harmsen, M.M., et al., "Properties, production, and applications of camelid single-doman antibody fragments," Appl Microbiol Biotechnol, 77, pp. 13-22 (2007).

Miethe, Sebastion, et al., "Production of Single Chain Fragment Variable (scFv) Antibodies in *Escherichia coli* Using the LEXTM Bioreactor," Journal of Biotechnology, 163, pp. 105-111 (2013).

Skerra, Arne et al., "Assembly of a Functional Immunoglobulin FV Fragment in *Escherichia coli*," Science, vol. 240 pp. 1038-1041 (1988).

Ling, Michael Mingfu, et al., "Approaches to DNA Mutagenesis: An Overview," Analytical Biochemistry, 254, Article No. AB972428, pp. 157-178 (1997).

Nambiar, KP, et al., "Total Synthesis and Cloning of a Gene Coding forthe Ribonuclease S Protein," Science, vol. 223, p. 1299-1301 (Mar. 23, 1984).

Sakmar, Thomas P., Total synthesis and expression of a gene for the subunit of bovine rod outer segment guanine nucleotide-binding protein (transducin), Nucleic Acids Research, vol. 16, No. 14, pp. 6361-6372 (1988).

Wells, James A., "Cassette mutagenesis: an efficient method for generation of multiple mutations at defined sites," Gene, Gene 1245, pp. 315-323 (1985).

Grundstrom, Thomas, et al., "Oligonnucleotide-directed mutagenesis by microscale 'shot-gun' gene synthesis," Nucleic Acids Research, vol. 13, No. 9, pp. 3305-3316 (1985).

Verma, Sandeep, et al., "Modified Oligonucleotides: Synthesis and Strategy for Users," Annual Review of Biochemistry, vol. 67, pp. 99-134 (1998).

Huse, William D., et al., "Generation of a Large Combinatorial Library of the Immunoglobulin Repertoire in Phage Lambda," Science, 246(4935) pp. 1275-1281 (Dec. 8, 1989).

Merchlinsky, Michael J., et al., "Construction of an Infectious Molecular Clone of the Autonomous Parvovirus Minute Virus of Mice," Journal of Virology, vol. 47, No. 1, pp. 227-232, (Jul. 1983).

Faisst, Steffen, et al., "Isolation of a Fully Infectious Variant of Parvovirus H-1 Supplanting the Standard Strain in Human Cells," Journal of Virology, vol. 69, No. 7, pp. 4538-4543 (Jul. 1995).

Frenken, Leon, G.J., et al.,"Isolation of antigen specific Llama VHH antibody fragments and their high level secretion by *Saccharomyces cerevisae*," Journal of Biotechnology, 78, pp. 11-21 (2000).

Hoogenboom, Hennie R., "Multi-subunit proteins on the surface of filamentous phage: methodologies for displaying antibody (Fab) heavy and light chains," Nucleic Acids Research, vol. 19, No. 15, pp. 4133-4137 (1991).

(56) References Cited

OTHER PUBLICATIONS

Harmsen, M.M., et al., "Effect of a pmr 1 disruption and different signal sequences on the intracellular processing and secretion of *Cyamopsis tetragonoloba* a-galactosidase by *Saccharomyces cerevisiae*," Gene ,125, pp. 115-123 (1993).
Blattler, Walter A., et al., "New Heterobifunctional Protein Cross-Linking Reagent That Forms an Acid-Labile Link," Biochemistry, vol. 24, No. 6, pp. 1517-1524 (1985).
Thomassen, Yvonne E., et al., "Large-scale production of $V_{HH}$ antibody fragments by *Saccharomyces cerevisiae*," Enzyme and Microbial Technology, 30, pp. 273-278 (2002).
Biancheri, P, et al., "P007. Differential cleavage of anti-tumor necrosis factor-alpha agents by matrix metalloproteinase (MMP)-10 and MMP-12 in inflammatory bowel disease," Presentation ECCO, Dublin Abstract, 1 page (2011).
Vandenbroucke, K, et al., "Orally administered L. *lactis* secreting an anti-TNF Nanobody demonstrate efficacy in chronic colitiS," Mucosal Immunology, vol. 3, No. 1, pp. 49-56 (Jan. 2010).
Ungar, Bella, et al., "Optimizing Anti-TNF-a Therapy: Serum Levels of Infliximab and Adalimumab Are Associated With Mucosal Healing in Patients With Inflammatory Bowel Diseases," Clinical Gastroenterology and Hepatology, vol. 14, No. 4, pp. 550-557 (2016).
Van Schie, K A, et al., "The antibody response against human and chimeric anti-TNF therapeutic antibodies primarily targets the TNF binding region," Ann Rheum Dis, 74, pp. 311-314 (2015).
Mølhøj, Michael, et al., "CD19-/CD3-bispecific antibody of the BiTE class is far superior to tandem diabody with respect to redirected tumor cell lysis," Molecular Immunology, 44, pp. 1935-1943 (2007).
Liu, Mengyuan, et al., "Targeting TNF-a with a tetravalent mini-antibody TNF-TeAb," Biochem. J. , pp. 237-246 (2007).
Hussack, Greg, et al., "Engineered Single-Domain Antibodies with High Protease Resistance and Thermal Stability," PLOS One, vol. 6, Issue 11, pp. 1-15 (Nov. 2011).
Harmsen, M.M., e al., "Selection and optimisation of proteolytically stable llama single-domain antibody fragments for oral immunotherapy," Applied Microbiology and Biotechnology, 72(3), pp. 544-551 (2006).
Rudikoff, Stuart, et al., "Single amino acid substitution altering antigen-binding specificity," Proc. Natl. Acad. Sci. USA, Immunology, vol. 79, pp. 1979-1983 (Mar. 1982).
Zabetakis, Dan, et al., "Contributions of the Complementarity Determining Regions to the Thermal Stability of a Single-Domain Antibody," PLOS One , vol. 8, Issue 10, pp. 1-7 (Oct. 2013).
Paul, William E., "Fundamental Immunology," Laboratory of Immunology National Institute of Allergy and Infectious Diseases National Institutes of Health , Third Edition, pp. 292-295 (1993).
Crowe, S., et al., "Gastrointestinal Stability and Tissue Penetration of V565: a Novel Orally Administered Anti-TNFa VorabodyTM," 10th Annual Proteins and Antibodies Congress, PEGS Europe, VHsquared (2017).
Crowe, S, et al., "Preclinical assessment of a novel anti-TNFa VorabodyTM as an oral therapy for Crohn's Disease," 18th International Congress of Mucosal Immunology, VHsquared (2017).
Crowe, J. Scott, et al., "Preclinical Development of a Novel, Orally-Administered Anti-Tumour Necrosis Factor Domain Antibody forthe Treatment of Inflammatory Bowel Disease," Scientific Reports, 8:4941 (2018).
Nurbhai, S., et al., "Measured and Modelled Data Suggest that Oral Administration of V565, A Novel Domain Antibody to TNF-alpha, Could be Beneficial in the Treatment of IBD," ECCO, VHsquared (2018).
Robinson, J, et al., "A Protease-resistant Oral Domain Antibody to TNFa Delivers High Concentrations of Active Compound in Ileal Fluid Subjects with an Ileostomy," 25th United European Gastroenterology Week, Barcelona, Spain, VHsquared (Oct. 28-Nov. 1, 2017).
Wahlich, John, et al., "Oral delivery of a novel domain antibody (VorabodyTM) for the treatment of Crohn's Disease," Global Conference on Pharmaceutics and Drug Delivery Systems, VHsquared (2017).
West, M., et al., "Predicting intestinal tract luminal concentrations after oral dosing of an anti TNFa domain antibody engineered for intestinal protease resistance," Antibody Engineering & Therapeutics, VHsquared (2017).
Gustot, T, et al., "Profile of soluble cytokine receptors in Crohn's disease," Gut, 54, pp. 488-495 (2005).
Hosokawa, Takehiko, et al., "Interleukin-6 and Soluble Interleukin-6 receptor in the colonic mucosa of inflammatory bowel disease," Journal of Gastroenterology and Hepatology, 14, pp. 987-996 (1999).
Ito, Hiroaki, et al., "A Pilot Randomized Trial of a Human Anti-Interleukin-6 Receptor Monoclonal Antibody in Active Crohn's Disease," Gastroenterology, vol. 126, No. 4, pp. 989-996 (2004).
Katoh, Kazutaka, et al., "MAFT Multiple Sequence Alignment Software Version 7: Improvements in Performance and Usability," Mol. Biol. Evol., 30(4), pp. 772-780 (2013).
Koh, Willie W.L., et al., "Generation of a Family-specific Phage Library of Llama Single Chain Antibody Fragments That Neutralize HIV-1*," The Journal of Biological Chemistry, vol. 285, No. 25, pp. 19116-19124 (Jun. 18, 2010).
Kusugami, Kazuo, et al., "Elevation of Interleukin-6 in Inflammatory Bowel Disease Is Macrophage- and Epithelial Cell-Dependent," Digestive Diseases and Sciences, vol. 40, No. 5, pp. 949-959 (May 1995).
Mitsuyama, Keiichi, et al., "Therapeutic Strategies for Targeting the IL-6/STAT3 Cytokine Signaling Pathway in Inflammatory Bowel Disease," Anticancer Research, 27, pp. 3749-3756 (2007).
Reimund, J.-M., et al., "Mucosal Inflammatory Cytokine Production by Intestinal Biopsies in Patients with Ulcerative Colitis and Crohn's Disease," Journal of Clinical Immunology, vol. 16, No. 3, pp. 144-150 (1996).
Reimund, J-M et al., "Increased production of tumour necrosis factor-a, interleukin-1b, and interleukin-6 by morphologically normal intestinal biopsies from patients with Crohn's disease," Gut, 39, pp. 684-689 (1996).
Reinecker, H.-C, et al., "Enhanced secretion of tumor necrosis factor-alpha, IL-6, and IL-1b by isolated lamina propria mononuclear cells from patients with ulcerative colitis and Crohn's disease," Clin Exp Immunol, 94, pp. 174-181 (1993).
Sakmar, Thomas P., "Total synthesis and expression of a gene forthe a-subunit of bovine rod outer segment guanine nucleotide-binding protein (transducin)," Nucleic Acids Research, vol. 16, No. 14, pp. 6361-6372 (1988).
Vossenkämper, Anna, et al., "A CD3-Specific Antibody Reduces the Cytokine Production and Alters Phosphoprotein Profiles in Intestinal Tissues From Patients With Inflammatory Bowel Disease," Gastroenterology , vol. 147, pp. 172-183 (Jul. 2014).
Waetzig, Georg H, et al., "Hitting a complex target: an update on interleukin-6 trans-signalling," Expert Opin. Ther. Targets, 16(2), pp. 225-236 (2012).
Achstetter, Tilman, et al., "A new signal peptide useful for secretion of heterologous proteins from yeast and its application for synthesis of hirudin," Gene , 110, pp. 25-31 (1992).
Binz, H. Kaspar, et al., "Designing Repeat Proteins: Well-expressed, Soluble and Stable Proteins from Combinatorial Libraries of Consensus Ankyrin Repeat Proteins," Journal of Mollecular Biology, 332, pp. 489-503 (2003).
Desmet, Johan, et al., "Structural basis of IL-23 antagonism by an Alphabody protein scaffold," Nature Communications, 5:5237, (Oct. 30, 2014).
Ebersbach, Hilmar, et al., "Affilin-Novel Binding Molecules Based on Human g-B-Crystallin, an All b-Sheet Protein," Journal of Molecular Biology, 372, pp. 172-185, (2007).
Goldberg, Shalom D, "Engineering a targeted delivery platform using Centyrins," Protein Engineering, Design & Selection, vol. 29, No. 12, pp. 563-572 (2016).

(56) References Cited

OTHER PUBLICATIONS

Grabulovski, Dragan, et al., "A Novel, Non-immunogenic Fyn SH3-derived Binding Protein with Tumor Vascular Targeting Properties," The Journal of Biological Chemistry, vol. 282, No. 5, pp. 3196-3204 (Feb. 2, 2007).

Humphreys, David T., et al., "Modes of L929 Cell Death Induced By TNF-a And Other Cytotoxic Agents," Cytokine, vol. 11, No. 11, pp. 773-782 (Oct. 1999).

Johnson, Anthony, et al., "Sensitive Affimer and Antibody Based Impedimetric Label-Free Assays for C-Reactive Protein," Analytical Chemistry, 84, pp. 6553-6560 (Jul. 10, 2012).

Knezevic, Jelena, et al., "Quantitation of Affinity, Avidity, and Binding Kinetics of Protein Analytes with a Dynamically Switchable Biosurface," Journal of the American Chemical Society, 134, pp. 15225-15228 (Sep. 4, 2012).

Koide, Akiko, et al., "Antibody Mimics Based on the Scaffold of the Fibronectin Type III Domain," Methods in Molecular Biology, vol. 352: Protein Engineering Protocols, pp. 95-111.

Krehenbrink, Martin, et al., "Artificial Binding Proteins (Affitins) as Probes for Conformational Changes in Secretin PulD," . Mol. Biol., 383, pp. 1058-1068 (2008).

Lipovsek, D, "Adnectins: engineered target-binding protein therapeutics," Protein Engineering, Design & Selection , vol. 24 No. 1-2 pp. 3-9 (2011).

Lopes, Teresa S., et al., "High-copy-number integration into the ribosomal DNA of *Saccharomyces cerevisiae*: a new vector for high-level expression," Gene, 79, pp. 199-206 (1989).

Romanos, Michael A., et al., "Foreign Gene Expression in Yeast: a Review," Yeast, vol. 8 pp. 423-488 (1992).

Silverman, Joshua, et al., "Multivalent avimer proteins evolved by exon shuffling of a family of human receptor domains," nature biotechnology , vol. 23, No. 12, pp. 1556-1561 (Dec. 2005).

Skerra, Arne, "Alternative binding proteins: Anticalins—harnessing the structural plasticity of the lipocalin ligand pocket to engineer novel binding activities," FEBS, Journal 275, pp. 2677-2683 (2008).

Suderman, Richard J., et al., "Development of polyol-responsive antibody mimetics for single-step protein purification," Protein Expression and Purification , vol. 134, pp. 114-124 (2017).

Crowe, S., et al., "Oral delivery of a novel engineered anti-TNFa domain antibody (VorabodyTM) for the treatment of Intestinal Bowel Disease," PEGS Europe, VHsquared (2017).

PCT/EP2017/074828 International Search Report and Written Opinion dated Nov. 30, 2017.

\* cited by examiner

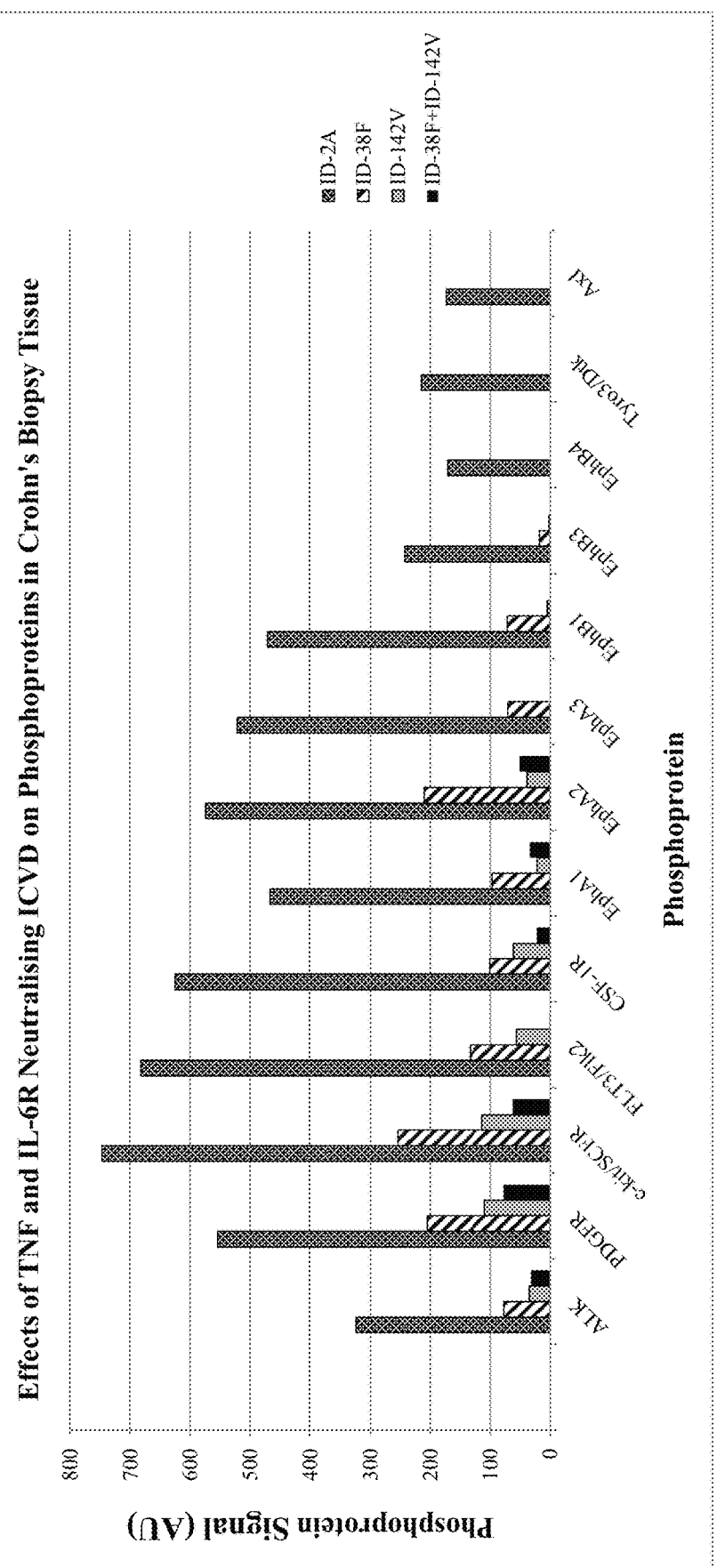

Figure 3

Inhibition of Phosphoproteins in Crohn's Biopsy Tissue by TNF and IL-6R Neutralising ICVD

SEQUENCE LISTING

<160> NUMBER OF SEQ ID NOS: 37

<210> SEQ ID NO 1
<211> LENGTH: 5
<212> TYPE: PRT
<213> ORGANISM: Artificial Sequence
<220> FEATURE:
<223> OTHER INFORMATION: Polypeptide sequence of CDR1 of ID-38F

<400> SEQUENCE: 1

Ser His Trp Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Polypeptide sequence of CDR2 of ID-38F

<400> SEQUENCE: 2

Glu Ile Asn Thr Asn Gly Leu Ile Thr His Tyr Gly Asp Ser Val Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: Polypeptide sequence of CDR3 of ID-38F

<400> SEQUENCE: 3

Asn Gln His Gly Leu Asn
1               5

<210> SEQ ID NO 4
<211> LENGTH: 30
<212> TYPE: PRT
<213> ORGANISM: Artificial Sequence
<220> FEATURE:
<223> OTHER INFORMATION: Polypeptide sequence of FR1 of ID-38F

<400> SEQUENCE: 4

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser
            20                  25                  30

<210> SEQ ID NO 5
<211> LENGTH: 14
<212> TYPE: PRT

```
<213> ORGANISM: Artificial Sequence
<220> FEATURE:
<223> OTHER INFORMATION: Polypeptide sequence of FR2 of ID-38F

<400> SEQUENCE: 5

Trp Val Arg Gln Ala Pro Gly Lys Glu Leu Glu Trp Leu Ser
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Polypeptide sequence of FR3 of ID-38F

<400> SEQUENCE: 6

Arg Phe Thr Val Ser Arg Asn Asn Ala Ala Asn Lys Met Tyr Leu Glu
1               5                   10                  15

Leu Thr Arg Leu Glu Pro Glu Asp Thr Ala Leu Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Polypeptide sequence of FR4 of ID-38F

<400> SEQUENCE: 7

Lys Gly Gln Gly Thr Gln Val Thr Val Ser Ser
1               5                   10

<210> SEQ ID NO 8
<211> LENGTH: 115
<212> TYPE: PRT
<213> ORGANISM: Artificial Sequence
<220> FEATURE:
<223> OTHER INFORMATION: Polypeptide sequence of ID-38F

<400> SEQUENCE: 8

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
                100                 105                 110

Val Ser Ser
        115

<210> SEQ ID NO 9
<211> LENGTH: 5
<212> TYPE: PRT
<213> ORGANISM: Artificial Sequence
<220> FEATURE:
<223> OTHER INFORMATION: Polypeptide sequence of CDR1 of ID-142V
```

<400> SEQUENCE: 9

Ile Asn Val Met Ala
1               5

<210> SEQ ID NO 10
<211> LENGTH: 16
<212> TYPE: PRT
<213> ORGANISM: Artificial Sequence
<220> FEATURE:
<223> OTHER INFORMATION: Polypeptide sequence of CDR2 of ID-142V

<400> SEQUENCE: 10

Ile Ile Gly Lys Gly Gly Gly Thr Asn Tyr Ala Asp Phe Val Lys Gly
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Polypeptide sequence of CDR3 of ID-142V

<400> SEQUENCE: 11

Asp Tyr Glu Asp His Asp Ser Pro His Asn Ala Ser
1               5                   10

<210> SEQ ID NO 12
<211> LENGTH: 33
<212> TYPE: PRT
<213> ORGANISM: Artificial Sequence
<220> FEATURE:
<223> OTHER INFORMATION: Polypeptide sequence of FR1 of ID-142V

<400> SEQUENCE: 12

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser

<210> SEQ ID NO 13
<211> LENGTH: 14
<212> TYPE: PRT
<213> ORGANISM: Artificial Sequence
<220> FEATURE:
<223> OTHER INFORMATION: Polypeptide sequence of FR2 of ID-142V

<400> SEQUENCE: 13

Trp Tyr Arg Gln Ala Pro Gly Lys Gly Arg Glu Leu Val Ala
1               5                   10

<210> SEQ ID NO 14
<211> LENGTH: 32
<212> TYPE: PRT
<213> ORGANISM: Artificial Sequence
<220> FEATURE:
<223> OTHER INFORMATION: Polypeptide sequence of FR3 of ID-142V

<400> SEQUENCE: 14

Arg Phe Thr Ile Ser Arg Asp Ala Ala Lys Asn Thr Val Tyr Leu Gln
1               5                   10                  15

Met Asn Ser Leu Arg Pro Glu Asp Thr Ala Val Tyr Tyr Cys Tyr Ala
            20                  25                  30

<210> SEQ ID NO 15
<211> LENGTH: 11
<212> TYPE: PRT
<213> ORGANISM: Artificial Sequence
<220> FEATURE:
<223> OTHER INFORMATION: Polypeptide sequence of FR4 of ID-142V

<400> SEQUENCE: 15

Trp Gly Gln Gly Thr Gln Val Thr Val Ser Ser
1               5                   10

<210> SEQ ID NO 16
<211> LENGTH: 123
<212> TYPE: PRT
<213> ORGANISM: Artificial Sequence
<220> FEATURE:
<223> OTHER INFORMATION: Polypeptide sequence of ID-142V

<400> SEQUENCE: 16

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
                20                  25                  30

Ser Ile Asn Val Met Ala Trp Tyr Arg Gln Ala Pro Gly Lys Gly Arg
            35                  40                  45

Glu Leu Val Ala Ile Ile Gly Lys Gly Gly Thr Asn Tyr Ala Asp
        50                  55                  60

Phe Val Lys Gly Arg Phe Thr Ile Ser Arg Asp Ala Ala Lys Asn Thr
65                  70                  75                  80

Val Tyr Leu Gln Met Asn Ser Leu Arg Pro Glu Asp Thr Ala Val Tyr
                85                  90                  95

Tyr Cys Tyr Ala Asp Tyr Glu Asp His Asp Ser Pro His Asn Ala Ser
            100                 105                 110

Trp Gly Gln Gly Thr Gln Val Thr Val Ser Ser
        115                 120

<210> SEQ ID NO 17
<211> LENGTH: 745
<212> TYPE: DNA
<213> ORGANISM: Artificial Sequence
<220> FEATURE:
<223> OTHER INFORMATION: Polynucleotide sequence encoding ID-38F

<400> SEQUENCE: 17
cgaattggcg gaaggccgtc aaggccacgt gtcttgtcca ggcgcgccag agctcatcac        60
acaaacaaac aaaacaaaat gatgagattt ccttcaattt ttactgccgt tttattcgca       120
gcatcctccg cattagctgc tccagtcaac actacaacag aagatgaaac ggcacaaatt       180
ccggctgaag ctgtcatcgg ttactcagat ttagaagggg atttcgatgt tgctgttttg       240
ccattttcca acagcacaaa taacgggtta ttgtttataa atactactat tgccagcatt       300
gctgctaaag aagaaggggt atctctcgag aaaagagatg ttcaattggt tgaatctggt       360
ggtggtttgg ttcaaccagg tggttctttg aaattgtctt gtgctgcttc tggtttcgat       420
ttctcttctc attggatgta ctgggttaga caagctccag gtaaagaatt ggaatggttg       480
tctgaaatca acaccaacgg tttgattacc cattatggtg attctgtcaa gggtagattc       540
actgtctcta gaaacaatgc tgctaacaag atgtacttgg aattgaccag attggaacca       600
gaagatactg ccttgtatta ctgcgctaga atcaacatg gttgaacaa aggtcaaggt       660

```
actcaagtta ccgtttcctc ataatgactt aagcttatta attaatggag cacaagactg    720
gcctcatggg ccttccgctc actgc                                          745
```

<210> SEQ ID NO 18
<211> LENGTH: 684
<212> TYPE: DNA
<213> ORGANISM: Artificial Sequence
<220> FEATURE:
<223> OTHER INFORMATION: Polynucleotide sequence encoding ID-142V

<400> SEQUENCE: 18

```
catcatatcg agctcatcac acaaacaaac aaaacaaaat gatgagattt ccttcaattt     60
ttactgccgt tttattcgca gcatcctccg cattagctgc tccagtcaac actacaacag    120
aagatgaaac ggcacaaatt ccggctgaag ctgtcatcgg ttactcagat ttagaagggg    180
atttcgatgt tgctgttttg ccattttcca acagcacaaa taacgggtta ttgtttataa    240
atactactat tgccagcatt gctgctaaag aagaaggggt atctctcgag aaaagagatg    300
tgcagctggt ggagtctggg ggaggtttgg tgcaggctgg ggggtcaacg agactcacct    360
gtaaagcctc tggaagtatc agcaatatca acagtatcaa cgtcatggca tggtaccgcc    420
aggctccagg gaagggtcgc gaattggtcg caattattgg taaaggtggt gggacaaact    480
acgcagactt cgtgaagggc cgattcacca tttccagaga tgctgccaag aacacggtat    540
atctgcaaat gaacagcttg agacctgagg acacggccgt ctattactgt tatgcggatt    600
atgaagatca cgattccccg cataacgctt cctggggcca ggggacccag gtcaccgtct    660
cctcatagta agcttcccat gatg                                           684
```

<210> SEQ ID NO 19
<211> LENGTH: 335
<212> TYPE: PRT
<213> ORGANISM: Artificial Sequence
<220> FEATURE:
<223> OTHER INFORMATION: Polypeptide sequence of ID-9K including export
      signal sequence

<400> SEQUENCE: 19

```
Met Met Arg Phe Pro Ser Ile Phe Thr Ala Val Leu Phe Ala Ala Ser
1               5                   10                  15

Ser Ala Leu Ala Ala Pro Val Asn Thr Thr Thr Glu Asp Glu Thr Ala
            20                  25                  30

Gln Ile Pro Ala Glu Ala Val Ile Gly Tyr Ser Asp Leu Glu Gly Asp
        35                  40                  45

Phe Asp Val Ala Val Leu Pro Phe Ser Asn Ser Thr Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Glu Lys Arg Asp Val Gln Leu Val Glu Ser Gly Gly Gly
                85                  90                  95

Leu Val Gln Pro Gly Gly Ser Leu Lys Leu Ser Cys Ala Ala Ser Gly
            100                 105                 110

Phe Asp Phe Ser Ser His Trp Met Tyr Trp Val Arg Gln Ala Pro Gly
        115                 120                 125

Lys Glu Leu Glu Trp Leu Ser Glu Ile Asn Thr Asn Gly Leu Ile Thr
    130                 135                 140

His Tyr Gly Asp Ser Val Lys Gly Arg Phe Thr Val Ser Arg Asn Asn
145                 150                 155                 160
```

```
Ala Ala Asn Lys Met Tyr Leu Glu Leu Thr Arg Leu Glu Pro Glu Asp
                165                 170                 175

Thr Ala Leu Tyr Tyr Cys Ala Arg Asn Gln His Gly Leu Asn Lys Gly
            180                 185                 190

Gln Gly Thr Gln Val Thr Val Ser Ser Gly Gly Gly Ser Lys Gly
        195                 200                 205

Gly Gly Gly Ser Asp Val Gln Leu Val Glu Ser Gly Gly Gly Leu Val
    210                 215                 220

Gln Ala Gly Gly Ser Thr Arg Leu Thr Cys Lys Ala Ser Gly Ser Ile
225                 230                 235                 240

Ser Asn Ile Asn Ser Ile Asn Val Met Ala Trp Tyr Arg Gln Ala Pro
            245                 250                 255

Gly Lys Gly Arg Glu Leu Val Ala Ile Ile Gly Lys Gly Gly Thr
        260                 265                 270

Asn Tyr Ala Asp Phe Val Lys Gly Arg Phe Thr Ile Ser Arg Asp Ala
    275                 280                 285

Ala Lys Asn Thr Val Tyr Leu Gln Met Asn Ser Leu Arg Pro Glu Asp
    290                 295                 300

Thr Ala Val Tyr Tyr Cys Tyr Ala Asp Tyr Glu Asp His Asp Ser Pro
305                 310                 315                 320

His Asn Ala Ser Trp Gly Gln Gly Thr Gln Val Thr Val Ser Ser
            325                 330                 335

<210> SEQ ID NO 20
<211> LENGTH: 335
<212> TYPE: PRT
<213> ORGANISM: Artificial Sequence
<220> FEATURE:
<223> OTHER INFORMATION: Polypeptide sequence of ID-10K including export
      signal sequence

<400> SEQUENCE: 20

Met Met Arg Phe Pro Ser Ile Phe Thr Ala Val Leu Phe Ala Ala Ser
1               5                   10                  15

Ser Ala Leu Ala Ala Pro Val Asn Thr Thr Thr Glu Asp Glu Thr Ala
            20                  25                  30

Gln Ile Pro Ala Glu Ala Val Ile Gly Tyr Ser Asp Leu Glu Gly Asp
        35                  40                  45

Phe Asp Val Ala Val Leu Pro Phe Ser Asn Ser Thr Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Glu Lys Arg Asp Val Gln Leu Val Glu Ser Gly Gly Gly
                85                  90                  95

Leu Val Gln Ala Gly Gly Ser Thr Arg Leu Thr Cys Lys Ala Ser Gly
            100                 105                 110

Ser Ile Ser Asn Ile Asn Ser Ile Asn Val Met Ala Trp Tyr Arg Gln
        115                 120                 125

Ala Pro Gly Lys Gly Arg Glu Leu Val Ala Ile Ile Gly Lys Gly Gly
    130                 135                 140

Gly Thr Asn Tyr Ala Asp Phe Val Lys Gly Arg Phe Thr Ile Ser Arg
145                 150                 155                 160

Asp Ala Ala Lys Asn Thr Val Tyr Leu Gln Met Asn Ser Leu Arg Pro
                165                 170                 175

Glu Asp Thr Ala Val Tyr Tyr Cys Tyr Ala Asp Tyr Glu Asp His Asp
            180                 185                 190
```

-continued

```
Ser Pro His Asn Ala Ser Trp Gly Gln Gly Thr Gln Val Thr Val Ser
        195                 200                 205

Ser Gly Gly Gly Ser Lys Gly Gly Gly Ser Asp Val Gln Leu
210                 215                 220

Val Glu Ser Gly Gly Leu Val Gln Pro Gly Gly Ser Leu Lys Leu
225                 230                 235                 240

Ser Cys Ala Ala Ser Gly Phe Asp Phe Ser Ser His Trp Met Tyr Trp
                245                 250                 255

Val Arg Gln Ala Pro Gly Lys Glu Leu Glu Trp Leu Ser Glu Ile Asn
                260                 265                 270

Thr Asn Gly Leu Ile Thr His Tyr Gly Asp Ser Val Lys Gly Arg Phe
                275                 280                 285

Thr Val Ser Arg Asn Asn Ala Ala Asn Lys Met Tyr Leu Glu Leu Thr
            290                 295                 300

Arg Leu Glu Pro Glu Asp Thr Ala Leu Tyr Tyr Cys Ala Arg Asn Gln
305                 310                 315                 320

His Gly Leu Asn Lys Gly Gln Gly Thr Gln Val Thr Val Ser Ser
                325                 330                 335

<210> SEQ ID NO 21
<211> LENGTH: 354
<212> TYPE: PRT
<213> ORGANISM: Artificial Sequence
<220> FEATURE:
<223> OTHER INFORMATION: Polypeptide sequence of ID-11K including export
      signal sequence

<400> SEQUENCE: 21

Met Met Arg Phe Pro Ser Ile Phe Thr Ala Val Leu Phe Ala Ala Ser
1               5                   10                  15

Ser Ala Leu Ala Ala Pro Val Asn Thr Thr Thr Glu Asp Glu Thr Ala
                20                  25                  30

Gln Ile Pro Ala Glu Ala Val Ile Gly Tyr Ser Asp Leu Glu Gly Asp
            35                  40                  45

Phe Asp Val Ala Val Leu Pro Phe Ser Asn Ser Thr Asn Asn Gly Leu
50                  55                  60

Leu Phe Ile Asn Thr Thr Ile Ala Ser Ile Ala Ala Lys Glu Glu Gly
65                  70                  75                  80

Val Ser Leu Glu Lys Arg Asp Val Gln Leu Val Glu Ser Gly Gly Gly
                85                  90                  95

Leu Val Gln Pro Gly Gly Ser Leu Lys Leu Ser Cys Ala Ala Ser Gly
            100                 105                 110

Phe Asp Phe Ser Ser His Trp Met Tyr Trp Val Arg Gln Ala Pro Gly
        115                 120                 125

Lys Glu Leu Glu Trp Leu Ser Glu Ile Asn Thr Asn Gly Leu Ile Thr
130                 135                 140

His Tyr Gly Asp Ser Val Lys Gly Arg Phe Thr Val Ser Arg Asn Asn
145                 150                 155                 160

Ala Ala Asn Lys Met Tyr Leu Glu Leu Thr Arg Leu Glu Pro Glu Asp
                165                 170                 175

Thr Ala Leu Tyr Tyr Cys Ala Arg Asn Gln His Gly Leu Asn Lys Gly
            180                 185                 190

Gln Gly Thr Gln Val Thr Val Ser Ser Gly Gly Gly Ser Gly Gly
        195                 200                 205

Gly Gly Ser Gly Gly Gly Gly Ser Gly Gly Gly Ser Gly Gly Gly
```

```
                     210                 215                 220
Gly Ser Gly Gly Gly Ser Asp Val Gln Leu Val Glu Ser Gly Gly
225                 230                 235                 240

Gly Leu Val Gln Ala Gly Gly Ser Thr Arg Leu Thr Cys Lys Ala Ser
                245                 250                 255

Gly Ser Ile Ser Asn Ile Asn Ser Ile Asn Val Met Ala Trp Tyr Arg
            260                 265                 270

Gln Ala Pro Gly Lys Gly Arg Glu Leu Val Ala Ile Ile Gly Lys Gly
        275                 280                 285

Gly Gly Thr Asn Tyr Ala Asp Phe Val Lys Gly Arg Phe Thr Ile Ser
    290                 295                 300

Arg Asp Ala Ala Lys Asn Thr Val Tyr Leu Gln Met Asn Ser Leu Arg
305                 310                 315                 320

Pro Glu Asp Thr Ala Val Tyr Tyr Cys Tyr Ala Asp Tyr Glu Asp His
                325                 330                 335

Asp Ser Pro His Asn Ala Ser Trp Gly Gln Gly Thr Gln Val Thr Val
            340                 345                 350

Ser Ser

<210> SEQ ID NO 22
<211> LENGTH: 354
<212> TYPE: PRT
<213> ORGANISM: Artificial Sequence
<220> FEATURE:
<223> OTHER INFORMATION: Polypeptide sequence of ID-12K including export
      signal sequence

<400> SEQUENCE: 22

Met Met Arg Phe Pro Ser Ile Phe Thr Ala Val Leu Phe Ala Ala Ser
1               5                   10                  15

Ser Ala Leu Ala Ala Pro Val Asn Thr Thr Thr Glu Asp Glu Thr Ala
                20                  25                  30

Gln Ile Pro Ala Glu Ala Val Ile Gly Tyr Ser Asp Leu Glu Gly Asp
            35                  40                  45

Phe Asp Val Ala Val Leu Pro Phe Ser Asn Ser Thr Asn Asn Gly Leu
50                  55                  60

Leu Phe Ile Asn Thr Thr Ile Ala Ser Ile Ala Ala Lys Glu Glu Gly
65                  70                  75                  80

Val Ser Leu Glu Lys Arg Asp Val Gln Leu Val Glu Ser Gly Gly Gly
                85                  90                  95

Leu Val Gln Ala Gly Gly Ser Thr Arg Leu Thr Cys Lys Ala Ser Gly
            100                 105                 110

Ser Ile Ser Asn Ile Asn Ser Ile Asn Val Met Ala Trp Tyr Arg Gln
        115                 120                 125

Ala Pro Gly Lys Gly Arg Glu Leu Val Ala Ile Ile Gly Lys Gly Gly
    130                 135                 140

Gly Thr Asn Tyr Ala Asp Phe Val Lys Gly Arg Phe Thr Ile Ser Arg
145                 150                 155                 160

Asp Ala Ala Lys Asn Thr Val Tyr Leu Gln Met Asn Ser Leu Arg Pro
                165                 170                 175

Glu Asp Thr Ala Val Tyr Tyr Cys Tyr Ala Asp Tyr Glu Asp His Asp
            180                 185                 190

Ser Pro His Asn Ala Ser Trp Gly Gln Gly Thr Gln Val Thr Val Ser
        195                 200                 205

Ser Gly Gly Gly Gly Ser Gly Gly Gly Gly Ser Gly Gly Gly Gly Ser
```

```
            210                 215                 220
Gly Gly Gly Gly Ser Gly Gly Gly Ser Gly Gly Gly Ser Asp
225                 230                 235                 240

Val Gln Leu Val Glu Ser Gly Gly Leu Val Gln Pro Gly Gly Ser
                    245                 250                 255

Leu Lys Leu Ser Cys Ala Ala Ser Gly Phe Asp Phe Ser His Trp
                260                 265                 270

Met Tyr Trp Val Arg Gln Ala Pro Gly Lys Glu Leu Glu Trp Leu Ser
            275                 280                 285

Glu Ile Asn Thr Asn Gly Leu Ile Thr His Tyr Gly Asp Ser Val Lys
        290                 295                 300

Gly Arg Phe Thr Val Ser Arg Asn Asn Ala Ala Asn Lys Met Tyr Leu
305                 310                 315                 320

Glu Leu Thr Arg Leu Glu Pro Glu Asp Thr Ala Leu Tyr Tyr Cys Ala
                325                 330                 335

Arg Asn Gln His Gly Leu Asn Lys Gly Gln Gly Thr Gln Val Thr Val
                340                 345                 350

Ser Ser

<210> SEQ ID NO 23
<211> LENGTH: 334
<212> TYPE: PRT
<213> ORGANISM: Artificial Sequence
<220> FEATURE:
<223> OTHER INFORMATION: Polypeptide sequence of ID-13K including export
      signal sequence

<400> SEQUENCE: 23

Met Met Arg Phe Pro Ser Ile Phe Thr Ala Val Leu Phe Ala Ala Ser
1               5                   10                  15

Ser Ala Leu Ala Ala Pro Val Asn Thr Thr Glu Asp Glu Thr Ala
            20                  25                  30

Gln Ile Pro Ala Glu Ala Val Ile Gly Tyr Ser Asp Leu Glu Gly Asp
        35                  40                  45

Phe Asp Val Ala Val Leu Pro Phe Ser Asn Ser Thr Asn Asn Gly Leu
50                  55                  60

Leu Phe Ile Asn Thr Thr Ile Ala Ser Ile Ala Ala Lys Glu Glu Gly
65                  70                  75                  80

Val Ser Leu Glu Lys Arg Asp Val Gln Leu Val Glu Ser Gly Gly Gly
                85                  90                  95

Leu Val Gln Pro Gly Gly Ser Leu Lys Leu Ser Cys Ala Ala Ser Gly
                100                 105                 110

Phe Asp Phe Ser Ser His Trp Met Tyr Trp Val Arg Gln Ala Pro Gly
            115                 120                 125

Lys Glu Leu Glu Trp Leu Ser Glu Ile Asn Thr Asn Gly Leu Ile Thr
        130                 135                 140

His Tyr Gly Asp Ser Val Lys Gly Arg Phe Thr Val Ser Arg Asn Asn
145                 150                 155                 160

Ala Ala Asn Lys Met Tyr Leu Glu Leu Thr Arg Leu Glu Pro Glu Asp
                165                 170                 175

Thr Ala Leu Tyr Tyr Cys Ala Arg Asn Gln His Gly Leu Asn Lys Gly
            180                 185                 190

Gln Gly Thr Gln Val Thr Val Ser Ser Gly Gly Gly Ser Gly Gly
        195                 200                 205

Gly Gly Ser Asp Val Gln Leu Val Glu Ser Gly Gly Gly Leu Val Gln
```

Ala Gly Gly Ser Thr Arg Leu Thr Cys Lys Ala Ser Gly Ser Ile Ser
225                 230                 235                 240

Asn Ile Asn Ser Ile Asn Val Met Ala Trp Tyr Arg Gln Ala Pro Gly
                245                 250                 255

Lys Gly Arg Glu Leu Val Ala Ile Ile Gly Lys Gly Gly Thr Asn
            260                 265                 270

Tyr Ala Asp Phe Val Lys Gly Arg Phe Thr Ile Ser Arg Asp Ala Ala
        275                 280                 285

Lys Asn Thr Val Tyr Leu Gln Met Asn Ser Leu Arg Pro Glu Asp Thr
    290                 295                 300

Ala Val Tyr Tyr Cys Tyr Ala Asp Tyr Glu Asp His Asp Ser Pro His
305                 310                 315                 320

Asn Ala Ser Trp Gly Gln Gly Thr Gln Val Thr Val Ser Ser
                325                 330

<210> SEQ ID NO 24
<211> LENGTH: 344
<212> TYPE: PRT
<213> ORGANISM: Artificial Sequence
<220> FEATURE:
<223> OTHER INFORMATION: Polypeptide sequence of ID-14K including export
      signal sequence

<400> SEQUENCE: 24

Met Met Arg Phe Pro Ser Ile Phe Thr Ala Val Leu Phe Ala Ala Ser
1               5                   10                  15

Ser Ala Leu Ala Ala Pro Val Asn Thr Thr Thr Glu Asp Glu Thr Ala
            20                  25                  30

Gln Ile Pro Ala Glu Ala Val Ile Gly Tyr Ser Asp Leu Glu Gly Asp
        35                  40                  45

Phe Asp Val Ala Val Leu Pro Phe Ser Asn Ser Thr Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Glu Lys Arg Asp Val Gln Leu Val Glu Ser Gly Gly Gly
                85                  90                  95

Leu Val Gln Pro Gly Gly Ser Leu Lys Leu Ser Cys Ala Ala Ser Gly
            100                 105                 110

Phe Asp Phe Ser Ser His Trp Met Tyr Trp Val Arg Gln Ala Pro Gly
        115                 120                 125

Lys Glu Leu Glu Trp Leu Ser Glu Ile Asn Thr Asn Gly Leu Ile Thr
    130                 135                 140

His Tyr Gly Asp Ser Val Lys Gly Arg Phe Thr Val Ser Arg Asn Asn
145                 150                 155                 160

Ala Ala Asn Lys Met Tyr Leu Glu Leu Thr Arg Leu Glu Pro Glu Asp
                165                 170                 175

Thr Ala Leu Tyr Tyr Cys Ala Arg Asn Gln His Gly Leu Asn Lys Gly
            180                 185                 190

Gln Gly Thr Gln Val Thr Val Ser Ser Gly Gly Gly Ser Gly Gly
        195                 200                 205

Gly Gly Ser Gly Gly Gly Ser Gly Gly Gly Ser Asp Val Gln
    210                 215                 220

Leu Val Glu Ser Gly Gly Gly Leu Val Gln Ala Gly Gly Ser Thr Arg
225                 230                 235                 240

```
Leu Thr Cys Lys Ala Ser Gly Ser Ile Ser Asn Ile Asn Ser Ile Asn
                245                 250                 255

Val Met Ala Trp Tyr Arg Gln Ala Pro Gly Lys Gly Arg Glu Leu Val
            260                 265                 270

Ala Ile Ile Gly Lys Gly Gly Thr Asn Tyr Ala Asp Phe Val Lys
        275                 280                 285

Gly Arg Phe Thr Ile Ser Arg Asp Ala Ala Lys Asn Thr Val Tyr Leu
        290                 295                 300

Gln Met Asn Ser Leu Arg Pro Glu Asp Thr Ala Val Tyr Tyr Cys Tyr
305                 310                 315                 320

Ala Asp Tyr Glu Asp His Asp Ser Pro His Asn Ala Ser Trp Gly Gln
                325                 330                 335

Gly Thr Gln Val Thr Val Ser Ser
            340
```

<210> SEQ ID NO 25
<211> LENGTH: 1049
<212> TYPE: DNA
<213> ORGANISM: Artificial Sequence
<220> FEATURE:
<223> OTHER INFORMATION: Polynucleotide sequence encoding SEQ ID NO: 19

<400> SEQUENCE: 25

```
gagctcatca cacaaacaaa caaaacaaaa tgatgagatt ccttcaatt tttactgccg      60
ttttattcgc agcatcctcc gcattagctg ctccagtcaa cactacaaca gaagatgaaa    120
cggcacaaat tccggctgaa gctgtcatcg gttactcaga tttagaaggg gatttcgatg    180
ttgctgtttt gccatttcc aacagcacaa ataacgggtt attgtttata aatactacta    240
ttgccagcat tgctgctaaa gaagaagggg tatctctcga gaaaagagat gttcaattgg    300
ttgaatccgg tggtggtttg gttcaaccag gtggttcttt gaaattgtct tgtgctgctt    360
ctggtttcga tttctcttct cattggatgt actgggttag acaagctcca ggtaaagaat    420
tggaatggtt gtctgaaatc aacaccaacg gtttgattac ccattatggt gattctgtca    480
agggtagatt cactgtctct agaaacaatg ctgctaacaa gatgtacttg gaattgacca    540
gattggaacc agaagatact gccttgtatt actgcgctag aaatcaacat ggtttgaaca    600
aaggtcaagg tactcaagtt actgtttctt caggtggtgg tggtagtaag ggcggtggtg    660
gttcagatgt tcaattagta gaaagtggtg gtggtttagt acaagctggt ggtagtacta    720
gattgacttg taaggcttcc ggttccatct ccaacattaa ctccattaac gttatggcct    780
ggtatagaca agcacctggt aagggtagag aattggttgc tattattggt aaaggtggtg    840
gtacaaacta cgccgatttt gttaagggta gattcaccat ttcaagagat gctgctaaga    900
acaccgttta cttgcaaatg aactccttaa gacctgaaga taccgctgtt tattactgct    960
atgctgatta cgaagatcac gattctccac ataatgcttc atggggtcaa ggtacacagg   1020
tcaccgtttc ctcataatga cttaagctt                                    1049
```

<210> SEQ ID NO 26
<211> LENGTH: 1049
<212> TYPE: DNA
<213> ORGANISM: Artificial Sequence
<220> FEATURE:
<223> OTHER INFORMATION: Polynucleotide sequence encoding SEQ ID NO: 20

<400> SEQUENCE: 26

```
gagctcatca cacaaacaaa caaaacaaaa tgatgagatt ccttcaatt tttactgccg      60
```

-continued

```
ttttattcgc agcatcctcc gcattagctg ctccagtcaa cactacaaca gaagatgaaa    120
cggcacaaat tccggctgaa gctgtcatcg gttactcaga tttagaaggg gatttcgatg    180
ttgctgtttt gccattttcc aacagcacaa ataacgggtt attgtttata aatactacta    240
ttgccagcat tgctgctaaa gaagaagggg tatctctcga gaaaagagat gttcaattgg    300
ttgaatccgg tggtggtttg gttcaagctg gtggttctac tagattgact tgtaaggctt    360
ccggttccat ctccaacatt aactccatta acgttatggc ctggtataga caagctccag    420
gtaaaggtag agaattggtt gctattattg gtaagggtgg tggtactaat tacgccgatt    480
ttgttaaggg tagattcacc atttctagag atgctgctaa gaacaccgtt tacttgcaaa    540
tgaactcctt aagaccagaa gataccgctg tttattactg ctatgctgat tacgaagatc    600
acgattctcc acataatgct tcatggggtc aaggtactca agttactgtt tcttcaggtg    660
gtggtggttc aaagggcggt ggtggtagtg atgtacaatt agtagaaagt ggtggtggtt    720
tagtacaacc aggtggtagt ttgaaattgt cttgtgctgc ttctggtttc gatttctctt    780
ctcattggat gtactgggtt agacaagcac ctggtaaaga attggaatgg ttgtctgaaa    840
tcaacaccaa cggtttgatt acccattatg gtgattctgt caaaggtaga ttcaccgtca    900
gtagaaacaa tgctgccaac aaaatgtact tggaattgac cagattggaa cctgaagata    960
ctgccttgta ttactgcgct agaaatcaac atggtttgaa caaaggtcaa ggtacacagg   1020
tcaccgtttc ctcataatga cttaagctt                                     1049
```

<210> SEQ ID NO 27
<211> LENGTH: 1106
<212> TYPE: DNA
<213> ORGANISM: Artificial Sequence
<220> FEATURE:
<223> OTHER INFORMATION: Polynucleotide sequence encoding SEQ ID NO: 21

<400> SEQUENCE: 27

```
gagctcatca cacaaacaaa caaaacaaaa tgatgagatt tccttcaatt tttactgccg     60
ttttattcgc agcatcctcc gcattagctg ctccagtcaa cactacaaca gaagatgaaa    120
cggcacaaat tccggctgaa gctgtcatcg gttactcaga tttagaaggg gatttcgatg    180
ttgctgtttt gccattttcc aacagcacaa ataacgggtt attgtttata aatactacta    240
ttgccagcat tgctgctaaa gaagaagggg tatctctcga gaaaagagat gttcaattgg    300
ttgaatccgg tggtggtttg gttcaaccag gtggttcttt gaaattgtct tgtgctgctt    360
ctggtttcga tttctcttct cattggatgt actgggttag acaagctcca ggtaaagaat    420
tggaatggtt gtctgaaatc aacaccaacg gtttgattac ccattatggt gattctgtca    480
agggtagatt cactgtctct agaaacaatg ctgctaacaa gatgtacttg gaattgacca    540
gattggaacc agaagatact gccttgtatt actgcgctag aaatcaacat ggtttgaaca    600
aaggtcaagg tactcaagtt actgtttctt caggtggagg cggttcaggc ggaggtggct    660
ctggcggtgg cggaagtggt ggcggtggat caggtggtgg cggttcgggc ggtggtggaa    720
gcgatgttca attagtagaa agtggtggtg gtttagtaca agctggtggt agtactagat    780
tgacttgtaa ggcttccggt tccatctcca acattaactc cattaacgtt atggcctggt    840
atagacaagc acctggtaag ggtagagaat tggttgctat tattggtaaa ggtggtggta    900
caaactacgc cgattttgtt aagggtagat tcaccatttc aagagatgct gctaagaaca    960
ccgtttactt gcaaatgaac tccttaagac ctgaagatac cgctgtttat tactgctatg   1020
ctgattacga agatcacgat tctccacata atgcttcatg gggtcaaggt acacaggtca   1080
```
ccgtttcctc ataatgactt aagctt 1106

<210> SEQ ID NO 28
<211> LENGTH: 1106
<212> TYPE: DNA
<213> ORGANISM: Artificial Sequence
<220> FEATURE:
<223> OTHER INFORMATION: Polynucleotide sequence encoding SEQ ID NO: 22

<400> SEQUENCE: 28

```
gagctcatca cacaaacaaa caaaacaaaa tgatgagatt ccttcaatt tttactgccg      60
ttttattcgc agcatcctcc gcattagctg ctccagtcaa cactacaaca gaagatgaaa    120
cggcacaaat tccggctgaa gctgtcatcg gttactcaga tttagaaggg gatttcgatg    180
ttgctgtttt gccatttttcc aacagcacaa ataacgggtt attgtttata aatactacta   240
ttgccagcat tgctgctaaa gaagaagggg tatctctcga gaaaagagat gttcaattgg    300
ttgaatccgg tggtggtttg gttcaagctg gtggttctac tagattgact tgtaaggctt    360
ccggttccat ctccaacatt aactccatta acgttatggc ctggtataga caagctccag    420
gtaaaggtag agaattggtt gctattattg gtaaggtgg tggtactaat tacgccgatt     480
ttgttaaggg tagattcacc atttctagag atgctgctaa gaacaccgtt tacttgcaaa    540
tgaactcctt aagaccagaa gataccgctg tttattactg ctatgctgat tacgaagatc    600
acgattctcc acataatgct tcatggggtc aaggtactca agttactgtt tcttcaggtg    660
gaggcggttc aggcggaggt ggctctggcg gtggcggaag tggtggcggt ggatcaggtg    720
gtggcggttc gggcggtggt ggaagcgatg tacaattagt agaaagtggt ggtggtttag    780
tacaaccagg tggtagtttg aaattgtctt gtgctgcttc tggtttcgat ttctcttctc    840
attggatgta ctgggttaga caagcacctg gtaaagaatt ggaatggttg tctgaaatca    900
acaccaacgg tttgattacc cattatggta attctgtcaa aggtagattc accgtcagta    960
gaaacaatgc tgccaacaaa atgtacttgg aattgaccag attggaacct gaagatactg   1020
ccttgtatta ctgcgctaga aatcaacatg gtttgaacaa aggtcaaggt acacaggtca   1080
ccgtttcctc ataatgactt aagctt                                        1106
```

<210> SEQ ID NO 29
<211> LENGTH: 1046
<212> TYPE: DNA
<213> ORGANISM: Artificial Sequence
<220> FEATURE:
<223> OTHER INFORMATION: Polynucleotide sequence encoding SEQ ID NO: 23

<400> SEQUENCE: 29

```
gagctcatca cacaaacaaa caaaacaaaa tgatgagatt ccttcaatt tttactgccg      60
ttttattcgc agcatcctcc gcattagctg ctccagtcaa cactacaaca gaagatgaaa    120
cggcacaaat tccggctgaa gctgtcatcg gttactcaga tttagaaggg gatttcgatg    180
ttgctgtttt gccatttttcc aacagcacaa ataacgggtt attgtttata aatactacta   240
ttgccagcat tgctgctaaa gaagaagggg tatctctcga gaaaagagat gttcaattgg    300
ttgaatccgg tggtggtttg gttcaaccag gtggttcttt gaaattgtct tgtgctgctt    360
ctggtttcga tttctcttct cattggatgt actgggttag acaagctcca ggtaaagaat    420
tggaatggtt gtctgaaatc aacaccaacg gtttgattac ccattatggt gattctgtca    480
agggtagatt cactgtctct agaaacaatg ctgctaacaa gatgtacttg gaattgacca    540
```

```
gattggaacc agaagatact gccttgtatt actgcgctag aaatcaacat ggtttgaaca      600
aaggtcaagg tactcaagtt actgtttctt caggtggagg cggttcaggc ggaggtggct      660
ctgatgttca attagtagaa agtggtggtg gtttagtaca agctggtggt agtactagat      720
tgacttgtaa ggcttccggt tccatctcca acattaactc cattaacgtt atggcctggt      780
atagacaagc acctggtaag ggtagagaat tggttgctat tattggtaaa ggtggtggta      840
caaactacgc cgattttgtt aagggtagat tcaccatttc aagagatgct gctaagaaca      900
ccgtttactt gcaaatgaac tccttaagac ctgaagatac cgctgtttat tactgctatg      960
ctgattacga agatcacgat tctccacata atgcttcatg gggtcaaggt acacaggtca     1020
ccgtttcctc ataatgactt aagctt                                          1046
```

<210> SEQ ID NO 30
<211> LENGTH: 1076
<212> TYPE: DNA
<213> ORGANISM: Artificial Sequence
<220> FEATURE:
<223> OTHER INFORMATION: Polynucleotide sequence encoding SEQ ID NO: 24

<400> SEQUENCE: 30

```
gagctcatca cacaaacaaa caaaacaaaa tgatgagatt tccttcaatt tttactgccg       60
ttttattcgc agcatcctcc gcattagctg ctccagtcaa cactacaaca gaagatgaaa      120
cggcacaaat tccggctgaa gctgtcatcg gttactcaga tttagaaggg gatttcgatg      180
ttgctgtttt gccatttttcc aacagcacaa ataacgggtt attgtttata aatactacta      240
ttgccagcat tgctgctaaa gaagaagggg tatctctcga gaaaagagat gttcaattgg      300
ttgaatccgg tggtggtttg gttcaaccag gtggttcttt gaaattgtct tgtgctgctt      360 ctggttttcga tttctcttct cattggatgt actgggttag acaagctcca ggtaaagaat      420
tggaatggtt gtctgaaatc aacaccaacg gtttgattac ccattatggt gattctgtca      480
agggtagatt cactgtctct agaaacaatg ctgctaacaa gatgtacttg gaattgacca      540
gattggaacc agaagatact gccttgtatt actgcgctag aaatcaacat ggtttgaaca      600
aaggtcaagg tactcaagtt actgtttctt caggtggagg cggttcaggc ggaggtggct      660
ctggcggtgg cggaagtggt ggcggtggat cagatgttca attagtagaa agtggtggtg      720
gtttagtaca agctggtggt agtactagat tgacttgtaa ggcttccggt tccatctcca      780
acattaactc cattaacgtt atggcctggt atagacaagc acctggtaag ggtagagaat      840
tggttgctat tattggtaaa ggtggtggta caaactacgc cgattttgtt aagggtagat      900
tcaccatttc aagagatgct gctaagaaca ccgtttactt gcaaatgaac tccttaagac      960
ctgaagatac cgctgtttat tactgctatg ctgattacga agatcacgat tctccacata     1020
atgcttcatg gggtcaaggt acacaggtca ccgtttcctc ataatgactt aagctt         1076
```

<210> SEQ ID NO 31
<211> LENGTH: 5
<212> TYPE: PRT
<213> ORGANISM: Artificial Sequence
<220> FEATURE:
<223> OTHER INFORMATION: Polypeptide sequence of enterokinase cleavage
      site

<400> SEQUENCE: 31

```
Asp Asp Asp Asp Lys
1               5
```

```
<210> SEQ ID NO 32
<211> LENGTH: 11
<212> TYPE: PRT
<213> ORGANISM: Artificial Sequence
<220> FEATURE:
<223> OTHER INFORMATION: Polypeptide sequence of specific labile linker
      used in ID-9K and ID-10K

<400> SEQUENCE: 32

Gly Gly Gly Gly Ser Lys Gly Gly Gly Gly Ser
1               5                   10

<210> SEQ ID NO 33
<211> LENGTH: 30
<212> TYPE: PRT
<213> ORGANISM: Artificial Sequence
<220> FEATURE:
<223> OTHER INFORMATION: Polypeptide sequence of specific non-labile
      linker used in ID-11K

<400> SEQUENCE: 33

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 34
<211> LENGTH: 123
<212> TYPE: PRT
<213> ORGANISM: Artificial Sequence
<220> FEATURE:
<223> OTHER INFORMATION: Polypeptide sequence of ID-123V

<400> SEQUENCE: 34

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gly Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Tyr Leu Gln Met Asn Ser Leu Arg Pro Glu Asp Thr Ala Val Tyr
                85                  90                  95

Tyr Cys Tyr Ala Asp Tyr Glu Asp His Asp Ser Pro His Asn Ala Ser
            100                 105                 110

Trp Gly Gln Gly Thr Gln Val Thr Val Ser Ser
        115                 120

<210> SEQ ID NO 35
<211> LENGTH: 28
<212> TYPE: DNA
<213> ORGANISM: Unknown
<220> FEATURE:
<223> OTHER INFORMATION: 3' primer containing the SpeI site

<400> SEQUENCE: 35
tcttaactag tgaggagacg gtgacctg                                    28

<210> SEQ ID NO 36
<211> LENGTH: 9
```

```
<212> TYPE: PRT
<213> ORGANISM: Unknown
<220> FEATURE:
<223> OTHER INFORMATION: Exemplary residues 1 to 9 of CDR2 of the
      TNF-alpha binding polypeptide

<400> SEQUENCE: 36

Glu Ile Asn Thr Asn Gly Leu Ile Thr
1               5

<210> SEQ ID NO 37
<211> LENGTH: 4
<212> TYPE: PRT
<213> ORGANISM: Unknown
<220> FEATURE:
<223> OTHER INFORMATION: Exemplary last four residues of FR1 of the
      IL-6R binding polypeptide

<400> SEQUENCE: 37

Asn Ile Asn Ser
1
```

COMPOSITIONS

This application is a continuation-in-part of International Application No. PCT/EP2017/074828 filed Sep. 29, 2017, which claims priority to European Application No. 16191988.1 filed Sep. 30, 2016, the contents of which are incorporated herewith in their entirety.

SEQUENCE LISTING

The instant application contains a Sequence Listing which has been submitted electronically in text format and is hereby incorporated by reference in its entirety. Said text file, created on Jul. 5, 2021 is named 2021_07_05_VHSP2039USC1_Corrected_Sequence_Listing.txt and is 37,200 bytes in size.

FIELD OF THE INVENTION

The present invention relates to compositions and constructs comprising a TNF-alpha binding polypeptide and an IL-6R binding polypeptide. The present invention also relates to nucleic acids encoding such constructs, to methods for preparing such compositions and constructs, to cDNA and vectors comprising nucleic acids encoding such constructs, to host cells expressing or capable of expressing such constructs and to uses of such compositions and constructs.

BACKGROUND OF THE INVENTION

Tumour necrosis factor-alpha is a homotrimeric pro-inflammatory cytokine involved in systemic inflammation which exists in both soluble and membrane-bound forms. TNF-alpha is secreted predominantly by monocytes and macrophages but is also secreted by tumour cell lines as well as CD4+ and CD8+ peripheral blood T lymphocytes and some cultured T and B cell lines. TNF-alpha has been implicated in inflammatory diseases, autoimmune diseases, viral, bacterial and parasitic infections, malignancies, and/or neurodegenerative diseases and is a target for specific biological therapy in autoimmune/autoinflammatory diseases such as rheumatoid arthritis and Crohn's disease. A TNF-alpha inhibitor which has sufficient specificity to TNF-alpha may be an efficient prophylactic or therapeutic pharmaceutical for preventing or treating diseases such as Crohn's disease, where TNF-alpha has been implicated as a key cytokine driving the pathology observed.

IL-6 induces cell activation via a receptor system that consists of two receptor chains: a ligand-specific non-signalling transmembrane IL-6 receptor alpha subunit (the membrane-bound form of IL-6R, also known as mIL-6R, IL-6Rα, gp80 and CD126) and a second trans-membrane receptor chain gp130 that is required for signal transduction. In classical (cis) IL-6 signalling, IL-6 first binds to the membrane IL-6Ra subunit, which in turn associates with gp130 to form an IL-6-receptor complex that is able to induce cell activation. The restricted expression of membrane IL-6Ra receptors limits this classical IL-6 signalling mechanism to a few cell types including hepatocytes, neutrophils, monocyte/macrophages, some lymphocyte subtypes and intestinal epithelial cells. A second form of the IL-6R comprising the extracellular ligand-binding region of the IL-6Rα-subunit has also been identified. The soluble form of the IL-6R (sIL-6R) is generated by protease mediated shedding of IL-6Ra ecto-domains from membrane IL-6R expressing cells or is secreted from the cells as an alternatively spliced product. Importantly, IL-6 can still bind to the sIL-6R and the IL-6/sIL-6R complexes formed can associate with gp130-receptor chains to induce signalling. As a wide range of cells express gp130 but not the IL-6R, this process termed "trans-signalling" provides a mechanism for extending the range of cell types that are capable of responding to IL-6 and this process appears to be particularly important for the development and perpetuation of chronic inflammation (Rose-John 2012). Inhibition of the IL-6R has potential for therapeutic benefit in autoimmune diseases such as Crohn's disease (CD) and ulcerative colitis (UC). Systemically administered IL-6 pathway antagonists including both IL-6 and IL-6R blocking antibodies have demonstrated efficacy without major toxicity in inflammatory diseases including rheumatoid arthritis and Castleman's disease. Tocilizumab, a humanised IL-6R monoclonal antibody that targets both membrane and soluble IL-6Rs (cis/trans signalling inhibitor) has also shown evidence of clinical efficacy in a pilot clinical study in patients with Crohn's disease (Ito et al., 2004).

TNF-alpha and IL-6 are both therefore cytokines that regulate cell types and pathways involved in the development and maintenance of intestinal inflammation in IBD. Although the relative contributions of these cytokines to different disease processes are unclear, the results of clinical studies have shown that antibodies that antagonise the actions of either TNF-alpha or IL-6/IL-6R signalling are effective in Crohn's patients. However, these antibodies have limited efficacy. Accordingly, there exists today a need for improved IBD therapeutics.

WO2004041862, WO2006122786 and Coppieters et al 2006 (herein incorporated by reference in their entirety) disclose single domain antibodies directed against TNF-alpha and related aspects. The sequence referred to in WO 2006/122786 as "TNF1", "PMP1C2" or "SEQ ID NO: 52") is characterised further below.

WO2008020079, WO2008071685, WO2009095489, WO2010115995, WO2010115998 and WO2013041722 (herein incorporated by reference in their entirety) disclose single domain antibodies directed against IL-6R and related aspects. The sequence referred to in WO2010115998 as "20A11" or "SEQ ID NO: 66" is characterised further below.

WO2015065987 (herein incorporated by reference in its entirety) discloses a bispecific antibody comprising at least one anti-TNF-alpha antibody or antigen-binding fragment thereof and at least one anti-IL-6 antibody or antigen-binding fragment thereof.

Compositions or constructs of the present invention may, in at least some embodiments, have one or more of the following advantages compared to substances of the prior art. These advantages may be realised by each of the component polypeptides in a composition of the invention in their own right, or alternatively the combination of the polypeptides in a composition of the invention may result in an additive or even synergistic effect in respect of one or more of the below advantages.

(a) increased affinity and/or avidity for TNF-alpha and/or IL-6R;
(b) increased specificity for TNF-alpha and/or IL-6R;
(c) increased neutralising capability against TNF-alpha and/or IL-6R;
(d) increased inhibition of phosphorylation of signalling proteins;
(e) increased inhibition of cytokine production;

(f) increased cross-reactivity with TNF-alpha and/or IL-6R from different species such as human and cynomolgus monkey;

(g) increased cross-reactivity with both soluble and membrane forms of TNF-alpha;

(h) reduced immunogenicity, for example when administered to a mouse, cynomolgus monkey or human;

(i) increased stability in the presence of proteases, for example (a) in the presence of proteases found in the small and/or large intestine and/or IBD inflammatory proteases, for example trypsin, chymotrypsin, enterokinase, MMP3, MMP10, MMP12, other MMPs and cathepsin and/or (b) in the presence of proteases such as cell membrane-attached proteases, secreted proteases and proteases released on cell lysis from gut commensal microflora and/or pathogenic bacteria, found in the small and/or large intestine;

(j) increased stability to protease degradation during production (for example resistance to yeast proteases);

(k) increased suitability for oral administration;

(l) increased suitability for local delivery to the intestinal tract and lamina propria following oral administration;

(m) increased suitability for expression in a heterologous host such as bacteria (e.g. *Escherichia coli*) or a yeast (e.g. *Saccharomyces cerevisiae*);

(n) suitability for, and improved properties for, use in a pharmaceutical;

(o) suitability for, and improved properties for, use in a functional food;

(p) improved tissue penetration such as penetration of inflamed colonic mucosal epithelium and submucosal tissues to access the sub mucosal lamina propria;

(q) decreased immunogenicity in humans for example due to increased sequence similarity to human immunoglobulins;

(r) more effective prevention or treatment of autoimmune disease and/or inflammatory disease, including amelioration of the symptoms thereof, including in particular inflammatory bowel disease and/or mucositis, particularly when administered orally;

(s) binding to novel epitopes.

SUMMARY OF THE INVENTION

The present inventors have provided surprisingly effective compositions comprising a TNF-alpha binding polypeptide and an IL-6R binding polypeptide. In particular, it has been found that the provision of a TNF-alpha binding polypeptide and an IL-6R binding polypeptide in a single composition may be more effective than the provision of each binding polypeptide separately. In some embodiments, the combination of these polypeptides in compositions of the invention may have an additive effect and in further embodiments, the combination of these polypeptides in compositions of the invention may have a synergistic effect.

Based on the findings disclosed herein using ex vivo cultured intestinal mucosal tissue from inflammatory bowel disease patients (Examples 10 and 11) it may be expected that these compositions have particular utility in the prevention or treatment of autoimmune and or inflammatory disease. More specifically, the findings disclosed herein indicate that these compositions may have particular utility in the prevention or treatment of inflammatory bowel disease (for example Crohn's disease or ulcerative colitis), or in the prevention or treatment of mucositis, particularly when administered orally.

It may be expected that the same benefits may be derived by the use of a TNF-alpha binding polypeptide in the treatment or prevention of disease, together with an IL-6R binding polypeptide, wherein the polypeptides are not combined in the same composition. Similarly, it may be expected that the same benefits may be derived by the use of an IL-6R binding polypeptide in the treatment or prevention of disease, together with a TNF-alpha binding polypeptide, wherein the polypeptides are not combined in the same composition.

The present invention provides a composition comprising a TNF-alpha binding polypeptide and an IL-6R binding polypeptide.

Also provided is a construct comprising a TNF-alpha binding polypeptide and an IL-6R binding polypeptide, and a polynucleotide encoding said construct.

Also provided is a TNF-alpha binding polypeptide for use in the treatment or prevention of an autoimmune disease and/or inflammatory disease, together with an IL-6R binding polypeptide; and an IL-6R binding polypeptide for use in the treatment or prevention of an autoimmune disease and/or inflammatory disease, together with a TNF-alpha binding polypeptide.

Many of the specific TNF-alpha binding polypeptides, the specific IL-6R binding polypeptides and the data disclosed herein are also disclosed in particular earlier-filed patent applications. These include PCT application number PCT/EP2016/057021 (which is incorporated herein by reference in its entirety, particularly in so far as the application relates to the TNF-alpha binding polypeptide ID-38F) and EP application number 16152321.2 and PCT application number PCT/EP2017/051237 (which are incorporated herein by reference in their entireties, particularly in so far as the applications relate to the IL-6R binding polypeptide ID-142V).

DESCRIPTION OF THE SEQUENCES

Figure 1:
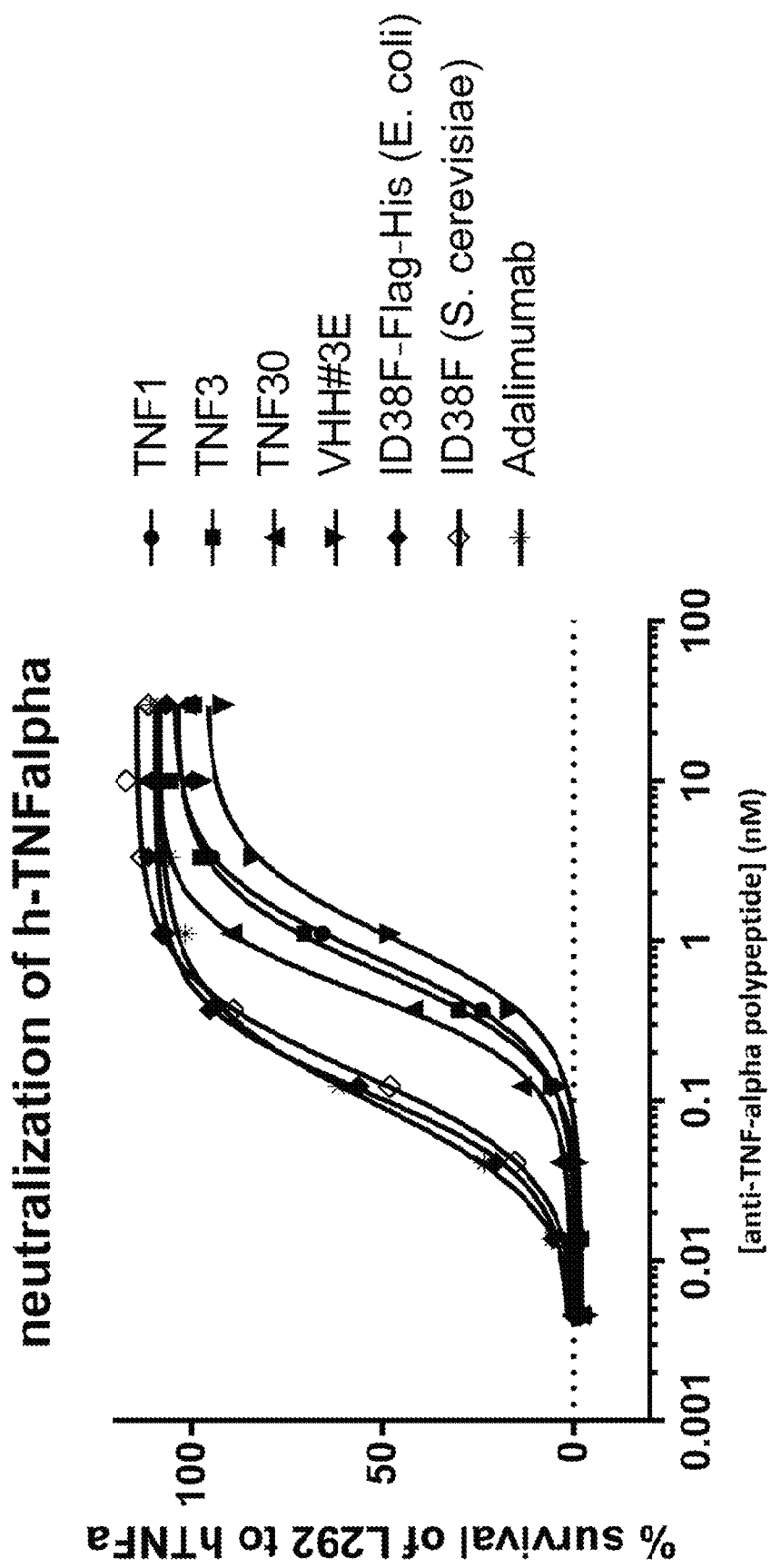
FIG. 1—Potency of ID-38F compared to TNF-alpha binding polypeptides of the prior art (L929 assay)

SEQ ID NO: 1—Polypeptide sequence of CDR1 of ID-38F
SEQ ID NO: 2—Polypeptide sequence of CDR2 of ID-38F
SEQ ID NO: 3—Polypeptide sequence of CDR3 of ID-38F
SEQ ID NO: 4—Polypeptide sequence of FR1 of ID-38F
SEQ ID NO: 5—Polypeptide sequence of FR2 of ID-38F
SEQ ID NO: 6—Polypeptide sequence of FR3 of ID-38F
SEQ ID NO: 7—Polypeptide sequence of FR4 of ID-38F
SEQ ID NO: 8—Polypeptide sequence of ID-38F
SEQ ID NO: 9—Polypeptide sequence of CDR1 of ID-142V
SEQ ID NO: 10—Polypeptide sequence of CDR2 of ID-142V
SEQ ID NO: 11—Polypeptide sequence of CDR3 of ID-142V
SEQ ID NO: 12—Polypeptide sequence of FR1 of ID-142V
SEQ ID NO: 13—Polypeptide sequence of FR2 of ID-142V
SEQ ID NO: 14—Polypeptide sequence of FR3 of ID-142V
SEQ ID NO: 15—Polypeptide sequence of FR4 of ID-142V
SEQ ID NO: 16—Polypeptide sequence of ID-142V
SEQ ID NO: 17—Polynucleotide sequence encoding ID-38F
SEQ ID NO: 18—Polynucleotide sequence encoding ID-142V
SEQ ID NO: 19—Polypeptide sequence of ID-9K including export signal sequence
SEQ ID NO: 20—Polypeptide sequence of ID-10K including export signal sequence
SEQ ID NO: 21—Polypeptide sequence of ID-11K including export signal sequence
SEQ ID NO: 22—Polypeptide sequence of ID-12K including export signal sequence
SEQ ID NO: 23—Polypeptide sequence of ID-13K including export signal sequence
SEQ ID NO: 24—Polypeptide sequence of ID-14K including export signal sequence
SEQ ID NO: 25—Polynucleotide sequence encoding SEQ ID NO: 19
SEQ ID NO: 26—Polynucleotide sequence encoding SEQ ID NO: 20
SEQ ID NO: 27—Polynucleotide sequence encoding SEQ ID NO: 21
SEQ ID NO: 28—Polynucleotide sequence encoding SEQ ID NO: 22
SEQ ID NO: 29—Polynucleotide sequence encoding SEQ ID NO: 23
SEQ ID NO: 30—Polynucleotide sequence encoding SEQ ID NO: 24
SEQ ID NO: 31—Polypeptide sequence of enterokinase cleavage site
SEQ ID NO: 32—Polypeptide sequence of specific labile linker used in ID-9K and ID-10K
SEQ ID NO: 33—Polypeptide sequence of specific non-labile linker used in ID-11K
SEQ ID NO: 34—Polypeptide sequence of ID-123V
SEQ ID NO: 35—Polynucleotide sequence of 3' primer containing the SpeI site
SEQ ID NO: 36—Polypeptide sequence of exemplary residues 1 to 9 of CDR2 of the TNF-alpha binding polypeptide
SEQ ID NO: 37—Polypeptide sequence of exemplary last four residues of FR1 of the IL-6R binding polypeptide

DETAILED DESCRIPTION OF THE INVENTION

Polypeptides such as antibodies and antibody fragments including immunoglobulin chain variable domains (ICVDs) such as the VH and VHH Polypeptides are organic polymers consisting of a number of amino acid residues bonded together in a chain. As used herein, 'polypeptide' is used interchangeably with 'protein' and 'peptide'. Polypeptides are said to be binding polypeptides when they contain one or more stretches of amino acid residues which form a binding site, capable of binding to an epitope on a target, with an affinity (suitably expressed as a Kd value, a Ka value, a $k_{on}$-rate and/or a $k_{off}$-rate, as further described herein).

Binding polypeptides include polypeptides such as DARPins (Binz et al. 2003), Affimers™ (Johnson et al 2012), Fynomers™ (Grabulovski et al 2007), Centyrins (Goldberg et al 2016), Affitins (e.g. Nanofitins®, Krehenbrink et al 2008), cyclic peptides, antibodies and antibody fragments. Binding polypeptides also include polypeptides such as Affibodies (Nygren 2008), Affilins (Ebersbach et al. 2007), Alphabodies (Desmet et al 2014), Anticalins (Skerra et al 2008), Avimers (Silverman et al 2005), Kunitz domain peptides (Nixon and Wood 2006), Monobodies (Koide and Koide 2007), nanoCLAMPs (Suderman et al 2017), Adnectins (Lipovsek 2011) and bicyclic peptides.

A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains.

The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991 Sequences of Proteins of Immunological Interest, *Fifth Edition U.S. Department of Health and Human Services*, NIH Publication Number 91-3242, herein incorporated by reference in its entirety). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL.

The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994 Mol Immunol 31:169-217).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans et al 2013, Hamers-Casterman et al 1993, Muyldermans et al 1994, herein incorporated by reference in their entirety).

An antibody fragment as used herein refers to a portion of an antibody that specifically binds to a target (e.g. a molecule in which one or more immunoglobulin chains is not full length, but which specifically binds to a target). Examples of binding fragments encompassed within the term antibody fragment (or 'antigen-binding fragment') include:
(i) a Fab fragment (a monovalent fragment consisting of the VLC, VHC, CL and CH1 domains);
(ii) a F(ab')2 fragment (a bivalent fragment comprising two Fab fragments linked by a disulfide bridge at the hinge region);
(iii) a Fd fragment (consisting of the VHC and CH1 domains);
(iv) a Fv fragment (consisting of the VLC and VHC domains of a single arm of an antibody);
(v) an scFv fragment (consisting of VLC and VHC domains joined, using recombinant methods, by a synthetic linker that enables them to be made as a single protein chain in which the VLC and VHC regions pair to form monovalent molecules);
(vi) a VH (an immunoglobulin chain variable domain consisting of a VHC domain (Ward et al 1989);
(vii) a VL (an immunoglobulin chain variable domain consisting of a VLC domain);
(viii) a V-NAR (an immunoglobulin chain variable domain consisting of a VHC domain from chondrichthyes IgNAR (Roux et al 1998 and Griffiths et al 2013, herein incorporated by reference in their entirety)
(ix) a VHH.

The total number of amino acid residues in a VHH or VH may be in the region of 110-140, more suitably 112-120.

The examples provided herein relate to compositions comprising immunoglobulin chain variable domains which bind to TNF-alpha and immunoglobulin chain variable domains which bind to IL-6R. The principles of the invention disclosed herein are, however, equally applicable to any compositions comprising polypeptides which bind to TNF-alpha and polypeptides which bind to IL-6R, such as antibodies and antibody fragments. For example, immunoglobulin chain variable domains may be incorporated into a polypeptide such as a full length antibody. Such an approach is demonstrated by McCoy et al., 2014, who provide an anti-HIV VHH engineered as a fusion with a human Fc region (including hinge, CH2 and CH3 domains), expressed as a dimer construct.

Specificity, Affinity, Avidity, Potency, Inhibition and Neutralisation

Specificity refers to the number of different targets (such as antigens or antigenic determinants) to which a particular binding polypeptide can bind. The specificity of a binding polypeptide is the ability of the binding polypeptide to recognise a particular target as a unique molecular entity and distinguish it from another.

Affinity, represented by the equilibrium constant for the dissociation of a target from a binding polypeptide (Kd), is a measure of the binding strength between a target and a binding site on a binding polypeptide: the lesser the value of the Kd, the stronger the binding strength between a target and the binding polypeptide (alternatively, the affinity can also be expressed as the affinity constant (Ka), which is 1/Kd). Affinity can be determined by known methods, depending on the specific antigen of interest. Suitably, affinity is determined using a dynamically switchable biosurface (e.g. "switchSENSE®", see Knezevic et al 2012) or by surface plasmon resonance.

Avidity is the measure of the strength of binding between a binding polypeptide and the pertinent target. Avidity is related to both the affinity between a target and its binding site on the binding polypeptide and the number of pertinent binding sites present on the binding polypeptide.

Any Kd value less than $10^{-6}$ is considered to indicate binding. Specific binding of a binding polypeptide to a target (such as an antigen or antigenic determinant) can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

Potency is a measure of the activity of a therapeutic agent (such as a binding polypeptide) expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target and the quantitative magnitude of this response. The term half maximal effective concentration (EC50) refers to the concentration of a therapeutic agent which causes a response halfway between the baseline and maximum after a specified exposure time. The therapeutic agent may cause inhibition (which may be referred to specifically as half maximal inhibitory concentration, 'IC50') or stimulation. EC50 and IC50 are commonly used, and are used herein, as a measure of potency. EC50 and IC50 are used interchangeably herein in respect of the TNF-alpha binding polypeptides and IL-6R binding polypeptides, due to both binding polypeptides causing inhibition of a target.

Specific assays which are suitable for ascertaining the potency of TNF-alpha binding polypeptides and IL-6R binding polypeptides are detailed below under the headings 'TNF-alpha binding polypeptides' and 'IL-6R binding polypeptides', respectively.

Polypeptide and Polynucleotide Sequences

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
| --- | --- |
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Threonine |
| | Asparagine |
| | Glutamine |
| Negatively charged | Aspartate |
| | Glutamate |
| Positively charged | Lysine |
| | Arginine |

Suitably, a hydrophobic amino acid residue is a non-polar amino acid. More suitably, a hydrophobic amino acid residue is selected from V, I, L, M, F, W or C.

As used herein, numbering of polypeptide sequences and definitions of CDRs and FRs are as defined according to the Kabat system (Kabat et al 1991 Sequences of Proteins of Immunological Interest, Fifth Edition U.S. Department of Health and Human Services, NIH Publication Number 91-3242, herein incorporated by reference in its entirety). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

The Kabat numbering system is applied below to particular TNF-alpha and IL-6R binding polypeptides used in the examples provided herein.

The Kabat Numbering System Applied to ID-142V, an IL-6R Binding Polypeptide

The CDRs of the ID-142V polypeptide labelled below as 'CDR-H1', 'CDR2-H2' and 'CDR-H3' relate to 'CDR1', 'CDR2' and 'CDR3' respectively, as discussed herein. Numbering in the ID-142V figure below with the prefix 'H' is Kabat numbering, while numbering below the amino acid sequence is numbering of amino acids consecutively from N- to C-terminus. The residues of each CDR or FR can also be numbered from the N- to the C-terminus of that CDR or FR.

| | H1 | H2 | H3 | H4 | H5 | H6 | H7 | H8 | H9 | H10 | H11 | H12 | H13 |
| --- | --- | --- | --- | --- | --- | --- | --- | --- | --- | --- | --- | --- | --- |
| ID-142V | D | V | Q | L | V | E | S | G | G | G | L | V | Q |
| | 1 | 2 | 3 | 4 | 5 | 6 | 7 | 8 | 9 | 10 | 11 | 12 | 13 |

| | H14 | H15 | H16 | H17 | H18 | H19 | H20 | H21 | H22 | H23 | H24 | H25 | H26 |
| --- | --- | --- | --- | --- | --- | --- | --- | --- | --- | --- | --- | --- | --- |
| | A | G | G | S | T | R | L | T | C | K | A | S | G |
| | 14 | 15 | 16 | 17 | 18 | 19 | 20 | 21 | 22 | 23 | 24 | 25 | 26 |

-continued

| | | | | | | | | | | | | |
|---|---|---|---|---|---|---|---|---|---|---|---|---|
| | | | | | | | CDR1 | | | | | |
| H27 | H28 | H29 | H29A | H29B | H29C | H30 | H31 | H32 | H33 | H34 | H35 | H36 |
| S | I | S | N | I | N | S | I | N | V | M | A | W |
| 27 | 28 | 29 | 30 | 31 | 32 | 33 | 34 | 35 | 36 | 37 | 38 | 39 |

| H37 | H38 | H39 | H40 | H41 | H42 | H43 | H44 | H45 | H46 | H47 | H48 | H49 |
| Y | R | Q | A | P | G | K | G | R | E | L | V | A |
| 40 | 41 | 42 | 43 | 44 | 45 | 46 | 47 | 48 | 49 | 50 | 51 | 52 |
| CDR2 | | | | | | | | | | | | |
| H50 | H51 | H52 | H53 | H54 | H55 | H56 | H57 | H58 | H59 | H60 | H61 | H62 |
| I | I | G | K | G | G | G | T | N | Y | A | D | F |
| 53 | 54 | 55 | 56 | 57 | 58 | 59 | 60 | 61 | 62 | 63 | 64 | 65 |
| CDR2 | | | | | | | | | | | | |
| H63 | H4 | H65 | H66 | H67 | H68 | H69 | H70 | H71 | H72 | H73 | H74 | H75 |
| V | K | G | R | F | T | I | S | R | D | A | A | K |
| 66 | 67 | 68 | 69 | 70 | 71 | 72 | 73 | 74 | 75 | 76 | 77 | 78 |

| H76 | H77 | H78 | H79 | H80 | H81 | H82 | H82A | H82B | H82C | H83 | H84 | H85 |
| N | T | V | Y | L | Q | M | N | S | L | R | P | E |
| 79 | 80 | 81 | 82 | 83 | 84 | 85 | 86 | 87 | 88 | 89 | 90 | 91 |
| | | | | | | | | | CDR-H3 | | | |
| H86 | H87 | H88 | H89 | H90 | H91 | H92 | H93 | H94 | H95 | H96 | H97 | H98 |
| D | T | A | V | Y | Y | C | Y | A | D | Y | E | D |
| 92 | 93 | 94 | 95 | 96 | 97 | 98 | 99 | 100 | 101 | 102 | 103 | 104 |
| CDR3 | | | | | | | | | | | | |
| H99 | H100 | H100A | H100B | H100C | H100D | H101 | H102 | H103 | H104 | H105 | H106 | H107 |
| H | D | S | P | H | N | A | S | W | G | Q | G | T |
| 105 | 106 | 107 | 108 | 109 | 110 | 111 | 112 | 113 | 114 | 115 | 116 | 117 |
| H108 | H109 | H110 | H111 | H112 | H113 | | | | | | | |
| Q | V | T | V | S | S | | | | | | | |
| 118 | 119 | 120 | 121 | 122 | 123 | | | | | | | |

The Kabat Numbering System Applied to ID-38F (SEQ ID NO: 8), a TNF-Alpha Binding Polypeptide:

| | | | | | | | | | | | |
|---|---|---|---|---|---|---|---|---|---|---|---|
| | 1 | 2 | 3 | 4 | 5 | 6 | 7 | 8 | 9 | 10 | 11 |
| ID38F | D | V | Q | L | V | E | S | G | G | G | L |
| | H1 | H2 | H3 | H4 | H5 | H6 | H7 | H8 | H9 | H10 | H11 |
| | 12 | 13 | 14 | 15 | 16 | 17 | 18 | 19 | 20 | 21 | |
| | V | Q | P | G | G | S | L | K | L | S | |
| | H12 | H13 | H14 | H15 | H16 | H17 | H18 | H19 | H20 | H21 | |
| | | | | | | | | | | CDR1 | |
| | 22 | 23 | 24 | 25 | 26 | 27 | 28 | 29 | 30 | 31 | 32 |
| | C | A | A | S | G | F | D | F | S | S | H |
| | H22 | H23 | H24 | H25 | H26 | H27 | H28 | H29 | H30 | H31 | H32 |
| | CDR1 | | | | | | | | | | |
| | 33 | 34 | 35 | 36 | 37 | 38 | 39 | 40 | 41 | 42 | |
| | W | M | Y | W | V | R | Q | A | P | G | |
| | H33 | H34 | H35 | H36 | H37 | H38 | H39 | H40 | H41 | H42 | |
| | | | | | | | | CDR2 | | | |
| | 43 | 44 | 45 | 46 | 47 | 48 | 49 | 50 | 51 | 52 | 53 |
| | K | E | L | E | W | L | S | E | I | N | T |
| | H43 | H44 | H45 | H46 | H47 | H48 | H49 | H50 | H51 | H52 | H52A |
| | CDR2 | | | | | | | | | | |
| | 54 | 55 | 56 | 57 | 58 | 59 | 60 | 61 | 62 | 63 | |
| | N | G | L | I | T | H | Y | G | D | S | |
| | H53 | H54 | H55 | H56 | H57 | H58 | H59 | H60 | H61 | H62 | |

-continued

| CDR2 | | | | | | | | | | |
|---|---|---|---|---|---|---|---|---|---|---|
| 64 | 65 | 66 | 67 | 68 | 69 | 70 | 71 | 72 | 73 | 74 |
| V | K | G | R | F | T | V | S | R | N | N |
| H63 | H64 | H65 | H66 | H67 | H68 | H69 | H70 | H71 | H72 | H73 |
| 75 | 76 | 77 | 78 | 79 | 80 | 81 | 82 | 83 | 84 | |
| A | A | N | K | M | Y | L | E | L | T | |
| H74 | H75 | H76 | H77 | H78 | H79 | H80 | H81 | H82 | H82A | |
| 85 | 86 | 87 | 88 | 89 | 90 | 91 | 92 | 93 | 94 | 95 |
| R | L | E | P | E | D | T | A | L | Y | Y |
| H82B | H82C | H83 | H84 | H85 | H86 | H87 | H88 | H89 | H90 | H91 |

| CDR3 | | | | | | | | | |
|---|---|---|---|---|---|---|---|---|---|
| 96 | 97 | 98 | 99 | 100 | 101 | 102 | 103 | 104 | 105 |
| C | A | R | N | Q | H | G | L | N | K |
| H92 | H93 | H94 | H95 | H96 | H97 | H98 | H101 | H102 | H103 |
| 106 | 107 | 108 | 109 | 110 | 111 | 112 | 113 | 114 | 115 |
| G | Q | G | T | Q | V | T | V | S | S |
| H104 | H105 | H106 | H107 | H108 | H109 | H110 | H111 | H112 | H113 |

Numbering in the ID-38F figure above with the prefix 'H' is Kabat numbering, while numbering above the amino acid sequence is numbering of amino acids consecutively from N- to C-terminus. The residues of each CDR or FR can also be numbered from the N- to the C-terminus of that CDR or FR.

Features of the polynucleotide sequences disclosed herein are as follows:

| Sequence identifier number and encoded polypeptide | DNA base | | | |
|---|---|---|---|---|
| | Start signal sequence (ATG) | Start encoded binding polypeptide (GAT) | End of encoded binding polypeptide (A of TCA) | Stop codon |
| 25, ID9K and export signal sequence | 33 | 288 | 1034 | 1035-7 |
| 26, ID10K and export signal sequence | 33 | 288 | 1034 | 1035-7 |
| 27, ID11K and export signal sequence | 33 | 288 | 1091 | 1092-4 |
| 28, ID12K and export signal sequence | 33 | 288 | 1091 | 1092-4 |
| 29, ID13K and export signal sequence | 33 | 288 | 1031 | 1032-4 |
| 30, ID14K and export signal sequence | 33 | 288 | 1061 | 1062-4 |
| 17, ID-38F | 82 | 337 | 681 | 682-4 |
| 18, ID-142V | 42 | 297 | 665 | 666-8 |

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

TNF-Alpha Binding Polypeptides
Functional Properties

An anti-TNF-alpha polypeptide, a polypeptide which interacts with TNF-alpha, or a polypeptide against TNF-alpha, are all effectively TNF-alpha binding polypeptides. A TNF-alpha binding polypeptide may bind to a linear or conformational epitope on TNF-alpha. Suitably the TNF-alpha binding polypeptide binds to human TNF-alpha.

Suitably, the TNF-alpha binding polypeptide binds to TNF-alpha with an equilibrium dissociation constant (Kd) of $10^{-6}$ M or less, more suitably $10^{-7}$ M or less, more suitably $10^{-8}$ M or less and more suitably $10^{-9}$ M or less.

Suitably the affinity of the TNF-alpha binding polypeptide is determined using a dynamically switchable biosurface (e.g. "switchSENSE®", see Knezevic et al 2012).

In one embodiment, the affinity of the TNF-alpha binding polypeptide is established at 25° C. by fusing the TNF-alpha binding polypeptide at its C-terminus to single stranded DNA and coupling the DNA-polypeptide fusion to a gold-electrode coated in the fluorescently-labelled complementary strand of single-stranded DNA, before exposing the chip-bound TNF-alpha binding polypeptide to a 10 kHz electrical current and human TNF-alpha at five different concentrations between 50 pM and 4.5 nM for 600 seconds and observing dissociation for 8 hours by time resolved fluorescence.

Suitably the TNF-alpha binding polypeptide neutralises TNF-alpha. A TNF-alpha-neutralising polypeptide is a polypeptide which defends a cell from the effects of TNF-alpha by, for example, inhibiting the biological effect of TNF-alpha. Conventionally, anti-TNF-alpha therapeutic antibody products have used an L929 murine cell line with a cell death endpoint as a neutralisation assay (Humphreys and Wilson 1999). An L929 assay can be performed (as demonstrated in Example 1) to assay the ability of a TNF-alpha binding polypeptide to neutralise the effects of TNF-alpha cytotoxicity by ascertaining the half maximal effective concentration (EC50) of the TNF-alpha binding polypeptide. A detailed protocol for the L929 assay is provided below.

L929 Assay

L929 cells (10000 cells/well) are cultured for 24 h in the presence of soluble TNF-alpha (500 pg/ml) and actinomycin (0.75 ug/mL) together with dilutions of the purified polypeptides. At the end of the experiment cytotoxicity is determined using resazurin. The inhibition of soluble human TNF-induced cytotoxicity of mouse L929 cells is tested to determine TNF-alpha neutralising activity of each of polypeptides against human TNF-alpha.

Materials

L929 cells (10000 cells/well)
Sterile polypropylene 96-well plates
DMEM

Human TNF-alpha concentration: 500 pg/ml
Actinomycin D concentration: 0.75 ug/mL
Purified test polypeptide
Range of dilutions of the purified polypeptide (for example): 300 nM-5 pM (1:3 dilutions)
Human TNF-alpha dose-response curves: 10 ng/mL-0.5 pg/mL
incubation times: 22 h
Resazurin cell viability reagent Method 10000 cells/well in 100 ul are plated on day 0 in 96 wells micro-plates in DMEM complete medium and stored over night at 37 degrees C. and 5% $CO_2$. On day 1 serial dilutions 1:3 (in DMEM+Act.D+TNF) for each purified variable domain are set up (with volumes sufficient for triplicates for each point) starting from a top concentration of 300 nM.

The following controls are added to the plates:
1. DMEM complete+0.75 ug/mL Actinomycin D
2. DMEM complete+0.75 ug/mL Actinomycin D+0.5 ng/mL of h-TNF-alpha
3. DMEM complete+0.01% Triton (only in the plate containing the TNF-alpha dose responses)
4. DMEM complete (only in the plates containing the TNF-alpha dose responses)

The medium is removed from each well of the microplates and the cells are incubated with 100 ul of each polypeptide dilution or with 100 ul of the different controls. After 22 h of incubation at 37 degrees C. and 5% $CO_2$, 10 ul of resazurin is added to each well and the cells are incubated for 2 h at 37 degrees C. 50 ul of 3% SDS is subsequently added to each well. The plates are then read using a fluorescent plate reader Ex544 nm/Em590 nm.

Suitably the TNF-alpha binding polypeptide neutralizes human TNF-alpha cytotoxicity in the L929 assay with an EC50 of 100 nM or less, such as 50 nM or less, such as 10 nM or less, such as 5 mM or less, such as 1 nM or less, such as 0.9 nM or less, such as 0.8 nM or less, such as 0.7 nM or less, such as 0.6 nM or less, such as 0.5 nM or less, such as 0.4 nM or less, such as 0.3 nM or less, such as 0.2 nM or less, such as 0.15 nM or less.

The neutralising ability of a TNF-alpha binding polypeptide may also be ascertained by ELISA. Suitably, the TNF-alpha binding polypeptide inhibits binding of human TNF-alpha to TNFR1 in an ELISA assay with an EC50 of 30 nM or less, more suitably 10 nM or less, more suitably 3 nM or less, more suitably 1 nM or less, more suitably 0.6 nM or less, more suitably 0.5 nM or less, more suitably 0.4 nM or less.

Alternatively or in addition, the TNF-alpha binding polypeptide inhibits binding of human TNF-alpha to TNFR2 in an ELISA assay with an EC50 of 2 nM or less, more suitably 1 nM or less, more suitably 0.9 nM or less, more suitably 0.8 nM or less, more suitably 0.7 nM or less, more suitably 0.6 nM or less, more suitably 0.5 nM or less, more suitably 0.4 nM or less.

Structural Properties

Suitably the TNF-alpha binding polypeptide is a polypeptide comprising an antibody fragment. The polypeptide may be an antibody. Suitably the antibody fragment is selected from the group consisting of: V-NARs, scFvs, Fab fragments, F(ab')2 fragments or immunoglobulin chain variable domains such as VLs, VHHs and VHs. More suitably the antibody fragment is an immunoglobulin chain variable domain, more suitably a VHH or VH, most suitably a VHH.

Suitably the TNF-alpha binding polypeptide comprises three CDRs (CDR1, CDR2 and CDR3).

Suitably CDR1 of the TNF-alpha binding polypeptide comprises or more suitably consists of a sequence sharing 20% or greater, more suitably 40% or greater, more suitably 60% or greater, more suitably 80% or greater sequence identity with SEQ ID NO: 1.

Alternatively, CDR1 of the TNF-alpha binding polypeptide comprises or more suitably consists of a sequence having no more than 3, more suitably no more than 2, more suitably no more than 1 addition(s), substitution(s) and/or deletion(s) compared to SEQ ID NO: 1.

Suitably any residues of CDR1 of the TNF-alpha binding polypeptide differing from their corresponding residues in SEQ ID NO: 1 are conservative substitutions with respect to their corresponding residues. Suitably CDR1 comprises or more suitably consists of SEQ ID NO: 1.

Suitably CDR2 of the TNF-alpha binding polypeptide comprises or more suitably consists of a sequence sharing 20% or greater, more suitably 30% or greater, more suitably 40% or greater, more suitably 50% or greater, more suitably 55% or greater, more suitably 60% or greater, more suitably 70% or greater, more suitably 75% or greater, more suitably 80% or greater, more suitably 85% or greater, more suitably 90% or greater sequence identity, with SEQ ID NO: 2.

Alternatively, CDR2 of the TNF-alpha binding polypeptide comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s), substitution(s) and/or deletion(s) compared to SEQ ID NO: 2.

Suitably any residues of CDR2 of the TNF-alpha binding polypeptide differing from their corresponding residues in SEQ ID NO: 2 are conservative substitutions with respect to their corresponding residues. Suitably the residue of CDR2 of the TNF-alpha binding polypeptide corresponding to residue number 10 of SEQ ID NO: 2 is R, H, D, E, N, Q, S, T, Y, G, A, V, L, W, P, M, C, F or I (most suitably H). Suitably CDR2 of the TNF-alpha binding polypeptide comprises or more suitably consists of SEQ ID NO: 2.

Suitably CDR3 of the TNF-alpha binding polypeptide comprises or more suitably consists of a sequence sharing 30%, more suitably 50%, more suitably 60%, more suitably 80% or greater sequence identity with SEQ ID NO: 3.

Alternatively, CDR3 of the TNF-alpha binding polypeptide comprises or more suitably consists of a sequence having no more than 3, more suitably no more than 2, more suitably no more than 1 addition(s), substitution(s) and/or deletion(s) compared to SEQ ID NO: 3.

Suitably any residues of CDR3 of the TNF-alpha binding polypeptide differing from their corresponding residues in SEQ ID NO: 3 are conservative substitutions with respect to their corresponding residues. Suitably the residue of CDR3 of the TNF-alpha binding polypeptide corresponding to residue number 3 of SEQ ID NO: 3 is R, H, D, E, N, Q, S, T, Y, G, A, V, L, W, P, M, C, F or I; or suitably R, H, D, E, N, Q, S, T, Y, G, V, L, W, P, M, C, F or I (most suitably H). Suitably the residue of CDR3 of the TNF-alpha binding polypeptide corresponding to residue number 3 of SEQ ID NO: 3 is H and any other residues of CDR3 of the TNF-alpha binding polypeptide differing from their corresponding residues in SEQ ID NO: 3 are conservative substitutions with respect to their corresponding residues. Suitably CDR3 of the TNF-alpha binding polypeptide comprises or more suitably consists of SEQ ID NO: 3.

Alternatively CDR3 of the TNF-alpha binding polypeptide comprises or more suitably consists of a sequence sharing 30%, such as 50%, such as 60%, such as 80% or greater sequence identity with SEQ ID NO: 3 and residue number 3 of CDR3 is R, D, N, C, E, Q, G, H, I, L, K, M, F, P, S, T, W, Y or V (suitably H or a conservative substitution of H; more suitably H). Alternatively residue number 3 of CDR3 is H or a conservative substitution of H (most suitably H) and any other residues of CDR3 differing from their corresponding residues in SEQ ID NO: 3 are conservative substitutions.

Suitably residue 1 of CDR1 of the TNF-alpha binding polypeptide is S, V or N; residues 2 to 4 are HWM and residue 5 is Y or C. Suitably, residues 1 to 9 of CDR2 of the TNF-alpha binding polypeptide are EINTNGLIT; residue 10 is H, K, S or N; residue 11 is Y, residue 12 is G, V, I or A; residue 13 is D; residue 14 is S or F; residue 15 is V or T; residue 16 is H, K, R or G and residue 17 is G. Suitably residue 1 of CDR3 of the TNF-alpha binding polypeptide is N; residue 2 is Q or E; residue 3 is H, K, M or R and residues 4 to 6 are GLN.

Suitably the TNF-alpha binding polypeptide comprises three CDRs (CDR1, CDR2 and CDR3) and four framework regions (FR1-FR4).

Suitably FR1 of the TNF-alpha binding polypeptide comprises or more suitably consists of a sequence sharing 5%, 12%, 18%, 26%, 32%, 38%, 46%, 52%, 58%, 62%, 66%, 68%, 72%, 75%, 78%, 82%, 85%, 90% or 95% or greater sequence identity, with SEQ ID NO: 4.

Suitably any residues of FR1 of the TNF-alpha binding polypeptide differing from their corresponding residues in SEQ ID NO: 4 are conservative substitutions with respect to their corresponding residues. Suitably the residue of FR1 of the TNF-alpha binding polypeptide corresponding to residue number 1 of SEQ ID NO: 4 is G, A, V, L, I, F, P, S, T, Y, C, M, K, R, H, W, D, E or N (more suitably D or E, most suitably D). Suitably the residue of FR1 of the TNF-alpha binding polypeptide corresponding to residue number 5 of SEQ ID NO: 4 is G, A, V, L, I, F, P, S, T, Y, C, M, K, R, H, W, D, E or N (suitably V). Suitably the residues of FR1 of the TNF-alpha binding polypeptide corresponding to residue numbers 1 to 5 of SEQ ID NO: 4 are DVQLV. Suitably the residue of FR1 of the TNF-alpha binding polypeptide corresponding to residue numbers 20 and/or 24 of SEQ ID NO: 4 are an amino acid which is hydrophobic (most suitably L or A, respectively). Suitably the residue of FR1 of the TNF-alpha binding polypeptide corresponding to residue number 29 of SEQ ID NO: 4 is F. Suitably FR1 of the TNF-alpha binding polypeptide comprises or more suitably consists of SEQ ID NO: 4.

Suitably FR2 of the TNF-alpha binding polypeptide comprises or more suitably consists of a sequence sharing 10%, 15%, 25%, 30%, 40%, 45%, 55%, 60%, 70%, 75%, 85% or 90% or greater sequence identity, with SEQ ID NO: 5.

Suitably any residues of FR2 of the TNF-alpha binding polypeptide differing from their corresponding residues in SEQ ID NO: 5 are conservative substitutions with respect to their corresponding residues. Suitably the residues of FR2 of the TNF-alpha binding polypeptide corresponding to residue numbers 8 to 11 of SEQ ID NO: 5 are KEXE, wherein X is R or L. Alternatively the residues of FR2 of the TNF-alpha binding polypeptide corresponding to residue numbers 9 to 12 of SEQ ID NO: 5 are GLEW. Suitably FR2 of the TNF-alpha binding polypeptide comprises or more suitably consists of SEQ ID NO: 5.

Suitably FR3 of the TNF-alpha binding polypeptide comprises or more suitably consists of a sequence sharing 8%, 15%, 20%, 26%, 32%, 40%, 45%, 52%, 58%, 65%, 70%, 76%, 80%, 82%, 85%, 90%, 92% or 95% or greater sequence identity, with SEQ ID NO: 6.

Suitably the residue of FR3 of the TNF-alpha binding polypeptide corresponding to residue number 26 of SEQ ID NO: 6 is an amino acid which is hydrophobic (suitably A). Suitably any residues of FR3 of the TNF-alpha binding polypeptide differing from their corresponding residues in SEQ ID NO: 6 are conservative substitutions with respect to their corresponding residues. Suitably FR3 of the TNF-alpha binding polypeptide comprises or more suitably consists of SEQ ID NO: 6.

Suitably FR4 of the TNF-alpha binding polypeptide comprises or more suitably consists of a sequence sharing 5%, 10%, 20%, 30%, 40%, 50%, 60%, 70%, 80% or 90% or greater sequence identity, with SEQ ID NO: 7.

Suitably any residues of FR4 of the TNF-alpha binding polypeptide differing from their corresponding residues in SEQ ID NO: 7 are conservative substitutions with respect to their corresponding residues. Suitably FR4 of the TNF-alpha binding polypeptide comprises or more suitably consists of SEQ ID NO: 7.

Suitably the TNF-alpha binding polypeptide comprises or more suitably consists of a sequence sharing 50%, 55%, 60%, 65%, 70%, 75%, 80%, 85%, 90%, 95%, 96%, 97%, 98% or 99% or greater sequence identity, with SEQ ID NO: 8. Suitably the N-terminus of the TNF-alpha binding polypeptide is D. Suitably the TNF-alpha binding polypeptide comprises or more suitably consists of SEQ ID NO: 8.

According to a specific embodiment, the TNF-alpha binding polypeptide has an amino acid sequence which is not exactly the same as (i.e. shares 100% sequence identity with) the amino acid sequence of a naturally occurring polypeptide.

IL-6R Binding Polypeptides

Functional Properties

An anti-IL-6R polypeptide, a polypeptide which interacts with IL-6R, or a polypeptide against IL-6R, are all effectively IL-6R binding polypeptides. An IL-6R binding polypeptide may bind to a linear or conformational epitope on IL-6R. The term “binds to IL-6R” means binding to IL-6R wherein, for example, IL-6R may be comprised within the IL-6 receptor complex wherein the IL-6R receptor comprises gp130 and/or IL-6.

Suitably, the IL-6R binding polypeptide will bind to both soluble and membrane IL-6R and more suitably with higher affinity to soluble IL-6R than membrane IL-6R. Suitably, the IL-6R binding polypeptide will bind to human IL-6R.

Suitably the IL-6R binding polypeptide is directed against epitopes on IL-6R (and in particular epitopes on IL-6R which are exposed when IL-6R is comprised in an IL-6/IL-6R complex) that lie in and/or form part of the gp130-binding site(s) of the IL-6/IL-6R complex, such that said polypeptide, upon binding to IL-6R, results in inhibiting or reducing signalling mediated by the IL-6/IL-6R complex via gp130 association.

Suitably, the IL-6R binding polypeptide binds to IL-6R with an equilibrium dissociation constant (Kd) of $10^{-6}$ M or less, more suitably $10^{-7}$ M or less, more suitably $10^{-8}$ M or less and more suitably $10^{-9}$ M or less.

Suitably, the affinity of the IL-6R binding polypeptide is determined by surface plasmon resonance.

In one embodiment, the affinity of the IL-6R-binding polypeptide is established at 25° C. by amine coupling human IL-6R at 10 ug/mL in a pH 5, 10 mM Sodium acetate buffer to a sensor chip, before exposing the IL-6R binding peptide at five different concentrations between 100 nM and 500 nM in pH 7.4, 0.01 M HEPES, 0.15 M NaCl, 0.05% polysorbate 20 and 3 mM EDTA buffer and a flow rate of 45 uL/min to the chip-bound IL-6R for 3 mins and then observing dissociation for 10 mins by surface plasmon resonance, wherein the bound-IL-6R is regenerated between cycles with 10 mM Glycine, pH 1.5 for 30 seconds.

Suitably the IL-6R binding polypeptide neutralises IL-6R. A neutralising polypeptide for the purposes of the invention is a polypeptide which interferes in the binding of a sIL-6/IL-6R complex to gp130 as measured by ELISA. Alternatively, or in addition, a neutralising polypeptide for the purposes of the invention is a polypeptide which reduces the proliferation of cells presenting surface IL-6R (such as TF-1 cells) which are exposed to exogenous IL-6, by preventing formation of IL-6/IL-6R/gp130 cis-signalling complexes.

Methods for determining the neutralising capability of an IL-6R binding polypeptide are as follows.

1. Standard QP130 ELISA Assay

A method for determining the potency of an anti-IL-6R polypeptide in neutralising IL-6R is as follows.

The objective of this assay is to measure the potency of anti-IL-6R polypeptides by measuring interference in the binding to gp130 of a sIL-6/IL-6R complex. This assay detects binding of hIL-6R/hIL-6 complexes to recombinant human gp130. This interaction can be competitively inhibited by anti-IL-6R polypeptides, causing reduced binding of hIL-6R-hIL-6 complexes to gp130. Therefore, high signal in this ELISA represents a low concentration or low affinity of anti-IL-6R polypeptide, and vice versa. The details below refer to ICVDs but are equally applicable to any IL-6R binding polypeptide.

Materials

Solutions required:

1×PBS

PBST (1×PBS, 0.05% Tween 20)

Block buffer (1% BSA in 1×PBS, pH 7.3-7.5)

0.5 M Sulphuric acid ($H_2SO_4$)

Reagents required:

Recombinant soluble human gp130 at known concentration

ICVD stock of known concentration

Recombinant soluble human IL-6 at known concentration

Recombinant soluble human IL-6R at known concentration

Biotinylated goat anti-IL-6R polyclonal antibody (R&D systems BAF227); resuspended at 250 ug/ml in sterile PBS.

ExtrAvidin-Peroxidase (Sigma E2886)

TMB substrate (Microwell Peroxidase substrate System 2-C, KPL, 50-70-00)

Procedure

Preparation:

1. Determine number of plates required for the assay.
2. Prepare the relevant volume (up to 3 plates at a time) of 0.2 pg/ml recombinant soluble human gp130 in PBS with 5 ug/mL BSA in 1×PBS.
3. Working quickly, dispense 50 µl/well into Maxisorp 96-well ELISA plates (Nunc), loading a maximum of 3 plates in one batch.
4. Shake plate briefly, seal and incubate at 4° C. overnight.

Assay:

1. Wash the ELISA plate using a plate washer (4×~380 µl PBST). Bang the plate on towel to remove residual liquid.
2. Apply 200 µl/well block buffer. Seal and incubate on a rotary plate shaker for >1 hour.
3. Prepare a dilution series of ICVD standards between 0.004 nM to 80 nM in minimum final volumes of 70 µl using block buffer as a diluent.
4. Prepare appropriate dilutions of samples to be tested in block buffer, such that their estimated final concentration on the plate will fall in the range of 0.001 nM to 250 nM ICVD.
5. Prepare a 40 ng/ml IL-6R solution in block buffer.
6. In a separate 96-well plate, mix together 50 µl of each ICVD dilution with 50 µl IL-6R solution. In each dilution series include one well with no ICVD. Incubate for 1 hour on a rotary plate shaker.
7. Prepare a 100 ng/ml IL-6 solution in block buffer.
8. In a further additional 96-well plate, mix together 85 µl ICVD-IL-6R mixture from step 6 with 85 µl IL-6 solution prepared in step 7. Include wells containing block buffer only, such that the following controls are applied to each plate: IL-6 only, and no ICVD (IL6+IL6R only). Incubate for 10 minutes on rotary plate shaker.
9. Wash blocked ELISA plate as in step 1.
10. Transfer 50 µl of the mixtures prepared in step 8 to the washed ELISA plate in triplicate. Seal and incubate on a rotary plate shaker for 2 hours.
11. Wash blocked ELISA plate as in step 1.
12. Prepare 5.2 ml/plate 125 ug/mL of BAF227 anti-hIL-6R antibody made up in block buffer. Add 50 µl/well, seal, shake briefly, and incubate for 1 hour at room temperature or overnight at 4° C.
13. Wash blocked ELISA plate as in step 1.
14. Prepare 5.2 ml/plate of 1/1,000-1/3000 dilution of Extravidin in block buffer. Add 50 µl/well, seal, and incubate on a rotary shaker for 30 mins.
15. Wash blocked ELISA plate as in step 1.
16. Prepare 10 ml/plate TMB substrate (1:1 ratio of substrate A and B). Add 100 µl/well, seal and incubate on a rotary plate shaker until a mid blue colour evolves in the lowest dilution wells or up to a maximum of 30 mins. Shield from light.
17. Stop reaction with 50 µl/well 0.5 M $H_2SO_4$.
18. Read plate at 450 nm.
19. Use standard curve to interpolate concentrations of active ICVD. Raw OD450 values are adjusted with readings taken from blank control wells. Standard curves are plotted using appropriate software (e.g. Graphpad Prism using Log(inhibitor) vs. response—variable slope (four parameters)). ICVD concentrations in the test samples are calculated in the software using the standard curve.

2. The standard TF1 cell assay

A method for determining the potency of an anti-IL-6R agent in inhibiting membrane bound IL-6R mediated IL-6 cis-signalling is as follows. This assay detects the activity of exogenous IL-6 on TF1 cell proliferation. TF1 cells are a human erythroblast immortal cell line that expresses the membrane-bound IL-6 receptor on their surface. In the presence of exogenously added IL-6, the cells are stimulated via the IL-6 cis-signalling pathway to proliferate. Anti-membrane-bound IL-6R compounds prevent the formation of the complete IL-6/IL-6R/gp130 complex that is required for signalling, reducing IL-6-stimulated proliferation in dose-dependent manner. Cell proliferation is measured after two days using resazurin, a blue dye that is irreversibly reduced to the pink coloured and highly red fluorescent resorufin by cellular metabolic processes. Details below refer to ICVDs or antibodies but are equally applicable to any IL-6R binding polypeptide.

Materials

Standard components:

Cell line: TF-1 (Public Health England, Cat. No. 93022307). Exponentially growing cells (<5×10^5 cells/mL) cultivated in Advanced RPMI with 5% heat-inactivated foetal bovine serum and 2.5 ng/mL GM-CSF (Human Granulocyte Macrophage Colony Stimulating Factor).
Assay medium: Advanced RMPI (LifeTech 12633-012) with 2 mM L-glutamine, Pen/Strep
1×PBS
3% SDS
Sterile MQ water
Sterile 96 well micro-titre plates for cell culture, flat bottomed, optically clear
12 multi-channel pipette and filtered tips
Reagents:
Recombinant soluble human IL-6 at known concentration
Anti-IL-6R antibodies or ICVD of known concentration
Resazurin (Alamar Blue; LifeTech, DAL1100)
Procedure
Cell Preparation:
  a. Pre-warm media and 1×PBS in a 37° C. water bath.
  b. Determine the number of plates required for the assay.
  c. Fill the outside wells with 320 uL of sterile MilliQ water.
  d. Fill the spaces between the wells with 160 uL of the same water.
  e. Calculate the volume of the cell culture you will need to have 20,000 cells/well using the equation:

$$\frac{(60 \text{ wells per plate} \times \# \text{ plates} \times 20{,}000 \text{ cells/well} \times 1.2 \text{ (for 20\% overage)})}{\text{Cell count (cells/ml)}} = \text{total cells}$$

f. Transfer cells to falcon tube. Take to maximum tube volume with 1×PBS. Spin 5' at 1.1 k×rpm at 20 degrees C.
  g. Remove medium from cell pellet with a 10 mL stripette, leave ~200 uL on the cells, ensuring no cells are aspirated. Tap cells in residual volume to resuspend.
  h. Wash cells in full tube volume of 1×PBS spin as before.
  i. Remove 1×PBS with a 10 mL stripette, leave ~200 uL on the cells, ensuring no cells are aspirated. Remove residual with P200.
  j. Resuspend cell pellet by tapping then add assay medium using the equation below to calculate the volume required:

60 wells per plate×#plates×0.05 mL volume per well×1.2 (for 20% overage)=total volume k. Fill plates with 50 ul cells per well proceeding row by row. Place filled plates in the incubator. Agitate the cells by pipetting or shaking the trough intermittently during this process.
ICVD/Antibody Preparation:
  a. Prepare the assay stock of IL-6 at 20 ng/mL (4× the assay concentration) in a volume of assay medium sufficient to add 25 ul per well.
  b. Prepare a 9 point serial dilution series of ICVD reference standards at 4× the assay concentration (being between 0.04 nM and 2500 nM in minimum final volumes of 100 µl using assay medium as a diluent. In a tenth well, add assay medium only. For example, starting in well A1 make the dilutions series along to plate to well A9. In well A10, add medium only.
  c. In a fresh microtitre plate, add a minimum volume of 85 uL of IL-6 to the equivalent 9 wells used in the dilution series. In the tenth well add either assay medium or IL-6 to the effect that each final assay plate will have wells with IL-6 only (maximum proliferation) and media only (minimum proliferation).
  d. To the IL-6 mix plate prepared above, add an equivalent volume (e.g. 85 uL) of each ICVD/antibody serial dilution. At this stage both IL-6 and ICVD will be at 2× the assay concentration.
Assay:
  a. Mix the ICVD/Antibody & IL-6 mixtures by pipetting and add 50 ul of each mix to the cells.
  b. Incubate the cells for 2 days at 37° C., 5% $CO_2$.
  c. Add 10 uL of AlamarBlue to cells. Protect from light.
  d. Shake the cells gently for 30 s on a plate shaker to mix
  e. Incubate 37° C., 5% $CO_2$ for 2 hours.
  f. Stop cellular processes with 50 uL 3% SDS. Protect from light
  g. Read on plate reader (e.g. BMG Fluorstar) at Ex 544 nm-Em 590 nm
  h. Use calibration curve to interpolate unknown sample concentrations. Raw OD450 values are adjusted with readings taken from blank control wells. Standard curves are plotted using appropriate software (e.g. Graphpad Prism using Log(inhibitor) vs. response—variable slope (four parameters)). ICVD concentrations in the test samples are calculated in the software using the standard curve.

The M1 Cell Assay

The M1 cell assay may be used to investigate the IL-6 trans-signalling neutralising potency of polypeptides specific for IL-6R. M1 cells respond to exogenous IL-6+IL-6R by inhibition of proliferation, by differentiation and eventually cell death, but this response can be negated by IL-6R specific polypeptides that prevent IL-6R-IL-6 binding. The discussion below refers to ICVDs but is equally applicable to any IL-6R binding polypeptide.

The M1 assay measures the effect, in terms of cell behaviour, of ICVD blockade of IL-6 trans-signalling over a period of days. In assessment of ICVD trans selectivity, the TF-1 cell assay is used to measure cis IL-6 signalling; it is therefore appropriate when determining the degree of trans vs cis selectivity, to use data from another cellular assay, dependent on IL-6 trans signalling, such as the M1 cell assay, for comparison. Details are provided in respect of ICVDs but these methods are equally applicable to any IL-6R binding polypeptide.

M1 cells from a rapidly growing stock culture are inoculated into 96-well assay plates in RPMI medium+3% FCS at $5 \times 10^4$ cells/50 µl/well. IL-6, IL-6R and concentration ranges of ICVDs are all prepared in the same medium at 6×the final assay concentration (20 ng/ml IL-6R, 100 ng/ml IL-6). 75 µl of each ICVD dilution is mixed with the same volume of 120 ng/ml IL-6R and incubated for 1 hour at room temperature, before addition of 75 µl of 600 ng/ml IL-6 to each of these mixtures. Finally, 50 µl of each ICVD/IL-6R/IL-6 mixture is added to four replicate wells of M1 cells, and the plates incubated undisturbed for 5 days. Viable cell mass is then measured by Alamar blue addition (10 µl/well), further incubated for 5 hours, and finally 50 µl 3% SDS solution is added, and fluorescence measured at 620 nm. IL-6 only and IL-6+IL-6R only controls represent 0% and 100% of the IL-6+IL-6R stimulated response.

Suitably the IL-6R binding polypeptide neutralizes sIL-6R-IL-6 binding to gp130 in an ELISA assay such as the standard gp130 ELISA with an EC50 of 100 nM or less, such as 75 nM or less, such as 50 nM or less, such as 40 nM or less, such as 30 nM or less, such as 25 nM or less, such as 20 nM or less, such as 10 nM or less, such as 5 nM or less, such as 2 nM or less, such as 1.5 nM or less, such as 1 nM or less, such as 0.9 nM or less, such as 0.8 nM or less, such as 0.7 nM or less, such as 0.6 nM or less, such as 0.5 nM or less.

Suitably the IL-6R binding polypeptide prevents proliferation of TF-1 cells in the standard TF-1 assay with an EC50 of 20 nM or less, such as 15 nM or less, such as 10 nM or less, such as 6 nM or less, such as 5 nM or less, such as 4.5 nM or less.

Suitably the IL-6R binding polypeptide prevents proliferation of M1 cells in the M1 cell assay with an $EC_{50}$ of 20 nM or less, such as 15 nM or less, such as 10 nM or less, such as 6 nM or less, such as 5 nM or less, such as 4.5 nM or less.

Suitably the IL-6R binding polypeptide inhibits IL-6R trans-signalling to a higher extent than it inhibits IL-6R cis-signalling, i.e. the polypeptide is 'trans-selective'.

Structural Properties

Suitably the IL-6R binding polypeptide is a polypeptide comprising an antibody fragment. The polypeptide may be an antibody. Suitably the antibody fragment is selected from the group consisting of: V-NARs, scFvs, Fab fragments, F(ab')2 fragments or immunoglobulin chain variable domains such as VLs, VHHs and VHs. More suitably the antibody fragment is an immunoglobulin chain variable domain, more suitably a VHH or VH, most suitably a VHH.

Suitably the IL-6R binding polypeptide comprises three CDRs (CDR1, CDR2 and CDR3).

Suitably CDR1 of the IL-6R binding polypeptide comprises or more suitably consists of a sequence sharing 20%, 40%, 60%, or 80% or greater sequence identity, with SEQ ID NO: 9.

Alternatively, CDR1 of the polypeptide of the IL-6R binding polypeptide comprises or more suitably consists of a sequence having no more than 4, more suitably no more than 3, more suitably no more than 2, more suitably no more than 1 addition(s), substitution(s) and/or deletion(s) compared to SEQ ID NO: 9.

Suitably any residues of CDR1 of the IL-6R binding polypeptide differing from their corresponding residues in SEQ ID NO: 9 are conservative substitutions with respect to their corresponding residues. Suitably CDR1 of the IL-6R binding polypeptide comprises or more suitably consists of SEQ ID NO: 9.

Suitably CDR2 of the IL-6R binding polypeptide comprises or more suitably consists of a sequence sharing 20% or greater, more suitably 30% or greater, more suitably 40% or greater, more suitably 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater sequence identity, with SEQ ID NO: 10.

Alternatively, CDR2 of the IL-6R binding polypeptide comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s), substitution(s) and/or deletion(s) compared to SEQ ID NO: 10.

Suitably any residues of CDR2 of the IL-6R binding polypeptide differing from their corresponding residues in SEQ ID NO: 10 are conservative substitutions with respect to their corresponding residues. Suitably CDR2 of the IL-6R binding polypeptide comprises or more suitably consists of SEQ ID NO: 10.

Suitably CDR3 of the IL-6R binding polypeptide comprises or more suitably consists of a sequence sharing 20% or greater, more suitably 30% or greater, more suitably 40% or greater, more suitably 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater sequence identity with SEQ ID NO: 11.

Alternatively, CDR3 of the IL-6R binding polypeptide comprises or more suitably consists of a sequence having no more than 6, more suitably no more than 5, more suitably no more than 4, more suitably no more than 3, more suitably no more than 2, more suitably no more than 1 addition(s), substitution(s) and/or deletion(s) compared to SEQ ID NO: 11.

Suitably any residues of CDR3 of the IL-6R binding polypeptide differing from their corresponding residues in SEQ ID NO: 11 are conservative substitutions with respect to their corresponding residues.

Suitably the residue of CDR3 of the IL-6R binding polypeptide corresponding to residue number 5 of SEQ ID NO: 11 is R or H, most suitably H. Suitably the residue of CDR3 of the IL-6R binding polypeptide corresponding to residue number 5 of SEQ ID NO: 11 is R or H, most suitably H, and any other residues of CDR3 of the IL-6R binding polypeptide differing from their corresponding residues in SEQ ID NO: 11 are conservative substitutions with respect to their corresponding residues.

Suitably the residue of CDR3 of the IL-6R binding polypeptide corresponding to residue number 9 of SEQ ID NO: 11 is F, L or H, more suitably F or H, most suitably H. Suitably the residue of CDR3 of the IL-6R binding polypeptide corresponding to residue number 9 of SEQ ID NO: 11 is F, L or H, most suitably H, and any other residues of CDR3 differing from their corresponding residues in SEQ ID NO: 11 are conservative substitutions with respect to their corresponding residues.

Suitably the residue of CDR3 of the IL-6R binding polypeptide corresponding to residue number 11 of SEQ ID NO: 11 is A, G, or a conservative substitution thereof. Suitably the residue of CDR3 of the IL-6R binding polypeptide corresponding to residue number 11 of SEQ ID NO: 11 is A or G, most suitably A. Suitably the residue of CDR3 of the IL-6R binding polypeptide corresponding to residue number 11 of SEQ ID NO: 11 is A or G, most suitably A, and any other residues of CDR3 differing from their corresponding residues in SEQ ID NO: 11 are conservative substitutions with respect to their corresponding residues.

Suitably CDR3 of the IL-6R binding polypeptide comprises or more suitably consists of SEQ ID NO: 11.

Suitably the IL-6R binding polypeptide comprises three CDRs (CDR1, CDR2 and CDR3) and four framework regions (FR1-FR4).

Suitably FR1 of the IL-6R binding polypeptide comprises or more suitably consists of a sequence sharing 5%, 12%, 18%, 26%, 32%, 38%, 46%, 52%, 58%, 62%, 66%, 68%, 72%, 75%, 78%, 82%, 85%, 90% or 95% or greater sequence identity, with SEQ ID NO: 12.

Suitably any residues of FR1 of the IL-6R binding polypeptide differing from their corresponding residues in SEQ ID NO: 12 are conservative substitutions with respect to their corresponding residues.

Suitably the residue of FR1 of the IL-6R binding polypeptide corresponding to residue number 1 of SEQ ID NO: 12 is G, A, V, L, I, F, P, S, T, Y, C, M, K, R, H, W, D, E or N (more suitably D or E, most suitably D). Suitably the residue of FR1 of the IL-6R binding polypeptide corresponding to residue number 23 of SEQ ID NO: 12 is K or L. Suitably the residues of FR1 of the IL-6R binding polypeptide corresponding to residue numbers 2 to 5 of SEQ ID NO: 12 are VQLV. Suitably the residue of FR1 of the IL-6R binding polypeptide corresponding to residue number 29 of SEQ ID NO: 12 is F or S, most suitably S. Suitably the residue of FR1 of the IL-6R binding polypeptide corresponding to residue number 30 of SEQ ID NO: 12 is N or S. Suitably FR1 of the IL-6R binding polypeptide comprises or more suitably consists of SEQ ID NO: 12.

Suitably FR1 of the IL-6R binding polypeptide comprises the sequence NIN or three consecutive amino acids wherein one or more of the amino acids is a conservative substitution of the corresponding amino acid in the sequence NIN. Most suitably FR1 of the IL-6R binding polypeptide comprises the sequence NIN. More suitably the last four C-terminal residues of FR1 of the IL-6R binding polypeptide are NINX or four consecutive amino acids wherein one or more of the amino acids is a conservative substitution of the corresponding amino acid in the sequence NINX, wherein X is any amino acid. Suitably X is S or a conservative substitution of S, most suitably X is S. More suitably FR1 of the IL-6R binding polypeptide consists of 33 residues and the last four residues of FR1 are NINS.

Suitably FR2 of the IL-6R binding polypeptide comprises or more suitably consists of a sequence sharing 10%, 15%, 25%, 30%, 40%, 45%, 55%, 60%, 70%, 75%, 85% or 90% or greater sequence identity, with SEQ ID NO: 13.

Suitably any residues of FR2 of the IL-6R binding polypeptide differing from their corresponding residues in SEQ ID NO: 13 are conservative substitutions with respect to their corresponding residues. Suitably the residue of FR2 of the IL-6R binding polypeptide corresponding to residue number 9 of SEQ ID NO: 13 is G or Q. Suitably the residues of FR2 of the IL-6R binding polypeptide corresponding to residue numbers 8 to 11 of SEQ ID NO: 13 are KERE, KELE, KGRE or KQRE; most suitably KGRE or KQRE. Suitably FR2 of the IL-6R binding polypeptide comprises or more suitably consists of SEQ ID NO: 13.

Suitably FR3 of the IL-6R binding polypeptide comprises or more suitably consists of a sequence sharing 8%, 15%, 20%, 26%, 32%, 40%, 45%, 52%, 58%, 65%, 70%, 76%, 80%, 82%, 85%, 90%, 92% or 95% or greater sequence identity, with SEQ ID NO: 14.

Suitably the residue of FR3 of the IL-6R binding polypeptide corresponding to residue number 8 of SEQ ID NO: 14 is an amino acid which is hydrophobic (suitably A or N, more suitably A). Suitably the residue of FR3 of the IL-6R binding polypeptide corresponding to residue number 9 of SEQ ID NO: 14 is an amino acid which is hydrophobic (suitably A or S, more suitably A). Suitably the residue of FR3 of the IL-6R binding polypeptide corresponding to residue number 13 of SEQ ID NO: 14 is V or L, most suitably V. Suitably the residue of FR3 of the IL-6R binding polypeptide corresponding to residue number 14 of SEQ ID NO: 14 is N or Y, most suitably Y. Suitably the residue of FR3 of the IL-6R binding polypeptide corresponding to residue number 21 of SEQ ID NO: 14 is R or K, most suitably R.

Suitably any residues of FR3 differing from their corresponding residues in SEQ ID NO: 14 are conservative substitutions with respect to their corresponding residues. Suitably FR3 comprises or more suitably consists of SEQ ID NO: 14.

Suitably FR4 of the IL-6R binding polypeptide comprises or more suitably consists of a sequence sharing 5%, 10%, 20%, 30%, 40%, 50%, 60%, 70%, 80% or 90% or greater sequence identity, with SEQ ID NO: 15.

Suitably any residues of FR4 of the IL-6R binding polypeptide differing from their corresponding residues in SEQ ID NO: 15 are conservative substitutions with respect to their corresponding residues. Suitably FR4 of the IL-6R binding polypeptide comprises or more suitably consists of SEQ ID NO: 15.

Suitably the IL-6R binding polypeptide comprises or more suitably consists of a sequence sharing 50%, 55%, 60%, 65%, 70%, 75%, 80%, 85%, 90%, 95%, 96%, 97%, 98% or 99% or greater sequence identity, with SEQ ID NO: 16.

Suitably the N-terminus of the IL-6R binding polypeptide is D. Suitably the IL-6R binding polypeptide comprises or more suitably consists of SEQ ID NO: 16.

According to a specific embodiment, the IL-6R binding polypeptide has an amino acid sequence which is not exactly the same as (i.e. shares 100% sequence identity with) the amino acid sequence of a naturally occurring polypeptide.

Particular combined structural and functional properties of both the TNF-alpha binding polypeptide and the IL-6R binding polypeptide Suitably both the TNF-alpha binding polypeptide and the IL-6R binding polypeptide are immunoglobulin chain variable domains wherein:

(a) CDR1 of the TNF-alpha binding polypeptide comprises a sequence sharing 40% or greater sequence identity with SEQ ID NO: 1;
(b) CDR2 of the TNF-alpha binding polypeptide comprises a sequence sharing 40% or greater sequence identity with SEQ ID NO: 2;
(c) CDR3 of the TNF-alpha binding polypeptide comprises a sequence sharing 50% or greater sequence identity with SEQ ID NO: 3;
(d) CDR1 of the IL-6R binding polypeptide comprises a sequence sharing 40% or greater sequence identity with SEQ ID NO: 9;
(e) CDR2 of the IL-6R binding polypeptide comprises a sequence sharing 40% or greater sequence identity with SEQ ID NO: 10;
(f) CDR3 of the IL-6R binding polypeptide comprises a sequence sharing 50% or greater sequence identity with SEQ ID NO: 11, more suitably wherein:
(a) CDR1 of the TNF-alpha binding polypeptide comprises a sequence sharing 60% or greater sequence identity with SEQ ID NO: 1;
(b) CDR2 of the TNF-alpha binding polypeptide comprises a sequence sharing 50% or greater sequence identity with SEQ ID NO: 2;
(c) CDR3 of the TNF-alpha binding polypeptide comprises a sequence sharing 60% or greater sequence identity with SEQ ID NO: 3;
(d) CDR1 of the IL-6R binding polypeptide comprises a sequence sharing 60% or greater sequence identity with SEQ ID NO: 9;
(e) CDR2 of the IL-6R binding polypeptide comprises a sequence sharing 50% or greater sequence identity with SEQ ID NO: 10;
(f) CDR3 of the IL-6R binding polypeptide comprises a sequence sharing 60% or greater sequence identity with SEQ ID NO: 11, more suitably wherein:
(a) CDR1 of the TNF-alpha binding polypeptide comprises a sequence sharing 60% or greater sequence identity with SEQ ID NO: 1;

(b) CDR2 of the TNF-alpha binding polypeptide comprises a sequence sharing 70% or greater sequence identity with SEQ ID NO: 2;
(c) CDR3 of the TNF-alpha binding polypeptide comprises a sequence sharing 65% or greater sequence identity with SEQ ID NO: 3;
(d) CDR1 of the IL-6R binding polypeptide comprises a sequence sharing 60% or greater sequence identity with SEQ ID NO: 9;
(e) CDR2 of the IL-6R binding polypeptide comprises a sequence sharing 70% or greater sequence identity with SEQ ID NO: 10;
(f) CDR3 of the IL-6R binding polypeptide comprises a sequence sharing 65% or greater sequence identity with SEQ ID NO: 11,
more suitably wherein:
(a) CDR1 of the TNF-alpha binding polypeptide comprises a sequence sharing 80% or greater sequence identity with SEQ ID NO: 1;
(b) CDR2 of the TNF-alpha binding polypeptide comprises a sequence sharing 85% or greater sequence identity with SEQ ID NO: 2;
(c) CDR3 of the TNF-alpha binding polypeptide comprises a sequence sharing 80% or greater sequence identity with SEQ ID NO: 3;
(d) CDR1 of the IL-6R binding polypeptide comprises a sequence sharing 80% or greater sequence identity with SEQ ID NO: 9;
(e) CDR2 of the IL-6R binding polypeptide comprises a sequence sharing 85% or greater sequence identity with SEQ ID NO: 10;
(f) CDR3 of the IL-6R binding polypeptide comprises a sequence sharing 80% or greater sequence identity with SEQ ID NO: 11,
and in each case wherein most suitably the TNF-alpha binding polypeptide neutralizes human TNF-alpha cytotoxicity in the L929 assay with an EC50 of 100 nM or less and the IL-6R binding polypeptide neutralizes sIL-6R-IL-6 binding to gp130 in the standard gp130 ELISA with an EC50 of 100 nM or less; and/or wherein the TNF-alpha binding polypeptide binds to TNF-alpha with a Kd of $10^{-7}$ M or less and the IL-6R binding polypeptide binds to IL-6R with a Kd of $10^{-7}$ M or less.

Format of TNF-Alpha and IL-6R Binding Polypeptides

The TNF-alpha binding polypeptide and the IL-6R binding polypeptide may be linked or unlinked.

In one embodiment, the TNF-alpha binding polypeptide and the IL-6R binding polypeptide may be present in the composition of the invention independently from one another (i.e. the TNF-alpha and IL-6R binding polypeptides are not linked to each other). In a specific embodiment, the composition comprises (a) ID-38F (SEQ ID NO: 8) or a polypeptide having at least 75%, more suitably at least 85% identity thereto and (b) ID-142V (SEQ ID NO: 16) or a polypeptide having at least 75%, more suitably at least 85% identity thereto.

In a further embodiment, the TNF-alpha binding polypeptide and the IL-6R binding polypeptide comprised in the composition of the invention are linked to each other (thereby forming a single construct). Such a format may be convenient for recombinant expression purposes. Such a construct of the invention is therefore multimeric and multivalent. If no further polypeptides are comprised within the construct, then such a construct may be referred to as a 'heterobihead'. A multivalent construct comprises two or more binding polypeptides and therefore provides two or more sites at which attachment to antigens can occur (suitably before or after cleavage of the labile peptide linker, if such a linker is present in the construct—see 'Linkers' below).

A construct of the invention may comprise an additional third polypeptide (connected to the TNF-alpha or IL-6R binding polypeptide directly or by a linker) and may also comprise or consist of an additional fourth polypeptide (connected to the TNF-alpha or IL-6R binding polypeptide directly or by a linker). A construct of the invention consisting of four polypeptides is known as a 'quadrahead'. A quadrahead may for example have the format anti-TNF-alpha-anti-IL-6R-anti-IL-6R-anti-TNF-alpha, anti-TNF-alpha-anti-IL-6R-anti-TNF-alpha-anti-IL-6R or anti-IL-6R-anti-TNF-alpha-anti-TNF-alpha-anti-IL6R. The linkers between these binding polypeptides may be labile or non-labile (see below under 'Linkers'). For example, a quadrahead may for example have the format anti-TNF-alpha-anti-IL-6R-(labile linker)-anti-IL-6R-anti-TNF-alpha, anti-TNF-alpha-(labile linker)-anti-IL-6R-anti-IL-6R-(labile linker)-anti-TNF-alpha or anti-IL-6R-(labile linker)-anti-TNF-alpha-anti-TNF-alpha-(labile linker)-anti-IL-6R.

Suitably each polypeptide in the construct has a molecular weight of no greater than 300 kDa, such as 250 kDa, such as 200 kDa, such as 180 kDa, such as 160 kDa, such as 140 kDa, such as 120 kDa, such as 100 kDa, such as 80 kDa, such as 60 kDa.

Linkers

The TNF-alpha and IL-6R binding polypeptides, if linked, can be linked to each other directly (i.e. without use of a linker) or via a linker. Suitably a linker is used. The linker may be a protease-labile or a non-protease-labile linker. The linker is suitably a peptide and suitably will be selected so as to allow binding of the polypeptides to their epitopes. Suitably the linker is flexible, for example sufficiently flexible to allow both binding polypeptides to bind their targets simultaneously (such as a $[-(G_4S)-]_4$. If used for therapeutic purposes, the linker is suitably non-immunogenic in the subject to which the polypeptides are administered. Suitably the polypeptides and linker are expressed as a single contiguous polypeptide construct.

Suitably the peptide linker has a length of at least 3, such as at least 4, such as at least 5, such as at least 6, such as at least 7, such as at least 8, such as at least 9, such as at least 10 residues. Suitably the peptide linker has a length of no greater than 40, such as no greater than 35, such as no greater than 30, such as no greater than 25, such as no greater than 20, such as no greater than 15 residues.

Suitably the peptide linker consists of any amino acids selected from the list consisting of: arginine, histidine, lysine, aspartic acid, glutamic acid, serine, threonine, asparagine, glutamine, cysteine, glycine, proline, alanine, valine, isoleucine, leucine, methionine, phenylalanine, tyrosine and tryptophan. Proline may be a sub-optimal amino acid for inclusion in a linker and therefore more suitably the peptide linker consists of any amino acids selected from the list consisting of: arginine, histidine, lysine, aspartic acid, glutamic acid, serine, threonine, asparagine, glutamine, cysteine, glycine, alanine, valine, isoleucine, leucine, methionine, phenylalanine, tyrosine and tryptophan.

The TNF-alpha and IL-6R binding polypeptides, if linked, may be in the orientation (from N- to C-terminus) anti-TNF-alpha-linker-anti-IL-6R or may be in the orientation anti-IL6R-linker-anti-TNF-alpha. Most suitably, they are in the orientation anti-TNF-alpha-linker-anti-IL-6R.

Compositions of the invention comprising TNF-alpha and IL-6R binding polypeptides linked by peptide linkers may for example be obtained by preparing a nucleic acid encoding the two binding polypeptides and a peptide linker using techniques for nucleic acid synthesis, followed by expression of the nucleic acid thus obtained (as detailed further under the heading 'preparative methods' below).

Non-protease-labile linkers

Suitably the non-protease-labile linker is a peptide and does not comprise a cleavage site for a protease.

Suitably the non-protease-labile linker is of the format $-(G_aS_b)_x-$ wherein a is 1 to 10, b is 1 to 5 and x is 1 to 15. More suitably a is 1 to 5, b is 1 to 2 and x is 1 to 10. More suitably a is 4, b is 1 and x is 1 to 8.

The TNF-alpha binding polypeptide and the IL-6R binding polypeptide, when linked to each other with a non-protease-labile linker, may be deployed in one of the following formats: anti-TNF-alpha-$(G_4S)_6$-anti-IL-6R (as exemplified by the particular construct ID-11K (residues 87-354 of SEQ ID NO: 21)), anti-IL-6R-$(G_4S)_6$-anti-TNF-alpha (as exemplified by the particular construct ID-12K (residues 87-354 of SEQ ID NO: 22)), anti-TNF-alpha-$(G_4S)_2$-anti-IL-6R (as exemplified by the particular construct ID-13K (residues 87-334 of SEQ ID NO: 23)), anti-TNF-alpha-$(G_4S)_4$-anti-IL-6R (as exemplified by the particular construct ID-14K (residues 87-344 of SEQ ID NO: 24)), anti-IL-6R-$(G_4S)_2$-anti-TNF-alpha or anti-IL-6R-$(G_4S)_4$-anti-TNF-alpha.

Most suitably the TNF-alpha binding polypeptide and the IL-6R binding polypeptide, when linked to each other with a non-protease-labile linker, are deployed in the format anti-TNF-alpha-$(G_4S)_4$-anti-IL-6R (as exemplified by the particular construct ID-11K (residues 87-354 of SEQ ID NO: 21)).

In one embodiment, the construct is selected from the list consisting of ID-11K (residues 87-354 of SEQ ID NO: 21), ID-12K (residues 87-354 of SEQ ID NO: 22), ID-13K (residues 87-334 of SEQ ID NO: 23) and ID-14K (residues 87-344 of SEQ ID NO: 24). More suitably, the construct is ID-11K.

Protease-Labile Linkers

A protease-labile linker (or 'labile peptide linker') is a peptide and comprises at least one cleavage site for a protease. Including a protease-labile linker in a construct of the invention allows, for example, the construct to be conveniently produced in the form of a heterobihead which is then later cleaved after administration into separate binding polypeptides.

In one embodiment of the invention, the labile peptide linker can be engineered such that it resists cleavage by proteases to a desired extent and/or is only cleaved upon exposure to a specific area of the intestinal tract. For example, if a construct is recombinantly produced in a host such as yeast, trypsin-like proteases produced by the yeast may cleave the recombinant construct product. This may result in difficulties in purification and cause regulatory, clinical and commercial complications.

This can be achieved by incorporating shielding residues into the labile peptide linker flanking the labile site(s). Shielding residues flank the labile site(s) of the labile peptide linker and reduce the lability thereof. Cleavage resistance can also be increased by positioning the labile site(s) closer to or at the periphery of the labile peptide linker. This concept is referred to as a "shielded labile site" and provides controlled lability.

The labile peptide linker can alternatively be engineered such that it is highly labile to cleavage by intestinal tract proteases, thereby quickly releasing the constituent polypeptides of the construct after oral administration. This is achieved by incorporating one or more labile sites into the labile peptide linker such that the labile site is exposed for proteolysis, for example by positioning the labile site(s) substantially centrally in the labile peptide linker and/or by the labile site not being shielded substantially by flanking residues. This concept is referred to as a "non-shielded labile site".

Incorporation of a P residue into the labile peptide linker of the construct of the invention immediately following an R or K residue is expected to substantially prevent cleavage of the labile peptide linker. Suitably the labile peptide linker does not comprise any P residues.

Trypsin Labile Sites

Suitably the labile peptide linker comprises a cleavage site for trypsin or a trypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 K residues. Suitably the labile peptide linker comprises at least 1, such as at least 2, such as at least 3, such as at least 4, such as at least 5, such as at least 6, such as at least 7, such as at least 8, such as at least 9, such as at least 10 R residues. Preferably the cleavage site(s) is/are one or more K residue(s).

Non-Shielded Labile Sites

Suitably the protease-labile linker comprises or more suitably consists of the format $[-(G_aS_b)_x-B_t(G_cS_d)_y-]_z$ wherein B is lysine or arginine, t is 1 to 5, a is 0 to 10, b is 0 to 5, x is 0 to 10, c is 0 to 10, d is 0 to 5, y is 0 to 10 and z is 1 to 5. More suitably, B is lysine or arginine, t is 1 to 3, a is 0 to 5, b is 0 to 2, x is 0 to 5, c is 0 to 5, d is 0 to 2, y is 0 to 5 and z is 1 to 3. More suitably, t is 1, a is 3 to 5, b is 1, x is 1 to 2, c is 3 to 5, d is 1, y is 1 to 2 and z is 1.

Suitably the labile peptide linker comprises or more suitably consists of a polypeptide sequence of the format:

wherein
a is 1 to 10;
x is 1 to 10;
B is K or R and
B' is K or R.

In one embodiment, a is 2 to 5, more suitably a is 4. In a further embodiment x is 1 to 5. More suitably, x is 2. B may be present or not present. B' may be present or not present. Suitably, B is K. Suitably, B' is K.

Particularly favoured linkers of this format are selected from one of the list consisting of —K-$(G_4S)_2$—K—, -$(G_4S)_2$—K—, —K-$(G_4S)_2$—, —R-$(G_4S)_2$—R—, -$(G_4S)_2$—R— and —R-$(G_4S)_2$—.

Suitably the labile peptide linker comprises or more suitably consists of a polypeptide sequence of the format:

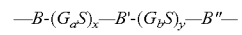

wherein
a is 1 to 10;
b is 1 to 10;
x is 1 to 10;
y is 1 to 10;
B is K or R
B' is K or R and
B" is K or R.

In one embodiment, a is 2 to 5, more suitably a is 4. In one embodiment, b is 2 to 5, more suitably b is 4. In a further embodiment x is 1 to 5. More suitably, x is 2. In a further embodiment y is 1 to 5. More suitably, y is 2. Suitably, B is K. Suitably, B' is K. Suitably, B" is K.

Shielded Labile Sites

Shielding residues in the case of a trypsin or trypsin-like protease labile site may be D or E. Suitably the labile peptide linker comprises one or more shielding residues selected from the list consisting of D or E.

Suitably all K or R residues comprised within the labile peptide linker have at least 1, such as at least 2, such as at least 3, such as at least 4, such as at least 5 shielding residues on their N- and/or C-terminal side, wherein the shielding residues are selected from the list consisting of: D and E. Suitably all K or R residues comprised within the labile peptide linker have 1 to 5, 1 to 4, 1 to 3, 1 to 2, 2 to 5, 2 to 4, 2 to 3, 3 to 5, 3 to 4, 4 to 5 shielding residues on their N- and/or C-terminal side, wherein the shielding residues are selected from the list consisting of: D and E.

Suitably all K and R residues have at least one shielding residue adjacent to them, suitably followed by one or more further contiguous shielding residues. Suitably the shielding residues occur on one or both sides of one or more of the K or R residues.

Suitably the labile peptide linker comprises or more suitably consists of a polypeptide sequence of the format:

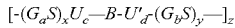
$[-(G_aS)_xU_c-B-U'_d(G_bS)_y-]_z$ wherein
a is 1 to 10;
b is 1 to 10;
U is D or E;
U' is D or E;
c is 0 to 7;
d is 0 to 7;
x is 1 to 10;
y is 1 to 10
z is 1 to 10 and
B is K or R.

Suitably a is 2 to 5, more suitably a is 4. Suitably b is 2 to 5, more suitably b is 4. Suitably x is 1 to 5, more suitably x is 1. Suitably y is 1 to 5, more suitably y is 1. Suitably z is 1 to 3, more suitably z is 1. Suitably, B is K. Suitably, U if present, is D. Suitably, U' if present, is D. In one embodiment c is 1 and d is 1. In another embodiment c is 0 and d is 0. In a further embodiment c is 4 and d is 0. Suitably both U and U' are each individually D and c and d are both 1.

The TNF-alpha binding polypeptide and the IL-6R binding polypeptide, when linked to each other with a protease labile linker, may be deployed in one of the following specific formats:
Anti-TNF-alpha-G$_4$S-K-G$_4$S-anti-IL-6R, anti-IL-6R-G$_4$S-K-G$_4$S-anti-TNF-alpha, anti-TNF-alpha-G$_4$S-KD-G$_4$S-anti-IL-6R anti-IL-6R-G$_4$S-KD-G$_4$S-anti-TNF-alpha, anti-TNF-alpha-G$_4$S-DK-G$_4$S-anti-IL-6R, anti-IL-6R-G$_4$S-DK-G$_4$S-anti-TNF-alpha, anti-TNF-alpha-G$_4$S-DKD-G$_4$S-anti-IL-6R, anti-IL-6R-G$_4$S-DKD-G$_4$S-anti-TNF-alpha, anti-TNF-alpha-G$_4$S-R-G$_4$S-anti-IL-6R, anti-IL-6R-G$_4$S-R-G$_4$S-anti-TNF-alpha, anti-TNF-alpha-G$_4$S-RD-G$_4$S-anti-IL-6R, anti-IL-6R-G$_4$S-RD-G$_4$S-anti-TNF-alpha, anti-TNF-alpha-G$_4$S-DR-G$_4$S-anti-IL-6R, anti-IL-6R-G$_4$S-DR-G$_4$S-anti-TNF-alpha, anti-TNF-alpha-G$_4$S-DRD-G$_4$S-anti-IL-6R or anti-IL-6R-G$_4$S-DRD-G$_4$S-anti-TNF-alpha.

In further embodiments, the TNF-alpha binding polypeptide and the IL-6R binding polypeptide, when linked to each other, may be deployed in one of the above formats except that any one or more (for example, all) of the D residues above are substituted with one or more E residues.

More suitably, the TNF-alpha binding polypeptide and the IL-6R binding polypeptide, when linked to each other with a protease labile linker, may be deployed in either anti-TNF-alpha-G$_4$S-K-G$_4$S-anti-IL-6R format (as exemplified by specific construct ID-9K (residues 87-335 of SEQ ID NO: 19)) or anti-IL-6R-G$_4$S-K-G$_4$S-anti-TNF-alpha format (as exemplified by specific construct ID-10K (residues 87-335 of SEQ ID NO: 20)). Most suitably, they may be deployed in anti-TNF-alpha-G$_4$S-K-G$_4$S-anti-IL-6R format.

In one embodiment, the construct is selected from the list consisting of ID-9K (residues 87-335 of SEQ ID NO: 19) and ID-10K (residues 87-335 of SEQ ID NO: 20). More suitably, the construct is ID-9K.

Chymotrypsin Labile Sites

Alternatively, or in addition to trypsin labile sites, the labile peptide linker of the construct may comprise a cleavage site for chymotrypsin or a chymotrypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 residues selected from the list consisting of W, F, Y, L and M; more suitably W, F and Y. Suitably the labile peptide linker consists of residues selected from the list consisting of S, G, W, F, Y, L and M; such as S, G, W, F and Y.

Suitably the protease-labile linker is of the format $[-(G_aS_b)_x-J_t-(G_cS_d)_y-]_z$ wherein J is W, F, Y, L or M, t is 0 to 5, a is 0 to 10, b is 0 to 5, x is 0 to 10, c is 0 to 10, d is 0 to 5, y is 0 to 10 and z is 1 to 5. More suitably, J is W, F, Y, L or M, t is 0 to 3, a is 0 to 5, b is 0 to 2, x is 0 to 5, c is 0 to 5, d is 0 to 2, y is 0 to 5 and z is 1 to 3.

Suitably the labile peptide linker comprises or more suitably consists of a polypeptide sequence of the format:

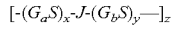
$[-(G_aS)_x-J-(G_bS)_y-]_z$ wherein
a is 1 to 10;
b is 1 to 10;
x is 1 to 10;
y is 1 to 10
z is 1 to 10 and
J is W, F, Y, L or M; such as W, F or Y.

In one embodiment a is 2 to 5, in a further embodiment, b is 2 to 5, in a further embodiment x is 1 to 5, in a further embodiment, y is 1 to 5, in a further embodiment z is 1 to 3. Suitably x is 1, y is 1 and z is 1.

Suitably the labile peptide linker comprises or more suitably consists of a polypeptide sequence of the format:

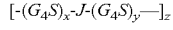
$[-(G_4S)_x-J-(G_4S)_y-]_z$ wherein
x is 1 to 10;
y is 1 to 10
z is 1 to 10 and
J is W, F, Y, L or M; such as W, F or Y.

In one embodiment, x is 1 to 5, in a further embodiment, y is 1 to 5, in a further embodiment z is 1 to 3. Suitably x is 1, y is 1 and z is 1.

Enterokinase Labile Sites

Alternatively, or in addition to trypsin and/or chymotrypsin labile sites, the labile peptide linker of the construct may comprise a cleavage site for an enterokinase. Suitably the labile peptide linker comprises the sequence DDDDK (SEQ ID NO: 31), such as a sequence comprising or consisting of -G$_4$S-DDDDK-G$_4$S—.

MMP Labile Sites

In one embodiment, the labile peptide linker of the construct may comprise a cleavage site for MMP3, MMP10 or MMP12.

Other Labile Sites

In one embodiment, the labile peptide linker of the construct may comprise a cleavage site for other inflammatory or microbial proteases wherein the cleavage site is known.

Stability of Labile Peptide Linkers to Expression Hosts

Various organisms may be used to express recombinant polypeptides. Commonly used expression organisms include yeast, mould and mammalian cells. However, many of these expression organisms also produce proteases, such as trypsin-like proteases, which may cleave the expressed recombinant polypeptide. If the expressed polypeptide incorporates a peptide linker which is labile to one or more proteases present in the intestinal tract, then this peptide linker may undesirably also be labile to proteases produced by the expression organism, thus preventing effective expression of intact polypeptide.

It is advantageous for the labile peptide linker to be substantially non-labile to enzymes produced by the recombinant host used to produce the construct. Suitably the labile peptide linker is substantially resistant to proteases produced by a recombinant host such as bacteria such as *E. coli* or such as a yeast or mould belonging to the genera *Aspergillus, Saccharomyces, Kluyveromyces, Hansenula* or *Pichia*; such as *Saccharomyces cerevisiae* or *Pichia pastoris*.

Suitably the recombinant host is a yeast or a mould. Suitably the yeast belongs to the genera *Saccharomyces, Kluyveromyces, Hansenula, Pichia, Candida* or *Torulopsis*. Suitably the mould belongs to the genus *Aspergillus, Acremonium, Alternaria, Chrysosporium, Cladosporium, Dictyostelium, Fusarium, Mucor, Penicillium, Rhizopus, Stachybotrys, Trichoderma* and *Trichophyton*.

The Gastrointestinal Tract and Digestive Enzymes

The gastrointestinal tract (GIT) is an organ system responsible for consuming and digesting foodstuffs, absorbing nutrients, and expelling waste. In humans and other mammals, the GIT consists of the oesophagus, stomach, small intestine (duodenum, jejunum and ileum) and large intestine (cecum, colon, rectum and anal canal). Various pathogens may colonise and various diseases may manifest in different areas of the GIT. The intestinal tract (as opposed to the gastrointestinal tract) consists of the small and large intestine.

The different parts of the gastrointestinal tract each contain a complex mixture of digestive enzymes. Proteases are involved in digesting polypeptide chains into shorter fragments by splitting the peptide bonds that link amino acid residues (proteolysis). Some detach the terminal amino acids from the protein chain (exopeptidases), others attack internal peptide bonds of a protein (endopeptidases). Proteolysis can be highly promiscuous such that a wide range of protein substrates are hydrolysed. This is the case for proteases which cleave the wide array of ingested polypeptides in the intestinal tract into smaller polypeptide fragments.

Many proteases typically bind to a single amino acid (a labile site) on the substrate and so only have specificity for that residue. The proteases present in the intestinal tract include trypsin, trypsin-like proteases, chymotrypsin, chymotrypsin-like proteases, carboxypeptidase, elastase, aminopeptidase, carboxypeptidase and enteropeptidase. Trypsin-like proteases cleave peptide bonds following lysine or arginine residues. Chymotrypsin-like proteases cleave peptide bonds following hydrophobic residues, such as tyrosine, phenylalanine, tryptophan, leucine and methionine. Particularly tyrosine, phenylalanine and tryptophan.

Particularly in the context of an oral medicament, it may be desirable for the binding polypeptides to be substantially resistant to one or more (such as all) proteases of the intestinal tract, while the labile peptide linker (if used) is labile to one or more (such as all) proteases of the intestinal tract.

Suitably the polypeptides in the construct are substantially resistant to one or more proteases and suitably the labile peptide linker (if present) is labile to one or more proteases, wherein said one or more proteases are present in the small or large intestine, more suitably the jejunum, the ileum and/or the cecum. A substantially resistant polypeptide substantially retains neutralisation ability and/or potency when exposed to one or more proteases.

Such proteases include proteases sourced from gastrointestinal tract commensal microflora or pathogenic bacteria, for example wherein the proteases are cell membrane-attached proteases, secreted proteases and proteases released on cell lysis. Such proteases may also include IBD inflammatory proteases such as MMP3, MMP10 and MMP12. Suitably the one or more proteases are serine proteases. Suitably the one or more proteases are selected from the group consisting of enteropeptidase, trypsin, trypsin-like proteases, chymotrypsin and chymotrypsin-like proteases.

Suitably, the polypeptides substantially retain neutralisation ability and/or potency when delivered orally and after exposure to the intestinal tract (for example, after exposure to proteases of the small and/or large intestine and/or IBD inflammatory proteases). Proteases of, or produced in, the small and/or large intestine include proteases sourced from intestinal commensal microflora and/or pathogenic bacteria, for example wherein the proteases are cell membrane-attached proteases, excreted proteases and proteases released on cell lysis). Most suitably the proteases are trypsin and chymotrypsin.

Suitably the intestinal tract is the intestinal tract of a dog, pig, rat, guinea pig, hamster, rabbit, human, cynomolgus monkey or mouse. The small intestine suitably consists of the duodenum, jejunum and ileum. The large intestine suitably consists of the cecum, colon, rectum and anal canal.

The polypeptides substantially retain neutralisation ability when suitably at least 10%, more suitably 20%, more suitably 30%, more suitably 40%, more suitably 50%, more suitably 60%, more suitably 70%, more suitably 80%, more suitably 90%, more suitably 95%, more suitably 100% of the original neutralisation ability of the polypeptides or construct is retained after exposure to proteases present in the small and/or large intestine and/or IBD inflammatory proteases; after a given time period of exposure at a given temperature. This concept is referred to herein as '% survival'.

Suitably the polypeptide substantially retains neutralisation ability after exposure to proteases present in the small and/or large intestine and/or IBD inflammatory proteases for, for example, up to at least 2, more suitably up to at least 3, more suitably up to at least 4, more suitably up to at least 5, more suitably up to at least 5.5, more suitably up to at least 16, more suitably up to at least 21 or more suitably up to at least 22 hours, at 37 degrees C.

Suitably 10% or more, more suitably 20% or more, more suitably 30% or more, more suitably 40% or more, more suitably 50% or more, more suitably 60% or more, more suitably 70% or more of the neutralisation ability of the polypeptides is retained after 4, 6, 7 or 16 hours of exposure to conditions of the intestinal tract, more suitably the small or large intestine, more suitably human faecal extract.

Suitably 10% or more, more suitably 20% or more, more suitably 30% or more, more suitably 40% or more, more suitably 50% or more, more suitably 60% or more, more suitably 70% or more of the neutralisation ability of the polypeptides is retained after suitably 4, 6, 7 or 16 hours of exposure to mouse small intestinal supernatant.

Autoimmune Diseases and/or Inflammatory Diseases

The compositions and constructs provided by the invention may in particular find utility in the prevention or treatment of autoimmune diseases and/or inflammatory diseases.

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin. An inflammatory disease is a disease characterised by inflammation. Many inflammatory diseases are autoimmune diseases and vice-versa.

Autoimmune Diseases and/or Inflammatory Diseases of the GIT

The chronic inflammatory bowel diseases (IBD) Crohn's disease and ulcerative colitis, which afflict both children and adults, are examples of autoimmune and inflammatory diseases of the GIT (Hendrickson et al 2002, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al 2002, herein incorporated by reference in its entirety).

In these diseases the TNF-alpha is produced in the lamina propria underlying the gastrointestinal epithelium. This epithelium is disrupted in IBD and facilitates transport of the immunoglobulin chain variable domain into the lamina propria—the site of TNF-alpha production and biological action in these diseases. Other diseases of the GIT include for example the inflammatory disease mucositis (suitably drug- and radiation induced-mucositis) where inflammatory lesions are present in the mucosa disrupting the epithelial tight junctions which also allow the compositions of the invention access to the site of TNF-alpha production. In mucositis the lesions can occur anywhere from mouth to anus and for mouth and oesophagus lesions a mouthwash or cream preparation containing the composition may be used. For anal and rectal lesions, suppositories, creams or foams containing the composition would be suitable for topical application. The composition will be cleared from the lamina propria or other inflammatory sites via absorption into the bloodstream at sites of inflammation or via lymphatic clearance and subsequent entry into the bloodstream. The composition will therefore reach the liver via the bloodstream and will be cleared via glomerular filtration in the kidney. There is therefore good rationale that the composition of the invention will function therapeutically in diseases such as autoimmune hepatitis, type II diabetes and glomerular nephritis.

Interleukin-6 is a proinflammatory cytokine that is considered to be involved in the pathogenesis of IBD and IL6-trans-signalling via soluble IL6-R is thought to play a particularly important role in mediating effects of IL-6 associated with the perpetuation of chronic intestinal inflammation (see Mitsuyama et al., 2007). High levels of IL-6 production have been found in cultured CD and UC intestinal mucosal biopsies (Gustot et al., 2005; Kusugami et al., 1995; Reimund et al., 1996; Hosokawa et al., 1999) associated with increased levels of sIL-6R production (Hosokawa, 1999). Levels of IL-6 and sIL-6R production were greater in "involved" vs "non-involved" IBD tissue and were correlated with the severity of clinical disease. Lamina propria cells were found to be major producers of IL-6 (Reinecker et al., 1993; Kusugami et al., 1995; Reimund et al., 1996; Hosokawa et al., 1999) and sIL6Rs (Hosokawa et al., 1999). In cell cultures, IBD mucosal tissue-derived macrophages were the main cell type producing IL-6 (Kusugami et al., 1995) and sIL6R (Hosokawa et al., 1999) on a per cell basis, while T cells, B cells and epithelial cells produced substantially lower amounts. Interestingly, the levels of IL-6 production by IBD tissue and tissue derived cells far exceeded the levels of sIL6R production (see Hosokawa et al., 1999).

In inflamed IBD tissue, the production of IL-6 and shedding of IL-6Rs from activated macrophages results in the formation of soluble IL-6/sIL-6R complexes that can activate trans-signalling in cells that express only the gp130 subunit. This mechanism, which extends IL-6 responsiveness to an increased number of target cells, is considered to play an important role in the orchestration of mucosal inflammatory processes. The mechanism of IL-6 induced intestinal epithelial cell proliferation and regeneration is thought to involve signal transduction mediated via membrane bound IL-6 receptors (cis-signalling) (Rose-John, 2012; Waetzig & Rose-John 2012). The anti-human IL-6R antibody tocilizumab blocks both IL-6R classical signalling and IL-6/sIL-6R mediated trans-signalling and therefore blocks both pro-inflammatory, and potentially protective activities of IL-6. A rationale for the development of selective antagonists of IL-6-trans-signalling has been proposed based on the concept that this might avoid the inhibition of beneficial epithelial regenerative effects of IL-6 (see Rose-John et al, 2012; Waetzig & Rose-John 2012) that are mediated via mIL-6Rs (cis-signalling). An oral pharmaceutical product with this profile could have safety and efficacy advantages over existing IL-6 neutralising antibodies for the treatment of Crohn's disease based on anti-inflammatory and improved mucosal healing properties.

Suitably the composition of the invention is used in the treatment or prevention of an autoimmune and/or inflammatory disease of the GI (gastrointestinal) tract.

Suitably the composition of the invention is for use in the treatment of an autoimmune and/or inflammatory disease of the GI tract selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis (more suitably Crohn's disease or ulcerative colitis, most suitably Crohn's disease).

Oral delivery of the composition will ideally treat inflammatory diseases where TNF-alpha and/or IL-6R (or IL-6) contributes to at least a proportion of the pathology and more suitably wherein the immunoglobulin chain variable domain can access the tissue where the TNF-alpha and/or IL-6R is biologically active.

Autoimmune Diseases and/or Inflammatory Diseases of the Skin

Psoriasis is a debilitating autoimmune, dermatological, disease. Plaque psoriasis, the most common form of the disease, is characterized by red skin covered with silvery scales. Histologically the picture is one of disordered differentiation and hyperproliferation of keratinocytes within the psoriatic plaque with inflammatory cell infiltrates (Ortonne, 1999). The psoriatic skin lesions are inflammatory, red, sharply delimited plaques of various shapes with characteristic silvery lustrous scaling. The term psoriasis includes psoriasis and the symptoms of psoriasis including erythema, skin thickening/elevation and scaling.

Biological agents of use in the treatment of psoriasis include anti-TNF-alpha therapies (such as monoclonal antibodies against TNF, e.g. adalimumab and infliximab, or TNF-alpha receptor fusion proteins such as etanercept), humanised antibodies to CD11a (efalizumab) or agents which bind to CD2 such as alefacept (thereby blocking the CD2 LFA3 interaction). It should be noted that not all of the biological agents listed here have been approved for use in the treatment of psoriasis.

The composition of the invention may be incorporated into a cream/ointment or other topical carrier for administration to inflammatory skin lesions where TNF-alpha and/or IL-6R or IL-6 contributes to the pathology of such lesions.

Suitably the composition of the invention is for use in the treatment of an autoimmune and/or inflammatory disease of the skin selected from the list consisting of pemphigus, psoriasis, eczema and scleroderma.

Therapeutic Use and Delivery

Suitably the composition of the invention is for use as a medicament, suitably administered by oral administration, suitably for use in the treatment or prevention of diseases of the GIT and/or the treatment or prevention of diseases such as autoimmune disease and/or inflammatory disease, such as inflammatory bowel disease. The composition of the invention may also be used in the treatment or prevention of other medical conditions by oral administration such as metabolic disorders, such as obesity. In one embodiment, the composition of the invention is intended to have local effect in the intestinal tract. In one embodiment, the composition of the invention is not for use in the treatment or prevention of diseases by delivery into the circulation in therapeutically effective quantities.

In one aspect of the invention there is provided a method of treating autoimmune disease and/or inflammatory disease comprising administering to a person in need thereof a therapeutically effective amount of the inventive composition.

The anti-TNF-alpha binding polypeptide and the anti-IL-6R binding polypeptide may be co-formulated in a composition of the invention or alternatively may be separately formulated and administered separately, sequentially or simultaneously.

The TNF-alpha binding polypeptide and the IL-6R binding polypeptide may be administered by the same route or by different routes. For example, the TNF-alpha binding polypeptide may be administered orally while the IL-6R binding polypeptide may be administered rectally.

In one aspect of the invention, there is provided a TNF-alpha binding polypeptide for use in the treatment or prevention of an autoimmune disease and/or inflammatory disease, together with an IL-6R binding polypeptide. In a further aspect, there is provided an IL-6R binding polypeptide for use in the treatment or prevention of an autoimmune disease and/or inflammatory disease, together with a TNF-alpha binding polypeptide.

In a further aspect of the invention there is provided a method of treating autoimmune disease and/or inflammatory disease comprising administering to a person in need thereof a TNF-alpha binding polypeptide, together with an IL-6R binding polypeptide. There is also provided a method of treating autoimmune disease and/or inflammatory disease comprising administering to a person in need thereof an IL-6R binding polypeptide, together with a TNF-alpha binding polypeptide.

In a further aspect of the invention there is provided a composition comprising a TNF-alpha binding polypeptide and an IL-6R binding polypeptide for use in the treatment or prevention of inflammatory bowel disease and/or mucositis.

In a further aspect of the invention there is provided a composition comprising a TNF-alpha binding polypeptide and an IL-6R binding polypeptide for use in the treatment or prevention of inflammatory bowel disease and/or mucositis, wherein the composition is orally administered.

In a further aspect of the invention there is provided the use of a composition comprising a TNF-alpha binding polypeptide and an IL-6R binding polypeptide in the manufacture of a medicament for the treatment or prevention of inflammatory bowel disease and/or mucositis.

In a further aspect of the invention there is provided the use of a composition comprising a TNF-alpha binding polypeptide and an IL-6R binding polypeptide in the manufacture of a medicament for the treatment or prevention of inflammatory bowel disease and/or mucositis by oral administration.

In a further aspect of the invention there is provided a method of treating or preventing inflammatory bowel disease and/or mucositis comprising administering to a person in need thereof a composition comprising a TNF-alpha binding polypeptide and an IL-6R binding polypeptide.

In a further aspect of the invention there is provided a method of treating or preventing inflammatory bowel disease and/or mucositis comprising orally administering to a person in need thereof a composition comprising a TNF-alpha binding polypeptide and an IL-6R binding polypeptide.

In the embodiments above, the inflammatory bowel disease is suitably Crohn's disease or ulcerative colitis, most suitably Crohn's disease. Furthermore, in the embodiments above, the TNF-alpha binding polypeptide is suitably a polypeptide comprising an antibody fragment and/or the IL-6R binding polypeptide is suitably a polypeptide comprising an antibody fragment. Most suitably, the TNF-alpha binding polypeptide and the IL-6R binding polypeptide are both polypeptides comprising an antibody fragment.

Administration of one binding polypeptide 'together' with another binding polypeptide means that the therapeutic windows of each binding polypeptide overlap with each other. This means that, for example, a therapeutically effective amount of each binding polypeptide is present in the body of the subject at the same time. In a particular embodiment, a therapeutically effective amount of each binding polypeptide is present at the site of therapeutic need at the same time.

A therapeutically effective amount of a composition of the invention is an amount which is effective, upon single or multiple dose administration to a subject, in neutralising the biological effects of a chosen target to a significant extent in a subject. A therapeutically effective amount may vary according to factors such as the disease state, age, sex, and weight of the individual, and the ability of the construct to elicit a desired response in the individual. A therapeutically effective amount is also one in which any toxic or detrimental effects of the construct are outweighed by the therapeutically beneficial effects. The composition of the invention can be incorporated into pharmaceutical compositions suitable for oral administration to a subject.

A composition of the invention may be formulated for oral delivery. The compositions of the invention may be in a variety of forms. These include, for example, liquid, semi-solid and solid dosage forms, such as liquid solutions, dispersions or suspensions, tablets, pills and powders. Solid dosage forms are preferred. The composition may comprise a pharmaceutically acceptable excipient, and suitably may be used in the form of ingestible tablets, buccal tablets, troches, capsules, elixirs, suspensions, syrups, wafers, and the like.

Typically, the composition comprises a pharmaceutically acceptable excipient such as a carrier, forming a pharmaceutical composition. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids. Suitably, the polypeptides in the composition of the invention are lyophilised before being incorporated into a pharmaceutical composition.

A composition of the invention may also be provided with an enteric coating. An enteric coating is a polymer barrier applied on oral medication which protects the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH ~3), but will do so in the higher pH environment present in the small intestine (pH above 6) or in the colon (pH above 7.0). The pH-dependent release polymer is selected such that the composition of the invention will be released at about the time that the dosage reaches the target region of the intestinal tract.

The pharmaceutical composition of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary concentrations of polypeptide in a pharmaceutical composition may range from about 1 mg/mL to about 200 mg/ml or from about 50 mg/mL to about 200 mg/mL, or from about 150 mg/mL to about 200 mg/mL.

An aqueous formulation of the pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated construct and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptides against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the pharmaceutical composition of the invention are those to produce the desired therapeutic effect. The dosage range required depends on the precise nature of the pharmaceutical composition or construct, the target region of the intestinal tract, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages of pharmaceutical composition of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week.

The TNF-alpha binding polypeptide and the IL-6R binding polypeptide, when present in the inventive composition and when not linked to each other, may be present in a TNF-alpha binding polypeptide to IL-6R binding polypeptide molar ratio of 20:1 to 1:20, such as 15:1 to 1:15, more suitably 10:1 to 1:10, more suitably 5:1 to 1:5, more suitably 3:1 to 1:3, more suitably 2:1 to 1:2, more suitably 1.5:1 to 1:1.5, most suitably about 1:1.

Treatment of diseases also embraces treatment of exacerbations thereof, amelioration of symptoms thereof and also embraces treatment of patients in remission from disease symptoms to prevent relapse of disease symptoms.

Combination Therapy

A pharmaceutical composition of the invention may also comprise one or more active agents (e.g. active agents suitable for treating diseases such as those mentioned herein). It is within the scope of the invention to use the pharmaceutical composition of the invention in therapeutic methods for the treatment of autoimmune and/or inflammatory diseases as an adjunct to, or in conjunction with, other established therapies normally used in the treatment of bacterial, autoimmune and/or inflammatory diseases.

For the treatment of irritable bowel disease (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/IL23 antibodies (e.g., ustekinumab); anti-IL6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are infliximab, adalimumab, certolizumab pegol or golimumab.

Hence another aspect of the invention provides a pharmaceutical composition of the invention in combination with one or more further active agents, for example one or more active agents described above. In a further aspect of the invention, the pharmaceutical composition or construct is administered sequentially, simultaneously or separately with at least one active agent selected from the list above.

Similarly, another aspect of the invention provides a combination product comprising:

(A) a pharmaceutical composition of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a pharmaceutical composition or construct of the present invention and another therapeutic agent, in admixture with a pharmaceutically acceptable adjuvant, diluent or carrier.

The invention also encompasses a kit of parts comprising components:

(i) a pharmaceutical composition of the present invention in admixture with a pharmaceutically acceptable adjuvant, diluent or carrier; and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of bacterial infection such as *Clostridium difficile* infection, autoimmune and/or inflammatory diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Vectors and Hosts

The term "vector", as used herein, is intended to refer to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode the polypeptides in the composition of the invention. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a vector comprising the polynucleotide encoding a construct of the invention or cDNA comprising said polynucleotide. In a further aspect of the invention there is provided a host cell transformed with said vector, which is capable of expressing the construct of the invention. Suitably the host cell is a yeast such as a yeast belonging to the genera *Aspergillus, Saccharomyces, Kluyveromyces, Hansenula* or *Pichia*, such as *Saccharomyces cerevisiae, Escherchia coli* or *Pichia pastoris*.

The specific constructs ID-9K to ID-14K disclosed herein as SEQ ID NO: 19 to SEQ ID NO: 24 each comprise an export signal sequence which is the yeast mating factor alpha secretion sequence (MFal). Other suitable export signal sequences include the yeast invertase (SUC2) signal, the acid phosphatase (PHOS) signal sequence (Romanos et al 1992) and the BGL2 gene signal sequence (Achstetter et al 1992). These and other export signal sequences can equally be used in combination with unlinked anti-TNF-alpha binding polypeptides and anti-IL-6R binding polypeptides such as ID-38F and ID-142V disclosed herein.

Preparative Methods

Polypeptides and constructs comprising polypeptides can be obtained and manipulated using the techniques disclosed for example in Green and Sambrook 2012.

Monoclonal antibodies can be produced using hybridoma technology, by fusing a specific antibody-producing B cell with a myeloma (B cell cancer) cell that is selected for its ability to grow in tissue culture and for an absence of antibody chain synthesis (Köhler et al., 1975 and Nelson et al., 2000, herein incorporated by reference in their entirety).

A monoclonal antibody directed against a determined antigen can, for example, be obtained by:
a) immortalizing lymphocytes obtained from the peripheral blood of an animal previously immunized with a determined antigen, with an immortal cell and preferably with myeloma cells, in order to form a hybridoma,
b) culturing the immortalized cells (hybridoma) formed and recovering the cells producing the antibodies having the desired specificity.

Alternatively, the use of a hybridoma cell is not required. Accordingly, monoclonal antibodies can be obtained by a process comprising the steps of:
a) cloning into vectors, especially into phages and more particularly filamentous bacteriophages, DNA or cDNA sequences obtained from lymphocytes especially peripheral blood lymphocytes of an animal (suitably previously immunized with determined antigens),
b) transforming prokaryotic cells with the above vectors in conditions allowing the production of the antibodies,
c) selecting the antibodies by subjecting them to antigen-affinity selection,
d) recovering the antibodies having the desired specificity.

Methods for immunizing camelids, cloning the VHH repertoire of B cells circulating in blood (Chomezynnski et al., 1987), and isolation of antigen-specific VHHs from immune (Arbabi-Ghahroudi et al., 1997) and nonimmune (Tanha et al 2002) libraries using phage, yeast, or ribosome display are known (WO92/01047, Nguyen et al., 2001 and Harmsen et al., 2007. These references are herein incorporated by reference in their entirety.

Antibody fragments such as the scFv and Fv fragments can be isolated and expressed in *E. coli* (Miethe et al., 2013, Skerra et al., 1988 and Ward et al., 1989, herein incorporated by reference in their entirety).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997, herein incorporated by reference in its entirety), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used (Nambiar et al 1984, Sakamar et al., 1988, Wells et al., 1985 and Grundstrom et al., 1985, herein incorporated by reference in their entirety). A gene encoding a polypeptide can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma et al., 1998)

Expression of immunoglobulin chain variable domains such as VHs and VHHs can be achieved using a suitable expression vector such as a prokaryotic cell such as bacteria, for example *E. coli* (for example according to the protocols disclosed in WO94/04678, which is incorporated herein by reference and detailed further below). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference and detailed further below).

Specifically, VHHs can be prepared according to the methods disclosed in WO94/04678 using *E. coli* cells by a process comprising the steps of:
a) cloning in a Bluescript vector (Agilent Technologies) a DNA or cDNA sequence coding for the VHH (for example obtained from lymphocytes of camelids or produced synthetically) optionally including a His-tag,
b) recovering the cloned fragment after amplification using a 5' primer specific for the VHH containing an XhoI site and a 3' primer containing the SpeI site having the sequence TC TTA ACT AGT GAG GAG ACG GTG ACC TG (SEQ ID NO: 13),
c) cloning the recovered fragment in phase in the Immuno PBS vector (Huse et al., 1989, herein incorporated by reference in its entirety) after digestion of the vector with XhoI and SpeI restriction enzymes,
d) transforming host cells, especially *E. coli* by transfection with the recombinant Immuno PBS vector of step c,
e) recovering the expression product of the VHH coding sequence, for instance by affinity purification such as by chromatography on a column using Protein A, cation exchange, or a nickel-affinity resin if the VHH includes a His-tag.

Alternatively, immunoglobulin chain variable domains such as VHs and VHHs are obtainable by a process comprising the steps of:
a) obtaining a DNA or cDNA sequence coding for a VHH, having a determined specific antigen binding site,
b) amplifying the obtained DNA or cDNA, using a 5' primer containing an initiation codon and a HindIII site, and a 3' primer containing a termination codon having a XhoI site,
c) recombining the amplified DNA or cDNA into the HindIII (position 2650) and XhoI (position 4067) sites of a plasmid pMM984 (Merchlinsky et al., 1983, herein incorporated by reference in its entirety),
d) transfecting permissive cells especially NB-E cells (Faisst et al., 1995, herein incorporated by reference in its entirety) with the recombinant plasmid,
e) recovering the obtained products.

Further, immunoglobulin chain variable domains such as VHHs or VHs can be produced using *E. coli* or *S. cerevisiae* according to the methods disclosed in Frenken et al., 2000 and WO99/23221 (herein incorporated by reference in their entirety) as follows:

After taking a blood sample from an immunised llama and enriching the lymphocyte population via Ficoll (a neutral, highly branched, high-mass, hydrophilic polysaccharide which dissolves readily in aqueous solutions—Pharmacia) discontinuous gradient centrifugation, isolating total RNA by acid guanidium thiocyanate extraction (Chomezynnski et al., 1987), and first strand cDNA synthesis (e.g. using a cDNA kit such as RPN 1266 (Amersham)), DNA fragments encoding VHH and VH fragments and part of the short or long hinge region are amplified by PCR using the specific primers detailed on pages 22 and 23 of WO99/23221. Upon digestion of the PCR fragments with PstI and HindIII or BstEII, the DNA fragments with a length between about 300 and 450 bp are purified via agarose gel electrophoresis and ligated in the *E. coli* phagemid vector pUR4536 or the episomal *S. cerevisiae* expression vector pUR4548, respectively. pUR4536 is derived from pHEN (Hoogenboom et al., 1991, herein incorporated by reference in its entirety) and contains the lacI$^q$ gene and unique restriction sites to allow the cloning of the llama VHH and VH genes. pUR4548 is derived from pSY1 (Harmsen et al., 1993, herein incorporated by reference in its entirety). From this plasmid, the BstEII site in the leu2 gene is removed via PCR and the cloning sites between the SUC2 signal sequence and the terminator are replaced in order to facilitate the cloning of the VH/VHH gene fragments. The VH/VHHs have the c-myc tag at the C-terminus for detection. Individual *E. coli* JM109 colonies are transferred to 96 well microtiter plates containing 150 ml 2TY medium supplemented with 1% glucose and 100 mg L$^{-1}$ ampicillin. After overnight growth (37 degrees C.), the plates are duplicated in 2TY medium containing 100 mg L$^{-1}$ ampicillin and 0.1 mM IPTG. After another overnight incubation and optionally freezing and thawing, cells are centrifuged and pelleted and the supernatant can be used in an ELISA. Individual *S. cerevisiae* colonies are transferred to test tubes containing selective minimal medium (comprising 0.7% yeast nitrogen base, 2% glucose, supplemented with the essential amino acids and bases) and are grown for 48 h at 30 degrees C. Subsequently, the cultures are diluted ten times in YPGal medium (comprising 1% yeast extract, 2% bacto peptone and 5% galactose). After 24 and 48 h of growth, the cells are pelleted and the culture supernatant can be analysed in an ELISA. Absorbance at 600 nm (OD600) is optionally measured.

Further, immunoglobulin chain variable domains such as VH/VHHs can be produced using *S. cerevisiae* using the procedure as follows:

Isolate a naturally-occurring DNA sequence encoding the VH/VHH or obtain a synthetically produced DNA sequence encoding the VH/VHH, including a 5'-UTR, signal sequence, stop codons and flanked with Sac and HindIII sites (such a synthetic sequence can be produced as outlined above or for example may be ordered from a commercial supplier such as Geneart (Life Technologies)).

Use the restriction sites for transfer of the VH/VHH gene to the multi-copy integration (MCI) vector pUR8569 or pUR8542, as follows. Cut the DNA sequence encoding the VHH optionally contained within a shuttle vector, cassette or other synthetic gene construct and the MCI vector with SacI and HindIII using: 25 ul VHH DNA (Geneart plasmid or MCI vector), 1 ul SacI, 1 ul HindIII, 3 ul of a suitable buffer for double digestion such as NEB buffer 1 (New England Biolabs) overnight at 37 degrees C. Run 25 ul of digested DNA encoding the VHH and 25 ul of digested MCI vector on a 1.5% agarose gel with 1×TAE buffer and then perform gel extraction for example using QIAquick Gel Extraction Kit (Qiagen)). Set-up a ligation of digested MCI vector and digested DNA encoding the VH/VHH as follows: 100 ng vector, 30 ng VHH gene, 1.5 ul 10× ligase buffer, 1 ul T4 DNA ligase, and ddH$_2$O. Then perform ligation overnight at 16 degrees C.

Next transform the *E. coli* cells. For chemical competent XL-1 blue cells, thaw 200 ul heat competent XL-1 blue cells and add 5 ul ligation mix on ice for about 30 minutes followed by heat shock for 90 seconds at 42 degrees C. Then add 800 ul Luria-Bertani low salt medium supplemented with 2% glucose and recover cells for 2 hours at 37 degrees C. Plate cells on Luria-Bertani agar and ampicillin (100 ug/ml) plates and keep overnight at 37 degrees C. For electro competent TG1 *E. coli* cells, use an electroporation cuvette. In the electroporation cuvette: thaw 50 ul electro competent TG1 cells and 1 ul ligation mix on ice for about 15 minutes. Place the cuvette in the holder and pulse. Add 500 ul of 2TY medium and recover cells for 30 minutes at 37 degrees C. Plate 100 ul of cells on Luria-Bertani, agar, containing ampicillin (100 ug/ml) and 2% glucose plates. Keep plates at 37 degrees C. overnight.

After cloning of the VH/VHH gene into *E. coli* as detailed above, *S. cerevisiae* can be transformed with the linearized MCI vector. Before transformation is carried out, some steps are performed: (i) the DNA should be changed from circular to linear by digestion or else the DNA cannot be integrated into the yeast genome and (ii) the digested DNA should be cleaned of impurities by ethanol precipitation. Also, during the transformation process, the yeast cells are made semi-permeable so the DNA can pass the membrane.

Preparation for yeast transformation: perform a HpaI digestion of the midi-prep prepared from the selected E. coli colony expressing the VHVHH gene as follows. Prepare a 100 ul solution containing 20 ng of midi-prep, 5 ul HpaI, 10 ul of appropriate buffer such as NEB4 buffer (BioLabs), and ddH$_2$O.

Cut the DNA with the HpaI at room temperature overnight. Next perform an ethanol precipitation (and put to one side a 5 ul sample from HpaI digestion). Add 300 ul ethanol 100% to 95 ul HpaI digested midiprep, vortex, and spin at full speed for 5 minutes. Carefully decant when a pellet is present, add 100 ul of ethanol 70%, then spin again for 5 minutes at full speed. Decant the sample again, and keep at 50-60 degrees C. until the pellet is dry. Re-suspend the pellet in 50 ul ddH$_2$O. Run 5 ul on a gel beside the 5 ul HpaI digested sample.

Yeast transformation: prepare YNBglu plates. Use 10 g agar+425 ml water (sterilised), 25 ml filtered 20×YNB (3.35 g YNB (yeast nitrogen base) in 25 ml sterilized H$_2$O) and 50 ml sterile 20% glucose and pour into petri dishes. Pick one yeast colony from the masterplate and grow in 3 ml YPD (Yeast Extract Peptone Dextrose) overnight at 30 degrees C. Next day prepare about 600 ml YPD and use to fill 3 flasks with 275 ml, 225 ml and 100 ml YPD. Add 27.5 ul yeast YPD culture to the first flask and mix gently. Take 75 ml from the first flask and put this in the second flask, mix gently. Take 100 ml from the second flask and put in the third one, mix gently. Grow until reaching an OD660 of between 1 and 2. Divide the flask reaching this OD over 4 Falcon tubes, ±45 ml in each. Spin for 2 minutes at 4200 rpm. Discard the supernatant. Dissolve the pellets in two Falcon tubes with 45 ml H$_2$O (reducing the number of tubes from 4 to 2). Spin for 2 minutes at 4200 rpm. Dissolve the pellets in 45 ml H$_2$O (from 2 tubes to 1). Spin for 2 minutes at 4200 rpm. Gently dissolve the pellets in 5 ml lithium acetate (LiAc) (100 mM), and spin for a few seconds. Carefully discard some LiAc, but retain over half of the LiAc in the tube. Vortex the cells, boil carrier DNA for 5 minutes and quickly chill in ice-water. Add to a 15 ml tube containing: 240 ul PEG, 50 ul cells, 36uLiAc (1M), 25 ul carrier DNA, 45 ul ethanol precipitated VH/VHH. Mix gently after each step (treat the blank sample the same, only without ethanol precipitated VH/VHH). Incubate for 30 minutes at 30 degrees C., gently invert the tube 3-4 times, then heat shock for 20-25 minutes at 42 degrees C. Spin up to 6000 rpm for a brief time. Gently remove the supernatant and add 250 ul ddH$_2$O and mix. Streak all of it on an YNBglu plate until plates are dry and grow for 4-5 days at 30 degrees C. Finally, prepare YNBglu plates by dividing plates in 6 equal parts, number the parts 1 to 6, inoculate the biggest colony and streak out number 1. Repeat for other colonies from big to small from 1 to 6. Grow at 30 degrees C. for 3-4 days large until colonies are produced. The VH/VHH clones are grown using glucose as a carbon source, and induction of VH/VHH expression is done by turning on the Galactose-7-promoter by adding 0.5% galactose. Perform a 3 mL small scale culture to test the colonies and choose which one shows the best expression of the VH or VHH. This colony is then used in purification.

Purification: the VH/VHH is purified by cation exchange chromatography with a strong anion resin (such as Capto S).

On day 1, inoculate the selected yeast colony expressing the VH/VHH in 5 ml YPD medium (YP medium+2% glucose) and grow the cells in 25 mL sealed sterile tubes at 30 degrees C. overnight (shaking at 180 rpm). On day 2, dilute the 5 ml overnight culture in 50 mL freshly prepared YP medium+2% glucose+0.5% galactose, grow the cells in 250 ml aerated baffled flasks at 30 degrees C. for two nights (shaking at 180 rpm). On day 4, spin the cells down in a centrifuge at 4200 rpm for 20 min. Cation exchange purification step using a strong anion resin: adjust the pH of the supernatant containing the ligand to 3.5. Wash 0.75 ml resin (+/−0.5 mL slurry) per of 50 mL supernatant with 50 mL of ddH$_2$O followed by three washes with binding buffer. Add the washed resin to the supernatant and incubate the suspension at 4 degrees C. on a shaker for 1.5 hours. Pellet the resin-bound VH/VHH by centrifugation at 500 g for 2 minutes and wash it with wash buffer. Decant supernatant and re-suspend the resin with 10 mL of binding buffer. Put a filter in a PD-10 column, pour the resin in the column and let the resin settle for a while, then add a filter above the resin. Wait until all binding buffer has run through. Elute the VH/VHH with 6×0.5 ml elution buffer. Collect the elution fractions in eppendorf tubes. Measure the protein concentration of the 6 eluted fractions with a Nanodrop. Pool the fractions that contain the VHH and transfer the solution into a 3,500 Da cutoff dialysis membrane. Dialyze the purified protein solution against 3 L of PBS overnight at 4 degrees C. On day 5, dialyze the purified protein solution against 2 L of fresh PBS for an additional 2 hours at 4 degrees C. Finally, calculate the final concentration by BCA.

Although discussed in the context of the VH/VHH, the techniques described above could also be used for scFv, Fab, Fv and other antibody fragments if required.

Multiple antigen-binding fragments (suitably VH/VHHs) can be fused by chemical cross-linking by reacting amino acid residues with an organic derivatising agent such as described by Blattler et al., 1985 (herein incorporated by reference in its entirety). Alternatively, the antigen-binding fragments may be fused genetically at the DNA level i.e. a polynucleotide construct formed which encodes the complete polypeptide construct comprising one or more antigen-binding fragments. One way of joining multiple antigen-binding fragments via the genetic route is by linking the antigen-binding fragment coding sequences either directly or via a peptide linker. For example, the carboxy-terminal end of the first antigen-binding fragment may be linked to the amino-terminal end of the next antigen-binding fragment. This linking mode can be extended in order to link antigen-binding fragments for the construction of tri-, tetra-, etc. functional constructs. A method for producing multivalent (such as bivalent) VHH polypeptide constructs is disclosed in WO 96/34103 (herein incorporated by reference in its entirety).

Suitably, the polypeptide can be produced in a fungus such as a yeast (for example, S. cerevisiae) comprising growth of the fungus on a medium comprising a carbon source wherein 50-100 wt % of said carbon source is ethanol, according to the methods disclosed in WO02/48382. Large scale production of VHH fragments in S. cerevisiae is described in Thomassen et al., 2002 (herein incorporated by reference in its entirety).

In one aspect of the invention there is provided a method of making a composition of the invention comprising the step of expressing a polynucleotide encoding a TNF-alpha binding polypeptide using a suitable host and expressing a polynucleotide encoding an IL-6R binding polypeptide in a suitable host and adding both polypeptides to a composition.

In a further aspect of the invention there is provided a method of making a construct of the invention comprising the step of expressing a polynucleotide encoding a construct of the invention using a suitable host.

The present invention will now be further described by means of the following non-limiting examples.

EXAMPLES

Example 1: Potency of a TNF-Alpha Binding Polypeptide, ID-38F, Compared to TNF-Alpha Binding Polypeptides of the Prior Art (L929 Assay)

The neutralising potency of ID-38F (SEQ ID NO: 8), an immunoglobulin chain variable domain which binds to TNF-alpha, was compared in one and the same L929 assay (for further details, see above under 'TNF-alpha binding polypeptides') to that of the following anti-TNF-alpha polypeptides of the prior art:
TNF1 (a VHH disclosed in WO2006122786, therein SEQ ID NO: 52)
TNF3 (a VHH disclosed in WO2006122786, therein SEQ ID NO: 60)
TNF30 (a VHH disclosed in WO2006122786, therein SEQ ID NO: 96)
VHH #3E (a VHH disclosed in WO2004041862, therein SEQ ID NO: 4)
Adalimumab (commercially available human monoclonal antibody, trade name HUMIRA®)
Materials
L929 cells ($10^4$ cells/well)
96-well plates (Costar)
DMEM (Invitrogen) supplemented with Pen/Strep+2 mM L-glutamine
Human TNF-alpha (Invitrogen) concentration: 500 pg/ml
Actinomycin D concentration (Sigma): 0.75 ug/mL
ID-38F purified from *S. cerevisiae*
ID-38F Flag-His tagged purified from *E. coli*
Adalimumab
TNF1, TNF3, TNF30, VHH #4E purified from *E. coli* with Flag-His tags
Range of dilutions: 5 pM-30 nM (1:3 dilutions)
Incubation times: 23 h
Alamar Blue cell viability reagent (Invitrogen, DAL1100): 10 uL/well
3% SDS
Microplate reader (Fluostar Optima) (OD590 nm)
Method
$10^4$ L929 cells/well in 100 ul were plated on day 0 in 96 well micro-plates (Costar) in DMEM complete medium and stored over night at 37° C. and 5% $CO_2$. On day 1 serial dilutions 1:3 (in DMEM+Act. D) for each purified VHH/Ab were set up at double the assay concentrations (with volumes sufficient for triplicates) starting from a top concentration of 60 nM. 165 uL of each dilution were then diluted 1:1 with 165 uL of hTNF-alpha 2× (1 ng/mL) prepared in DMEM+Act.D. 0.9 mL of TNF 2× were diluted with 0.9 mL of cell medium+Act. D to have the TNF only control in the assay. The medium was removed from each well of the assay microplates and the cells were incubated with 100 uL of each TNF+VHH dilution, CM+act. D or TNF only control. After 23 h of incubation at 37° C. and 5% $CO_2$, 10 ul of Alamar Blue were added to each well, the cells were incubated for 2 h at 37° C. and 5% $CO_2$, and 50 ul of 3% SDS were subsequently added to each well. The plates were then read at 590 nm.

Results

The resultant neutralisation curves (produced with GraphPad Prism, using 4 parameter non-linear regression curve) are shown in FIG. 1. EC50 values are shown in Table 1.

TABLE 1

| Anti-TNF-alpha polypeptide | EC50 (nM) |
|---|---|
| TNF1 | 0.751 |
| TNF3 | 0.631 |
| TNF30 | 0.420 |
| VHH#3E | 1.110 |
| ID38F-Flag-His (*E. coli*-produced) | 0.102 |
| ID38F (*S. cerevisiae*-produced) | 0.127 |
| Adalimumab | 0.091 |

It can be seen from FIG. 1 and Table 1 that VHH #3E was the least potent anti-TNF-alpha polypeptide in neutralising human soluble TNF-alpha-induced cytotoxicity in L929 cells. ID-38F (both *E. coli*- and *S. cerevisiae*-produced) had an approximately 4 fold—1 log lower EC50 than that of the prior art anti-TNF-alpha VHHs.

Example 2: Potency of a TNF-Alpha Binding Polypeptide, ID-38F (ELISA Assay)

The neutralising activities of adalimumab and ID-38F in a TNFR-2—TNF-alpha ELISA were compared.

An ELISA plate was coated overnight with 1.5 μg/ml TNFR-2 (Enbrel) in PBS overnight at 4° C. The plate was then washed and blocked in 1% BSA for >1 h at RT before being used. Adalimumab and ID-38F were made up in 1% BSA and 0.5% human AB serum in PBS at 9.258 nM and 20 nM respectively. From these solutions a further 10 dilutions were made for each antibody using a 1:1.6875 dilution factor and 1% BSA, 0.5% human AB serum in PBS as a diluent. All the antibody dilutions were mixed 1:1 with 5 ng/ml TNF-alpha and incubated for 1 h before adding to the ELISA plate and incubate at RT for 2 h. The plate was washed and incubated with 0.4 μg/ml biotinylated anti TNFα (P31A) for 2 h before an incubation with Extravidin-HRP (1/2000). Finally, the plate was washed again and 100 μl/well of TMB were added. Colour development was stopped by adding 50 μl/well of 0.5M $H_2SO_4$ and OD450 nm measurements were taken using a BMG Labtek Fluostar Omega plate reader.

TNFR-2—TNFα binding inhibition curves for adalimumab and ID-38F were generated from the data using a robust fit of a 4 parameter, non-linear curve fit in GraphPad Prism (not shown). These analyses also generated the EC50 data for both antibodies (see Table 2 below).

TABLE 2

| | Adalimumab, pM | ID-38F, pM |
|---|---|---|
| EC50 | 213.5 | 382.8 |

Example 3: Intestinal Protease Resistance of a TNF-Alpha Binding Polypeptide, ID-38F Experiments were performed to investigate the stability of ID-38F when exposed to enzymes of the GIT (present in mouse small intestinal supernatant and human faecal supernatant).

The contents of the small intestines from seven C57BL/6 male mice were removed with 0.9% saline, combined, homogenised and centrifuged. The resulting supernatant was removed, aliquoted and frozen.

Human faecal samples were turned into slurries with addition of 1×PBS. The slurries were then pooled, centrifuged and the supernatants removed, aliquoted and stored at −80 degrees C. This process removes the faecal matrix, including any cellular material.

Digests

ID-38F stock solution at 250 ug/mL was prepared in 0.34% (3400 ug/mL) BSA. To 55.2 uL of faecal or small intestinal supernatant on ice, 4.8 ul of ID-38F was added and mixed by vortexing. 25 uL was immediately removed and mixed with 25 uL of ice-cold protease stop solution (undigested control), and frozen at −80 degrees C. Aliquots of 25 ul were placed in wells of a polycarbonate thin-walled PCR plate and incubated for 17 h or 7 h respectively at 37 degrees C. After incubation, the digested ID-38F samples were placed on ice and 25 uL of ice-cold protease stop solution was added to each tube. The samples were frozen at −80 degrees C. before assay.

ELISA

ID-38F was diluted in 1% BSA+1× protease inhibition solution, mixed 1:1 with 5 ng/mL h-TNF-alpha, and incubated at RT for 1 h. The ID-38F and TNF-alpha mixture was then loaded onto blocked ELISA plates coated with 1 ug/mL etanercept and incubated for 2 hours with shaking at RT. The plates were washed 4× with PBST, dried by tapping and incubated with the biotinylated rabbit anti human-TNF-alpha polyclonal antibody (50 uL/well, 0.3 ug/mL) for 1 hour with shaking at RT. After 1 h, the plates were washed and incubated with mAvidin-HRP (50 uL/well, 1/1000 dilution) with shaking at RT for 30 min. The plates were then washed and dried as before and developed using 100 uL TMB. Standard curves (in PBS) were run alongside the non-digested samples. The top concentration of ID-38F used in the standard curve was 100 ng/mL.

Data Analyses

After digestion, the ID-38F concentration was measured using a TNFR2-interference ELISA. In this assay, ID-38F is mixed with TNF-alpha. The remaining level of TNF-alpha is then measured. The concentration of ID-38F is inferred from the amount of TNF-alpha inhibited from binding the TNFR2 receptor that is bound to the ELISA plate. Raw OD450 values were adjusted with blank readings taken from wells containing 1% BSA only. Standard curves were plotted using Graphpad Prism using non-linear regression to fit four-parameter curves. ID-38F concentration in the test samples were calculated in Graphpad Prism using the standard curve. The % survival was calculated by dividing the average ID-38F concentration in the 0-time point wells by the average ID-38F concentration for a single time point. The standard error of the ratio of two means was calculated.

Results

ID-38F achieved approximately 20% survival after 16 hours incubation in mouse small intestinal supernatant and approximately 45% survival after 16 hours incubation in human faecal supernatant. ID-38F is therefore remarkably stable to intestinal proteases.

Example 4: Binding Affinity for TNF-Alpha of a TNF-Alpha Binding Polypeptide, ID-38F TNF-alpha was coupled to a switchSENSE® chip via covalently linked DNA to perform molecular biophysical analysis. Humira Fab or ID-38F were then flowed over the chip. Under these conditions, the $K_{on}$ values were virtually identical (ID-38F appears to have slightly higher affinity than Humira Fab). Using this format (TNF-alpha bound to the chip), an off rate was obtained for the Humira Fab. However, due to its small size, reliable data could not be obtained for ID-38F in this orientation. Instead, ID-38F was coupled to the chip and TNF-alpha was flowed over the chip. When the off-rate data for Humira Fab (with TNF on the chip) and TNF-alpha (with ID-38F on the chip) were compared, the off rates were again very similar. It was confirmed that TNF-alpha was trimeric at the point of measurement (i.e. when being bound by Humira Fab or ID-38F). The affinity measurements are provided below in Table 3. The Kd of ID-38F was ascertained to be 16.8 pM.

TABLE 3

| | $k_{on}(10^6 \, M^{-1}s^{-1})$ | $k_{off}(10^{-5}s^{-1})$ | Kd(pM) | Assay orientation | Detection signal |
|---|---|---|---|---|---|
| Humira | 32 ± 1 (n = 3) | 3.7 ± 0.9 (n = 3) | 1.2 ± 0.4 | TNFa immob. | Dynamic Response |
| Humira Fab | 10 ± 1 (n = 5) | 5.1 ± 0.3 (n = 3) | 5.1 ± 0.7 | TNFa immob. | Dynamic Response |
| ID-38F | 2.5 ± 0.1 (n = 5) | 4.2 ± 2.0 (n = 3) | 16.8 ± 8.6 | ID-38F immob. | Fluorescence |
| ID-38F | 8.1 ± 0.2 (n = 3) | not measurable | No data | TNFa immob. | Fluorescence |

Example 5: Administration of ID-38F to Humans—Polypeptide Concentration at the Ileal-Caecal Junction and in Faeces Polypeptide Concentration at the Ileal-Caecal Junction The aim of this study was to demonstrate that ID-38F (a TNF-alpha binding ICVD), incorporated into an enterically-coated pharmaceutical composition, is delivered at high concentrations to the ileal-caecal junction in man, a major site for Crohn's disease and the proximal site of Crohn's disease lesions in the intestine of many patients.

Four human volunteers, fitted with terminal ileostomy bags each received a single oral dose of 1665 mg ICVD, formulated into mini-tabs inside size 00 capsules (9 capsules in total). In these otherwise healthy individuals, the entire contents of the terminal ileum drains into the detachable external bag. At each hourly time point post-dosing, the fitted bag containing the total ileal effluent was removed, frozen and a new bag was fitted. Ileostomy samples were collected in this manner every hour for a period of 12 hours post dosing. Following this time, ileostomy samples were collected every four hours up to 24 hours post dosing. A pre-dosing sample (day −1) was also taken as a control. Any partially dissolved mini-tablets observed in the bags were removed prior to analysis such that only fully soluble ICVD was analysed. The ICVD was extracted from the ileal fluid and concentrations of active ICVD were determined by functional ELISA, assuming that 1 g ileal fluid is equivalent to 1 mL liquid volume.

The data revealed high concentrations of active ICVD present in the ileostomy bags, in the range 200 nM up to 1 mM. In addition, high concentrations were observed over several hours of bag changes for each subject (see Table 4).

TABLE 4

| Subject | Hour post dose | ICVD concentration in ileal fluid (nM) |
| --- | --- | --- |
| 31001 | 2 | 406350 |
| 31001 | 3 | 305560 |
| 31001 | 4 | 791 |
| 31002 | 2 | 32780 |
| 31002 | 3 | 1130000 |
| 31002 | 4 | 792060 |
| 31002 | 5 | 81750 |
| 31002 | 6 | 12780 |
| 31002 | 7 | 1300 |
| 31002 | 8 | 422 |
| 31002 | 9 | 1410 |
| 31002 | 10 | 7520 |
| 31002 | 11 | 10080 |
| 31002 | 12 | 9210 |
| 31002 | 16 | 6980 |
| 31003 | 3 | 1060000 |
| 31003 | 4 | 496030 |
| 31003 | 5 | 7080 |
| 31003 | 8 | 46110 |
| 31003 | 9 | 75480 |
| 31003 | 10 | 16030 |
| 31003 | 11 | 72940 |
| 31003 | 12 | 15870 |
| 31003 | 16 | 881 |
| 31004 | 2 | 126190 |
| 31004 | 3 | 235 |
| 31004 | 4 | 11110 |
| 31004 | 5 | 3770 |
| 31004 | 6 | 6730 |

ICVD was not detected in any of the predose (Day −1) samples from any subject.

In summary, a sustained and high concentration of ID-38F was achieved at the ileal-caecal junction in these human volunteers.

Polypeptide Concentration in Faeces

Healthy male subjects aged 18-45 were dosed orally with a single dose of either 62, 555, 1665 or 4995 mg of ID-38F ICVD, delivered in the enterically-coated pharmaceutical composition described above. Each single dose per subject was administered between 8:30 to 12:00 on day 1. Faecal samples were collected pre dose (either on day −1, or prior to dosing on day 1) and at all available times post dosing up to the morning of day 4 (the end of the study). ICVD was extracted from the faeces and concentrations of active ICVD were determined by functional ELISA, assuming that 1 g faeces is equivalent to 1 mL liquid volume and that the polypeptide is uniformly distributed in the faeces.

High concentrations in the range 180 nM to 724 pM were obtained in the faeces of subjects (see Table 5).

TABLE 5

| Subject ID | mg dose ICVD | Faecal sample collection day | Pre or post dose | [ICVD] in faeces (nM) |
| --- | --- | --- | --- | --- |
| 11001 | 62 | −1 | PRE DOSE | 0 |
| 11001 |  | 1 | POST DOSE | 1013 |
| 13001 | 555 | −1 | PRE DOSE | 0 |
| 13001 |  | 2 | POST DOSE | 1052 |

TABLE 5-continued

| Subject ID | mg dose ICVD | Faecal sample collection day | Pre or post dose | [ICVD] in faeces (nM) |
| --- | --- | --- | --- | --- |
| 13003 | 555 | −1 | PRE DOSE | 0 |
| 13003 |  | 1 | POST DOSE | 1938 |
| 13003 |  | 2 | POST DOSE | 1511 |
| 14002 | 1665 | −1 | PRE DOSE | 0 |
| 14002 |  | 1 | POST DOSE | 5491 |
| 14002 |  | 2 | POST DOSE | 558 |
| 14004 | 1665 | −1 | PRE DOSE | 0 |
| 14004 |  | 2 | POST DOSE | 27532 |
| 14006 | 1665 | −1 | PRE DOSE | 0 |
| 14006 |  | 2 | POST DOSE | 62579 |
| 15001 | 4995 | −1 | PREDOSE | 0 |
| 15001 |  | 1 | POST DOSE | 10047 |
| 15001 |  | 2 | POST DOSE | 135285 |
| 15001 |  | 3 | POST DOSE | 330 |
| 15004 | 4995 | −1 | PREDOSE | 0 |
| 15004 |  | 3 | POST DOSE | 273 |
| 15005 | 4995 | 1 | PRE DOSE | 0 |
| 15005 |  | 1 | POST DOSE | 724684 |
| 15005 |  | 2 | POST DOSE | 258703 |
| 15005 |  | 3 | POST DOSE | 3536 |
| 15006 | 4995 | −1 | PRE DOSE | 0 |
| 15006 |  | 1 | POST DOSE | 57120 |
| 15006 |  | 2 | POST DOSE | 358 |
| 15006 |  | 2 | POST DOSE | 186 |

Anti-TNF agents that are used clinically to treat Crohn's disease, such as adalimumab (Humira) and infliximab (Remicade), are administered either by intravenous infusion or subcutaneous injection. Ungar et al. (2016) state that trough serum levels of 56-83 nM (8-12 μg/mL) for adalimumab and 42-70 nM (6-10 μg/mL) for infliximab are required to achieve mucosal healing in 80%-90% of patients with IBD, and that this could be considered as a "therapeutic window".

Concentrations of anti-TNF-alpha ICVD delivered to the ileal-caecal junction and recovered in the faeces of human volunteers during the clinical work in this section were significantly higher than these levels and are thus predicted to be efficacious as a treatment for Crohn's disease. This assumes that gut luminal concentrations of anti-TNF-alpha ICVD are comparable to serum concentrations of marketed anti-TNF agents with respect to access/penetration to the gut mucosa and sub-mucosa. However, it has been demonstrated in further experimental work (not shown) that this anti-TNF-alpha ICVD, dosed orally in DSS colitis mice, is able to penetrate to the lamina propria where it is resident for several hours, despite a lack of target (TNF) engagement in mice.

These results demonstrate successful oral delivery of therapeutic levels of ICVD from the ileal-caecal junction to the anus.

Example 6: Potency of an IL-6R Binding Polypeptide, ID-123V (a Variant of ID-142V), Compared to an IL-6R Binding Polypeptide of the Prior Art, 20A11

The inhibitory potency and efficacy (maximal inhibition) of *E.coli*-produced ID-123V (an ICVD which binds to IL-6R, SEQ ID NO: 34) and tocilizumab (a commercially available anti-IL-6R antibody with the trade name ACTEMRA®) were confirmed in vitro in the gp130 ELISA, TF-1 cell and M1 cell functional assays measuring responses mediated via human IL-6R. The potency of ID-123V and tocilizumab in these assays is shown in Tables 6.1 to 6.3. The assays use the standard protocols provided above. The gp130 assay uses a final assay concentration of 10 ng/mL IL-6R and 50 ng/mL IL-6.

TABLE 6.1 gp130 ELISA assay

| Construct | gp130 ELISA EC50 nM |
|---|---|
| ID-123V | 0.498 |
| Tocilizumab | 1.831 |
| 20A11 | 0.220 |

TABLE 6.2

TF-1 cell assay

| Construct | TF-1 cell assay EC50 nM (5 ng/ml IL-6) |
|---|---|
| ID-123V | 4.50 |
| Tocilizumab | 1.12 |
| 20A11 | 0.56 |

TABLE 6.3

M1 cell assay

| Construct | M1 cellular assay EC50 nM |
|---|---|
| ID-123V | 4.20 |
| Tocilizumab | 5.36 |

In summary, it can be seen that ID-123V has high potency in the various assays performed.

Example 7: Binding Affinity and Specificity for Human IL-6R of an IL-6R Binding Polypeptide, ID-123V The binding kinetics of ID-123V were compared against tocilizumab in a Biacore study. The ICVD was fixed to the Biacore sensor plate and soluble human IL-6R was flowed over the plate to detect binding. Tocilizumab and ID-123V had similar Kds of 0.39 and 1.1 nM, respectively. The results indicate that ID-123V binds strongly to IL-6R.

Example 8: Potency of an IL-6R Binding Polypeptide, ID-142V

The potencies of ID-142V (SEQ ID NO: 16), ID-123V (SEQ ID NO: 34) and tocilizumab were assessed in the M1 cell assay (the M1 cell assay is dependent on IL-6 trans signalling).

It can be seen that the ICVD ID-123V detailed in the examples above is equivalent to ID-142V except for ID-123V being produced in *E. coli* and therefore lacking the E1 D mutation.

Rapidly growing M1 cells were suspended in RPMI+3% FCS medium at 106 cells/ml. Fifty microliters of cell suspension were added to wells on the assay plates. ID-123V was produced in *E. coli* and contained a C-terminal Flag, His tag, whilst ID-142V contained no tag and was produced in yeast. As a result, the N-terminus for the yeast produced ID-142V was Asp (D), whilst the N-terminus of ID-123V was Glu (E). For each antibody a range of concentrations were prepared from 600 nM solutions using a 1:2.667 dilution factor, using RPMI+3% FCS as a diluent. All antibody dilutions were mixed with 120 ng/ml IL-6 and 600 ng/ml IL-6 (both in RPMI+3% FCS) in a 1:1:1 ratio, then 50 µl of each mixture were added to the assay plates (1:1), giving a final IL-6 and IL-6R concentration of 100 ng/ml and 20 ng/ml IL-6 and IL-6R respectively. Plates were incubated for 5 days, then viable cell mass was measured by incubating with 10 µl/well Alamar blue for 5 h and measuring 620 nm emission fluorescence.

Data for % inhibition of the IL-6+IL-6R response are shown in Table 7 below. In summary, tocilizumab potency was similar to ID-142V.

TABLE 7

| Binding polypeptide | EC50, nM |
|---|---|
| ID-123V | 2.31 |
| ID-142V | 4.05 |
| Tocilizumab | 4.16 |

Example 9: Intestinal Protease Resistance of IL-6R Binding Polypeptides ID-123V and ID-142V, Compared to an IL-6R Binding Polypeptide of the Prior Art Experiments were performed to investigate the stability of ID-123V, ID-142V and an IL-6R binding polypeptide of the prior art (20A11) when exposed to enzymes of the GIT (present in mouse small intestinal supernatant and human faecal supernatant).

Assessment in Mouse Small Intestinal Supernatant and Human Faecal Extract Assays ID-123V, ID-142V and 20A11 were tested for survival in mouse small intestinal supernatant and human faecal extract assays. Survival was measured by a gp130 plate ELISA.

A mouse small intestinal supernatant assay was performed with 7 hours' digestion and a human faecal extract assay was performed with 16 hours' digestion. % survival was established for the ICVDs as follows in Table 8.

TABLE 8

| ICVD | Mouse small intestinal supernatant 7 h % survival | Human faecal extract 16 h % survival |
|---|---|---|
| ID-123V | 85 | 95 |
| ID-142V | 47 | 92 |
| 20A11 | 0 | 0 |

It can be seen that ID-123V and ID-142V are highly protease resistant ICVDs, while 20A11 is highly unstable in protease matrices.

Resistance to Gastrointestinal Matrix Metalloproteases

Levels of activated matrix metalloproteases (MMPs) are increased in the inflamed mucosa of patients with intestinal bowel disease. These MMPs are able to digest native human IgG and therapeutic agents that contain a human IgG scaffold (Biancheri et al, 2015). In the case of the anti-TNF-alpha therapy etanercept, this digestion causes a significant reduction in TNF-alpha neutralising potency. To confirm that ID-123V is resistant to MMPs, ID-123V was incubated for 18 hours in the presence of activated recombinant human MMP3 and MMP12.

Following incubation, ID-123V was fully potent at neutralising IL-6R, as measured using an IL-6-sIL-6R-gp130 functional ELISA. However, after the same incubation time, MMP3 and MMP12 digested full-length etanercept and tocilizumab (anti-IL-6R) to smaller fragments, as measured by Western blotting.

Mouse Digestive Transit and Survival

Results of the in vitro studies described above showed that ID-123V was highly resistant to inactivation by proteases present in a supernatant extract prepared from mouse small intestinal contents. A subsequent study was performed to investigate the stability of ID-123V during passage through the gastrointestinal system of the mouse. ID-123V was formulated with a further, unrelated ICVD in a milk and bicarbonate mixture to protect against denaturation at low pH and digestion by pepsin in the stomach. Following administration of the ICVDs to mice by oral gavage, concentrations of the ICVDs in stomach, small intestine, caecum and colon were determined at 3 hours post-dosing. In addition, the ICVD concentration in faecal pellets collected at hourly intervals was measured.

Four mice were tested. The transit and excretion of the ICVDs in faeces varied between the mice tested. In three of the mice, ID-123V was detected in faeces between 2 and 4 hours after dosing, suggesting that ID-123V can survive transit through the mouse GI tract.

Examining the concentrations of ID-123V in each compartment at 3 hours post-dose revealed ID-123V in the stomach and small intestine. It is expected therefore that ID-123V will have good stability in the human intestinal tract.

Example 10: Investigation of the Inhibitory Effects of a TNF-Alpha Binding Polypeptide and an IL-6R Binding Polypeptide, Administered Separately and in Combination, on the Phosphorylation of Signalling Proteins in Ex Vivo Cultured IBD Tissue The TNF-alpha binding polypeptide used in the experiments detailed below is the ICVD ID-38F (SEQ ID NO: 8). The IL-6R binding polypeptide used in the experiments detailed below is the ICVD ID-142V (SEQ ID NO: 16).

Infliximab is effective for the treatment of IBD. Infliximab is thought to act primarily by neutralising the biological activity of TNF leading to inhibition of the downstream pro-inflammatory effects of the cytokine. Activation of the many different cell types present in diseased tissue by TNF and secondary inflammatory mediators involves multiple receptor signalling pathways resulting in the phosphorylation of receptors, protein kinases and transcription factors. Experiments have shown that (i) patterns of protein phosphorylation are altered in IBD vs normal intestinal tissue and that (ii) patterns of phosphorylation are sensitive to inhibitors of specific pro-inflammatory mechanisms.

The effects of a TNF-alpha binding polypeptide and an IL-6R binding polypeptide (the ICVDs ID-38F and ID-142V, respectively), delivered both individually and in combination, on the phosphorylation of signalling proteins in intestinal mucosal tissue from IBD patients was investigated as detailed below.

IBD Tissue

Endoscopic colonic mucosal biopsies were obtained from patients with active Inflammatory Bowel Disease (IBD). Patient characteristics are listed in Table 9.

TABLE 9

Details of IBD Patients, Disease Presentation and Medication

| Patient # | Presentation/Biopsy | Medication | Sex; birth year |
|---|---|---|---|
| CD2241 | /colon | Azathioprine | M; 1976 |
| CD2244 | /colon | Azathioprine, Budesonide | M; 1982 |
| CD2250 | /colon | No meds; (on Humira 1 year ago) | M; 1992 |
| CD2256 | /terminal ileum | No meds | M; 1985 |
| UC2245 | mild pancolitis | Mesalazine oral and topical | M; 1955 |
| UC2249 | mayo 1-2 colitis left-sided | No meds | F; 1985 |

Organ Culture

Mucosal biopsies taken from active IBD cases (CD & UC) with inflamed mucosa were cultured (one biopsy per well) in 24-well plates (VWR International, Lutterworth, UK) in 300 µl serum-free HL-1 medium (Cambrex BioScience, Wokingham, UK) supplemented with glutamine, 100 µg/ml penicillin, 100 µg/ml streptomycin, 50 ug/mL gentamicin and cultured at 37° C., 5% $CO_2$. Biopsies were cultured for 24 h with the addition of the following antibodies; ID-38F or ID-142V each at a final concentration of 250 nM, ID-38F plus ID-142V each at a concentration of 250 nM and ID-2A (irrelevant control ICVD) 500 nM. Details of the antibodies are summarised in Table 10. Supernatants and tissue samples collected at the end of the experiment were snap-frozen and stored at −70° C.

TABLE 10

Details of Antibodies and Treatment Groups

| Well | Time | Antibody | Activity | Assay |
|---|---|---|---|---|
| 1 | 24 h | ID-2A | Unrelated ICVD | Negative Control |
| 2 | 24 h | ID-38F | Anti-TNF ICVD | Mono-specific |
| 3 | 24 h | ID-142V | Anti-IL-6R ICVD | Mono-specific |
| 4 | 24 h | ID-38F + ID-142V | Anti-TNF + Anti-IL-6R ICVDs | Combined Specificity |

Signalling Arrays and Data Analysis

For the analysis of phospho-protein content the IBD tissue samples were thawed, lysed in RIPA buffer (Sigma-Aldrich, St. Louis, Mo.) supplemented with phosphatase inhibitor cocktail 2 (Sigma-Aldrich) and protease inhibitor cocktail (Sigma-Aldrich), both at 1%. Protein concentrations of the lysates were determined by the Bio-Rad protein assay (Bio-Rad Laboratories, Hemel Hempstead, UK) and samples diluted to 1.0 mg/ml in Array Diluent Buffer.

Figure 2:
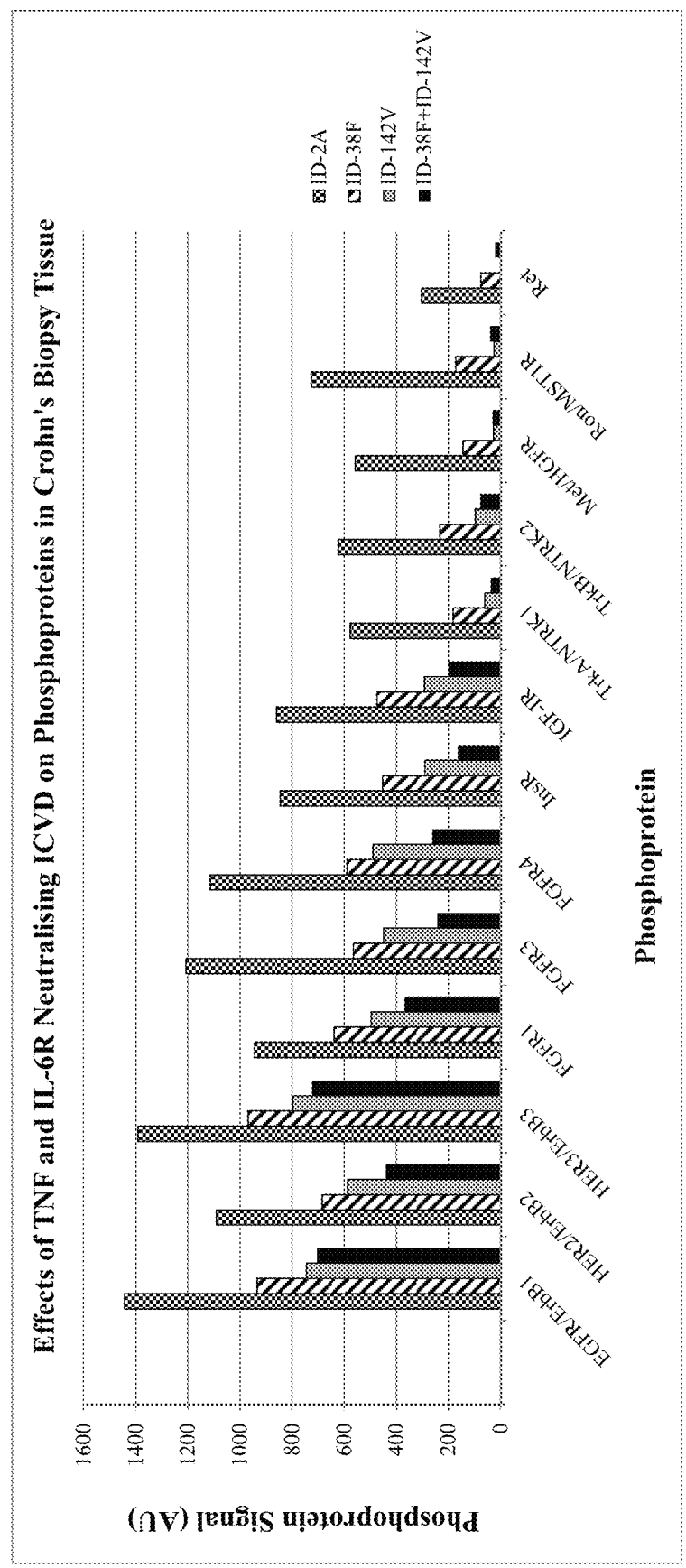
FIG. 2—Effects of TNF-alpha and IL-6R neutralising ICVDs, alone and in combination, on phosphoproteins in Crohn's biopsy tissue (phosphoprotein signal)
Figure 2:
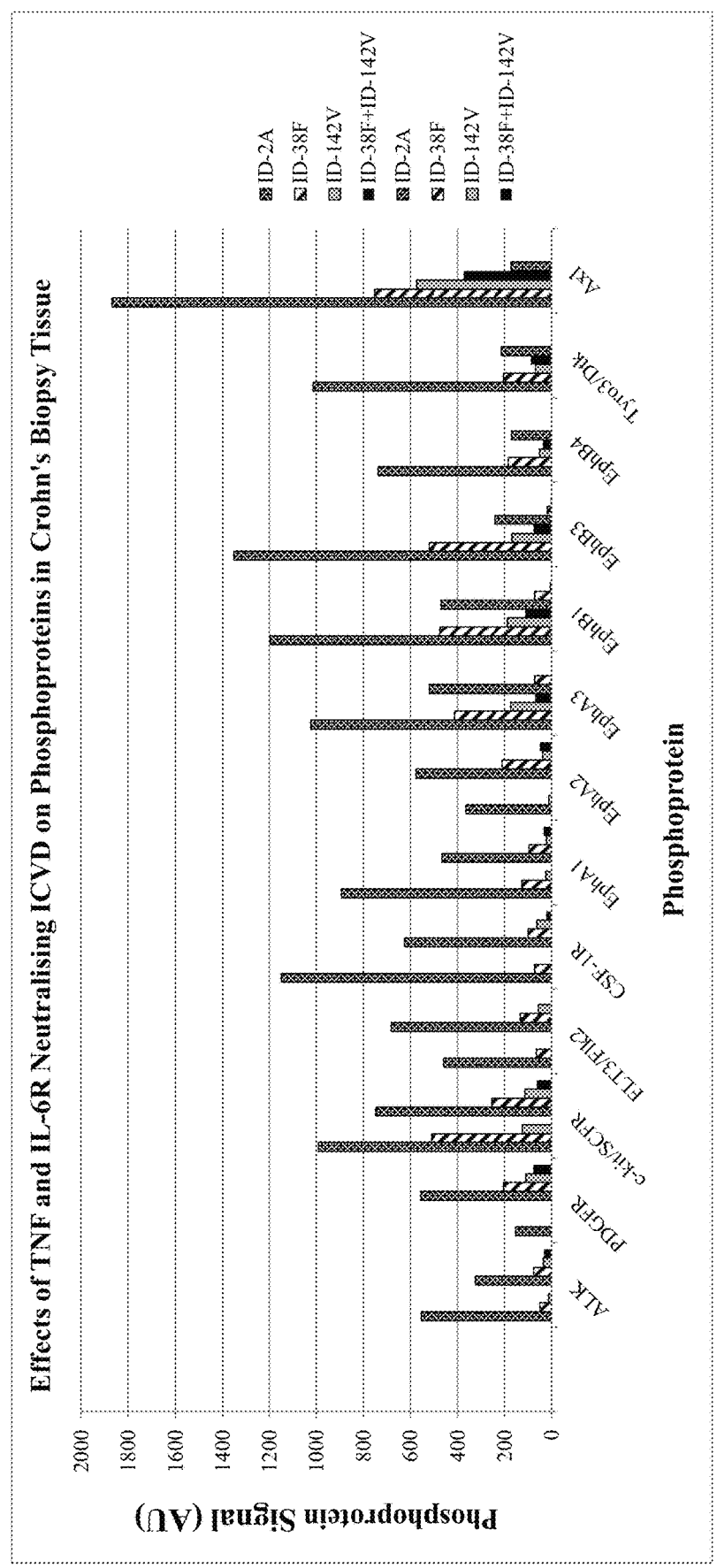

1. The phosphorylation status of receptor tyrosine kinases and signalling molecules was determined by using PathScan RTK signalling arrays (Cell Signalling Technology, Danvers, Mass.). The array kit allows for the simultaneous detection of 28 receptor tyrosine kinases and 11 important signalling nodes, when phosphorylated at tyrosine or other residues.
2. A total of 150 ug of protein from each biopsy tissue lysate was probed onto each array. For each CD and UC patient, the lysates prepared from the set of antibody-treated biopsies (ID-2A, ID-38F, ID-142V and ID-38F+ID-142V) were analysed on the same slide.
3. The chemiluminescent signals of all arrays were detected on X-ray films, and the pixel intensities were measured using ImageJ software.
4. For each antibody treatment, the phosphoprotein signals obtained from each of the four different patient biopsies (n=4 CD lysates) were used to calculate mean+/−SD pixel intensity values that are shown in FIG. 2 (shown in 'AU'—arbitrary units). FIG. 2 is split over three sections, with different phosphoproteins displayed in each section.

Figure 3:
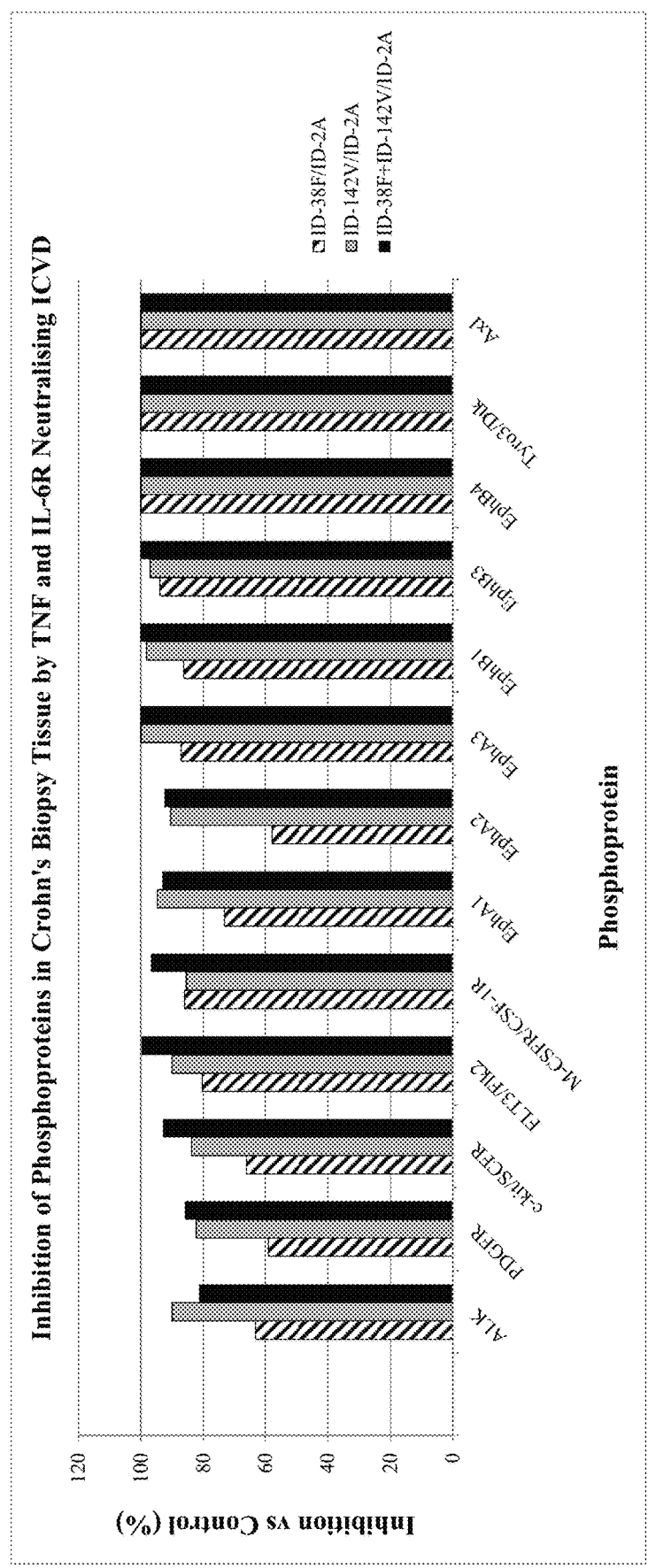
FIG. 3—Inhibition of phosphoproteins in Crohn's biopsy tissue by TNF-alpha and IL-6R neutralising ICVDs, alone and in combination (inhibition vs control (%))
Figure 3:
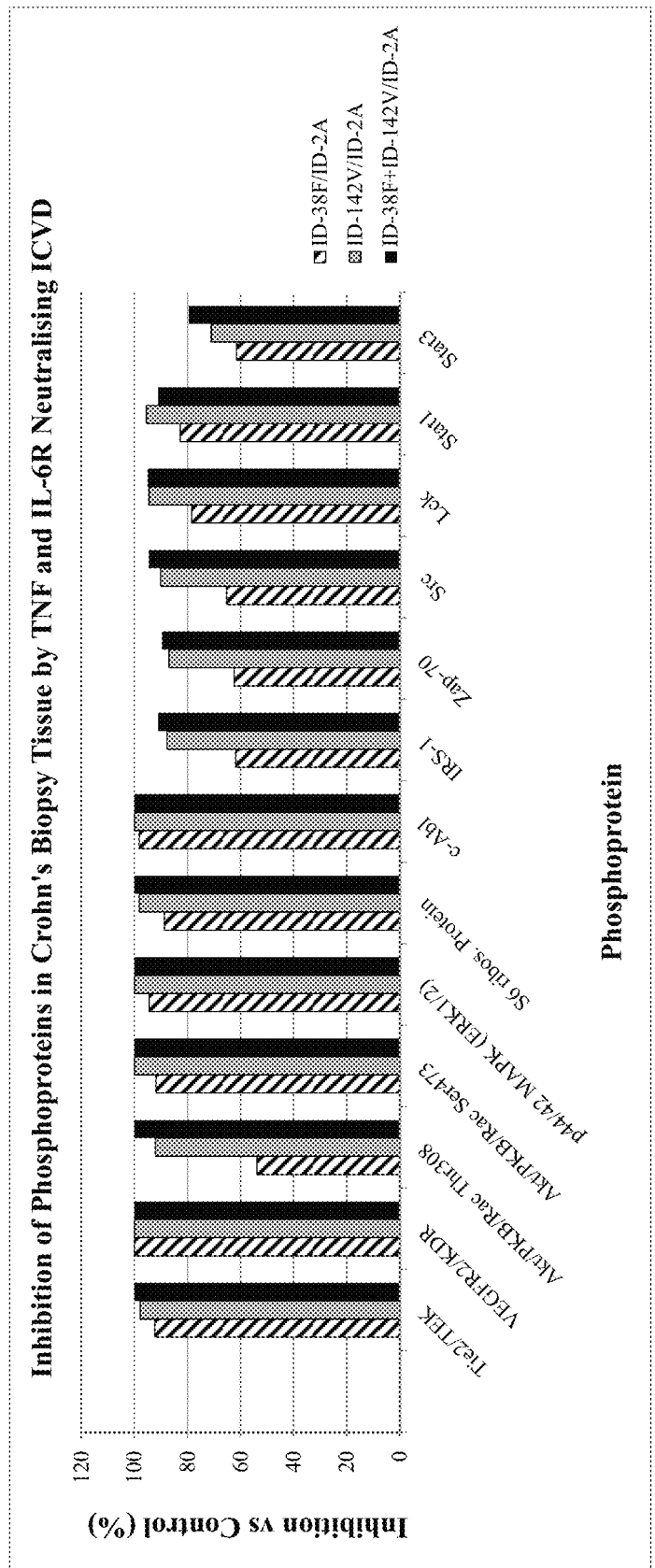

5. To account for differences between patients the pixel array data obtained for each of the experimental treatments were normalised against the pixel values obtained for the corresponding patient and ID-2A treatment control. Percentage inhibition of control values were calculated and presented in FIG. 3. Values for each treatment (ID-38F, ID-142V and ID-38F+ID-142V) were derived from the analysis of lysates from four different CD patients.

Figure 4:
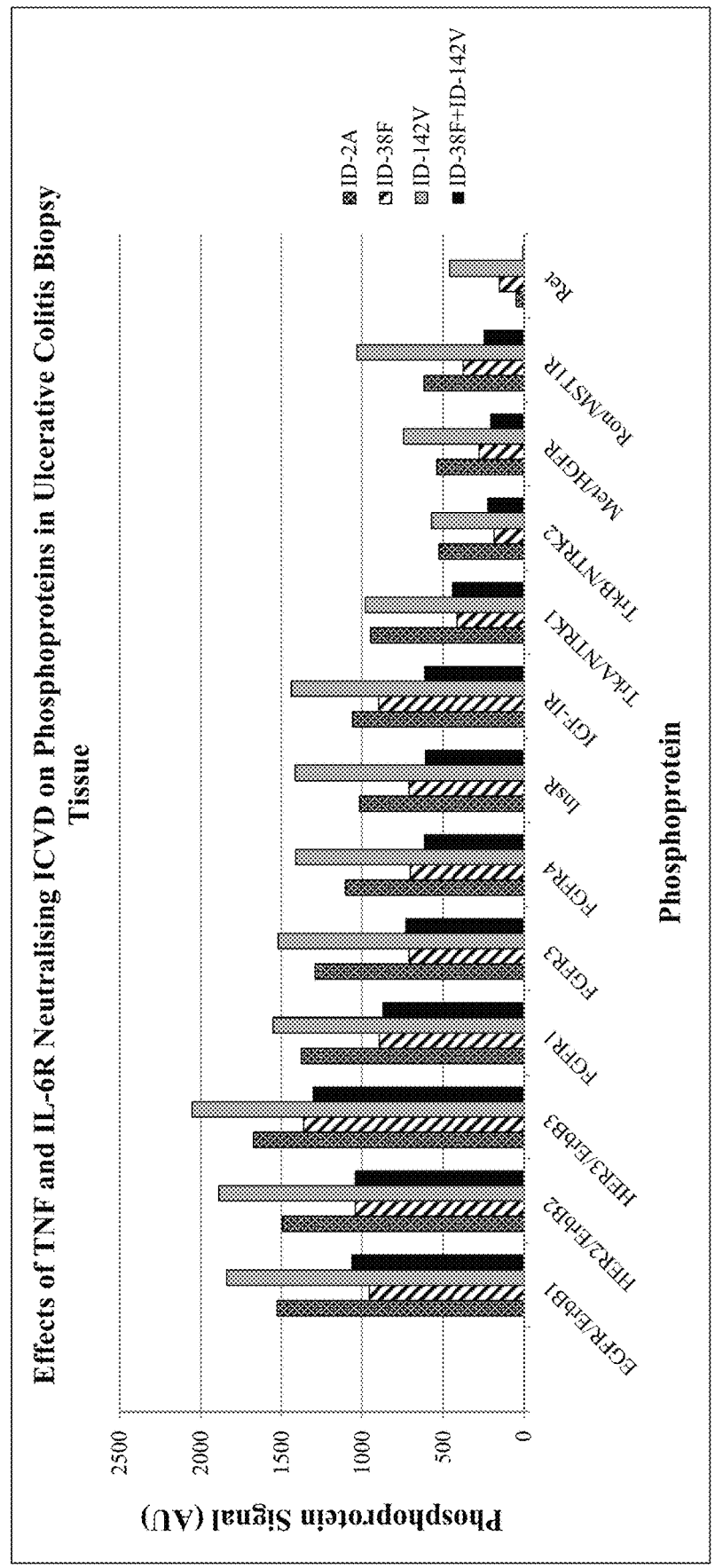
FIG. 4—Effects of TNF-alpha and IL-6R neutralising ICVDs, alone and in combination, on phosphoproteins in ulcerative colitis biopsy tissue (phosphoprotein signal)
Figure 4:
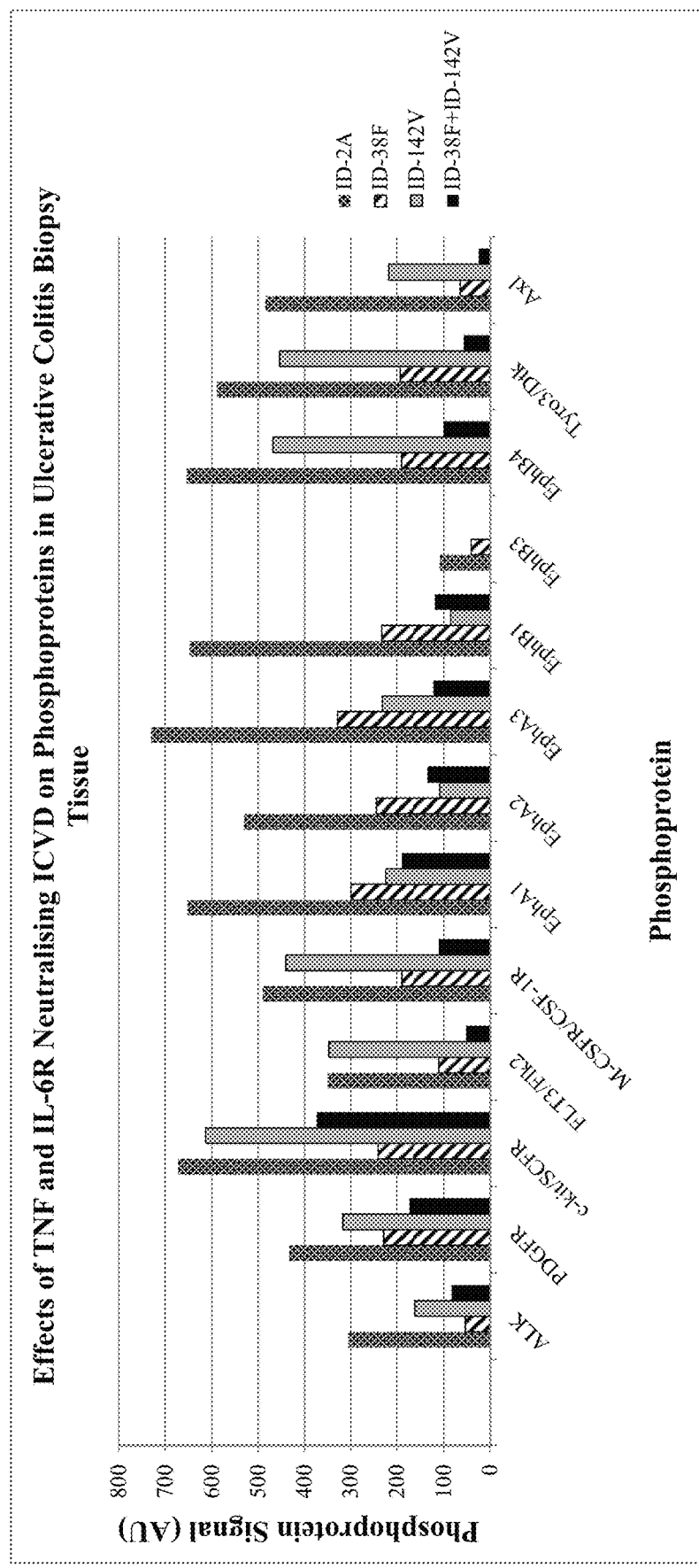
Figure 4:
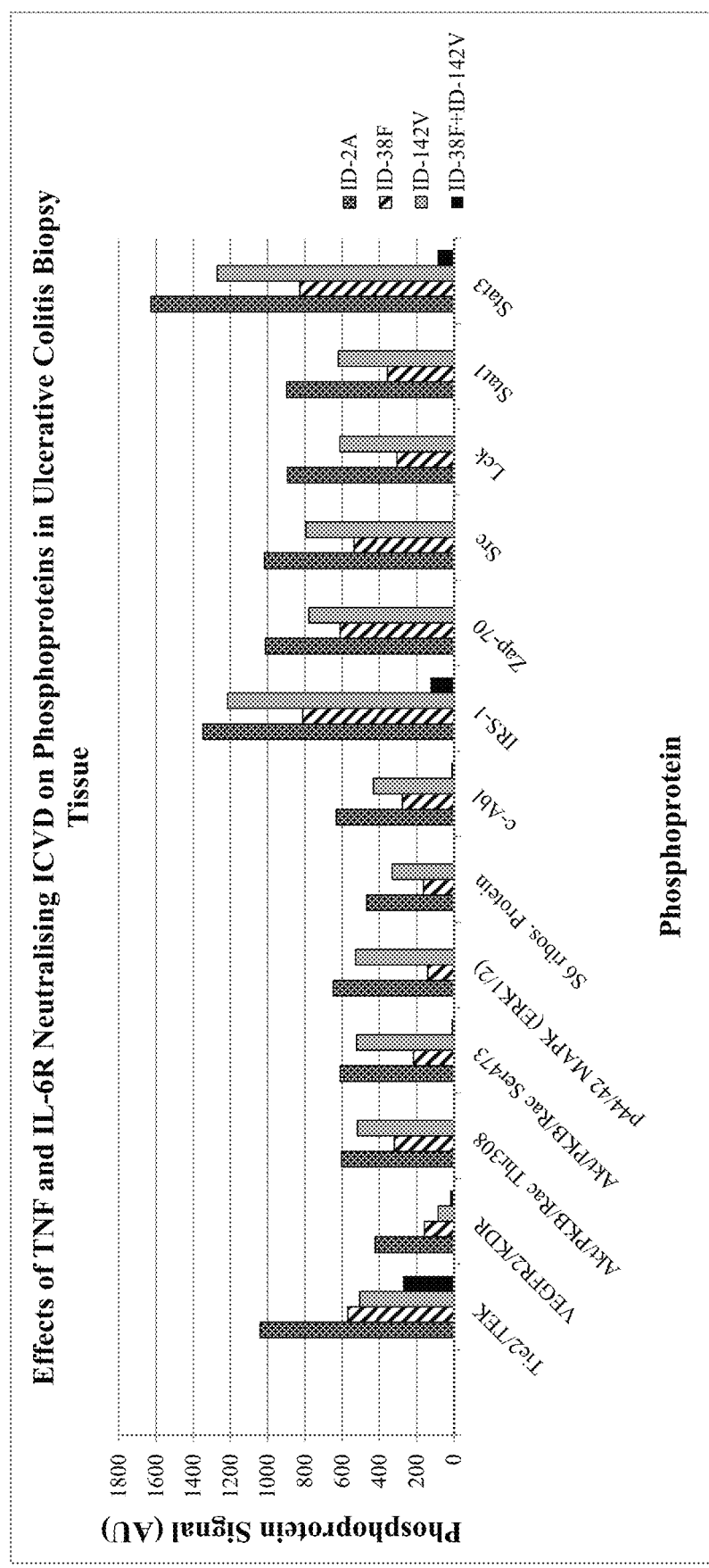

6. For comparison the treatments were repeated using inflamed biopsy tissue from two patients with ulcerative colitis. The mean+/−SD pixel intensity values obtained for each treatment (ID-2A, ID-38F, ID-142V and ID-38F+ID-142V) of n=2; UC lysates were used to calculate mean+/−SD pixel intensity values that are shown in FIG. 4

Results

Results presented in FIG. 2 show the levels of phosphorylation detected on the phospho-array for each of the TK receptor and signalling proteins. The mean pixel intensity values were calculated for each phosphoprotein on the array (data from n=4 Crohn's biopsies) and for each phosphoprotein the values obtained for each treatment have been plotted together.

Inhibition of Protein Phosphorylation in Inflamed Crohn's Disease Tissue—Treatment with a TNF-Alpha Binding Protein and an IL-6R Binding Protein Separately When compared with the ID-2A controls, the pixel intensities measured for the Crohn's biopsies treated with either ID-38F or ID-142V showed that both ICVDs inhibited the phosphorylation levels of all the signalling proteins on the array (see FIG. 2). When values for the experimental treated samples were normalised to the respective ID-2A Crohn's tissue control (FIG. 3), the average percentage inhibition (n=4 CD patients) measured for all phosphoproteins on the array following ID-38F treatment was 47% (range 30% to 100%), while the average percentage inhibition following ID-142V treatment was slightly greater 59% (range 43% to 100%). Many of these proteins including CSF-1R, Tyro-3, Axl, Akt, ZAP-70, Lck, Stat1 and Stat3 are known to have functions involved in the regulation of inflammatory cells including macrophages and T cells that contribute to the immunopathology of Crohn's disease. The changes in phosphorylation are therefore consistent with the established anti-inflammatory effects of known TNF and IL-6R-neutralising antibodies.

Inhibition of Protein Phosphorylation in Inflamed Crohn's Disease Tissue—Treatment with a TNF-Alpha Binding Protein and an IL-6R Binding Protein Simultaneously In general, the inhibitory effect of ID-38F and ID-142V combined exceeded that achieved by treatment with each ICVD individually.

Inhibition of Protein Phosphorylation in Inflamed Ulcerative Colitis Tissue—Treatment with a TNF-Alpha Binding Protein and an IL-6R Binding Protein Separately The pixel intensity values for individual phosphoproteins and the pattern of intensities on the arrays found in the control ID-2A-treated UC biopsy tissue samples (average values for n=2 UC patients) were generally quite similar to those detected in the Crohn's tissue (FIG. 4). However, the levels of phosphorylation of EphB4, Tyro3, Axl and VEGFR2 appeared to be higher while phosphorylation of Ret was lower in UC compared with CD tissue.

Treatment of UC tissue for 24 h with ID-38F inhibited the phosphorylation of most of the proteins detected on the array, with a pattern broadly similar to that seen in Crohn's tissue. Interestingly, the inhibition by either ID-38F or ID-142V of a set of phosphoproteins that included VEGFR2/KDR, Akt/PKB/Rac Thr308, Akt/PKB/Rac Ser473, p44/42 MAPK (ERK1/2), S6 ribosomal protein, c-Abl, IRS-1, Zap-70, Src, Lck, Stat1 and Stat3 was relatively weak.

Inhibition of Protein Phosphorylation in Inflamed Ulcerative Colitis Tissue—Treatment with a TNF-Alpha Binding Protein and an IL-6R Binding Protein Simultaneously When the treatments were combined, phosphorylation levels of most of these proteins were suppressed close to baseline.

In summary, treatment with an anti-TNF-alpha binding polypeptide and an anti-IL-6R binding polypeptide together was surprisingly more effective than treatment with each binding polypeptide alone.

Example 11: Investigation of the Inhibitory Effects of a TNF-Alpha Binding Polypeptide and an IL-6R Binding Polypeptide, Administered Separately and in Combination, on the Production of Cytokines in Ex Vivo Cultures of IBD Tissue TNF-Alpha and IL-6 are Important for the Activation of Inflammatory Processes that Contribute to the pathology and chronicity of IBD. Many of these effects rely on the regulation of complex cytokine networks that in turn control the different cellular processes involved in inflammation and immune-regulation. In this experiment it was investigated whether the TNFalpha- and/or IL-6R-neutralising activities of ID-38F and ID-142V, alone and in combination, can inhibit the production of cytokines that are thought to be important for the development of inflammation in IBD.

IBD Tissue

Endoscopic colonic mucosal biopsies were obtained from patients with active Inflammatory Bowel Disease (IBD). Patient characteristics are listed in Table 11.

TABLE 11

Details of IBD Patients, Disease Presentation and Medication

| Date | Patient # | Presentation/Biopsy | Medication | M/F |
|---|---|---|---|---|
| | CD2241 | /colon | Azathioprine | M; 1976 |
| | CD2244 | /colon | Azathioprine, Budesonide | M; 1982 |
| | CD2250 | /colon | No meds; (on Humira 1 year ago) | M; 1992 |
| | CD2254 | /ileum | Azathioprine, prednisolone | F; 1958 |
| | CD2256 | /terminal ileum | No meds | M; 1985 |
| | CD2259 | /colon | Azathioprine | M; 1975 |

Organ Culture

Mucosal biopsies (four biopsies per patient) were taken from six patients with active Crohn's disease. The inflamed mucosa biopsies were cultured (one biopsy per well) in 24-well plates (VWR International, Lutterworth, UK) in 300 µl serum-free HL-1 medium (Cambrex BioScience, Wokingham, UK) supplemented with glutamine, 100 µg/ml penicillin, 100 µg/ml streptomycin, 50 ug/mL gentamicin and cultured at 37° C., 5% $CO_2$. The set of biopsies (×4) from each patient were cultured for 24 h with the addition of the following antibodies; ID-38F or ID-142V each at a final concentration of 250 nM, ID-38F plus ID-142V each at a concentration of 250 nM and ID-2A (irrelevant control ICVD) at a concentration of 500 nM. Details of the ICVDs are summarised in Table 12. Supernatants and tissue samples collected at the end of the experiment were snap-frozen and stored at −70° C.

TABLE 12

Details of Antibodies and Treatment Groups

| Well | Time | Antibody | Activity | Assay |
|---|---|---|---|---|
| 1 | 24 h | ID-2A | Unrelated ICVD | Negative Control |
| 2 | 24 h | ID-38F | Anti-TNF ICVD | Mono-specific |
| 3 | 24 h | ID-142V | Anti-IL-6R ICVD | Mono-specific |
| 4 | 24 h | ID-38F + ID-142V | Anti-TNF + Anti-IL-6R ICVDs | Combined Specificity |

Multiplexed Cytokine Assays

The 24 h culture supernatants recovered from each of the four ICVD-treated biopsies (ID-2A, ID-38F, ID-142V and ID-38F+ID-142V) were analysed for each of the six CD patients. The frozen culture supernatants were thawed and analysed for levels of IFN-gamma, TNF-alpha, IL-10, IL-17A, IL-1-beta, IL-6 and IL-8 using multiplexed cytokine assay kits and R&D Systems MagPix technology.

1. Samples were diluted 1:2 in reagent diluent.
2. Standards (custom mix by R&D Systems) were re-suspended and 1:3 serial dilutions were prepared.
3. The pre-mixed micro-particle cocktail (custom mix by R&D) was prepared with reagent diluent.
4. Additions were made of 50 ul/well of standards and samples; both in duplicates, plus 50 ul of micro-particle cocktail/well.
5. The plate was sealed and incubated for 2 h at RT on a shaker
6. The plate was then attached to a magnet and washed using a multichannel pipette 3× with wash buffer.
7. 50 ul of biotin Ab cocktail (custom mix by R&D) was added per well. The plate was resealed and incubated on a shaker for 1 h at RT.
8. The wash step was repeated wash 3× using the magnet.
9. 50 ul of Streptavidin-PE mix was added/well and the plate incubated for a further 30 min at RT on a shaker.
10. After washing 3x, the microparticles were resuspended by adding 100 ul wash buffer/well, followed by incubation on a shaker for 2 minutes.
11. The plate was read using a Luminex analyser. The MagPix machine used was calibrated with R&D's calibration kit before each run.

Assay data obtained for cytokine standards were used to generate standard curves; cytokine concentrations present in the culture supernatants were then calculated from the respective standard curves.

Data Analysis

The 24 h culture supernatants recovered from the set of four ICVD-treated biopsies (ID-2A, ID-38F, ID-142V and ID-38F+ID-142V) were analysed for each of the six CD patients. The cytokine concentrations were determined and the mean values (Mean+/−Standard Deviation) were calculated using the results obtained from the set of six donors. Results are summarised in FIG. 5.

Figure 6:
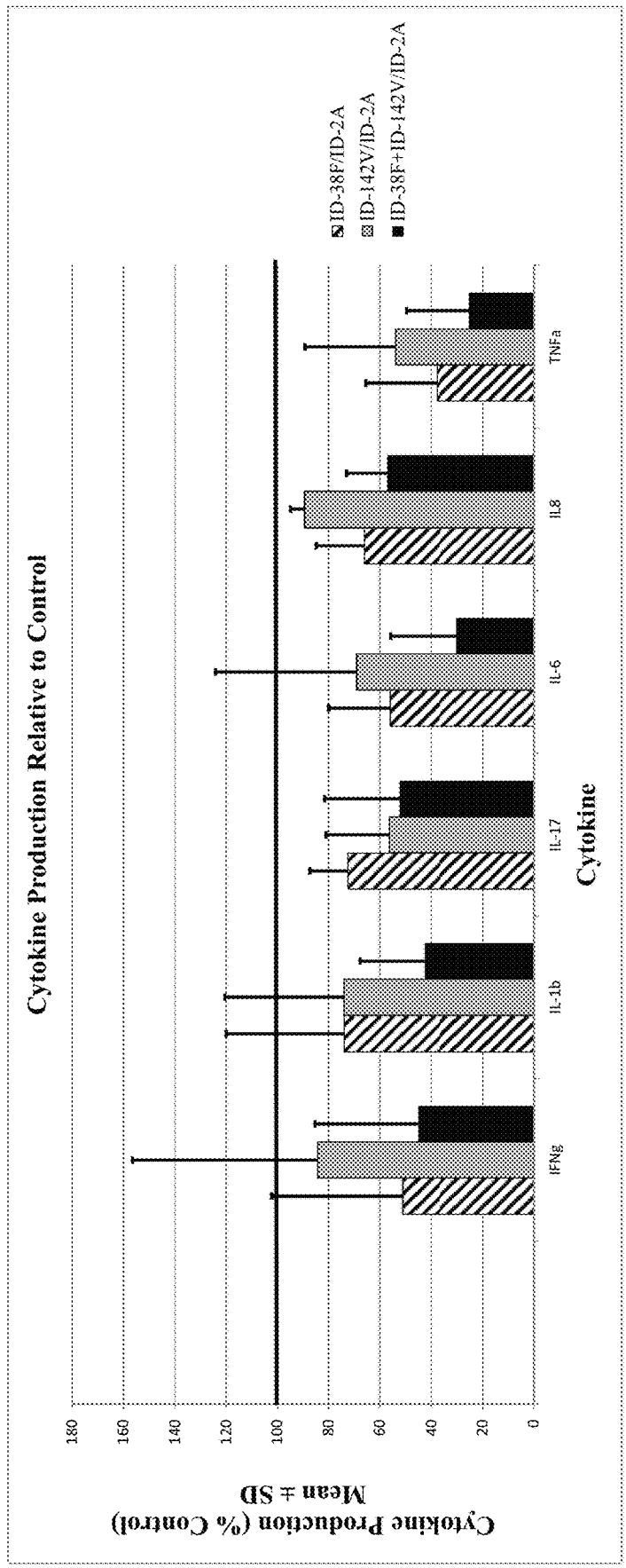
FIG. 6—Effects of TNF-alpha and IL-6R neutralising ICVDs, alone and in combination, on Crohn's biopsy tissue cytokine production, relative to control (cytokine production (% control))

Differences in the levels of inflammation and/or cellular involvement in biopsies taken from different patients could potentially result in different levels of spontaneous cytokine production between patients. To allow treatment effects to be more clearly identified the cytokine concentration value obtained for each experimental treatment was normalised to the value obtained for the corresponding patient ID-2A treatment control. The normalised % control values obtained for each cytokine (IFN-gamma, TNF-alpha, IL-10, IL-17A, IL-1-beta, IL-6 and IL-8) measured for each patient were then combined and the mean values (Mean+/−SD; n=6 CD patients) calculated. Normalised (% control) cytokine values obtained for the different treatments (ID-38F/ID-2A; ID-142V/ID-2A; Combined ID-38F+ID-142V/ID-2A) are presented in FIG. 6.

Results

Figure 5:
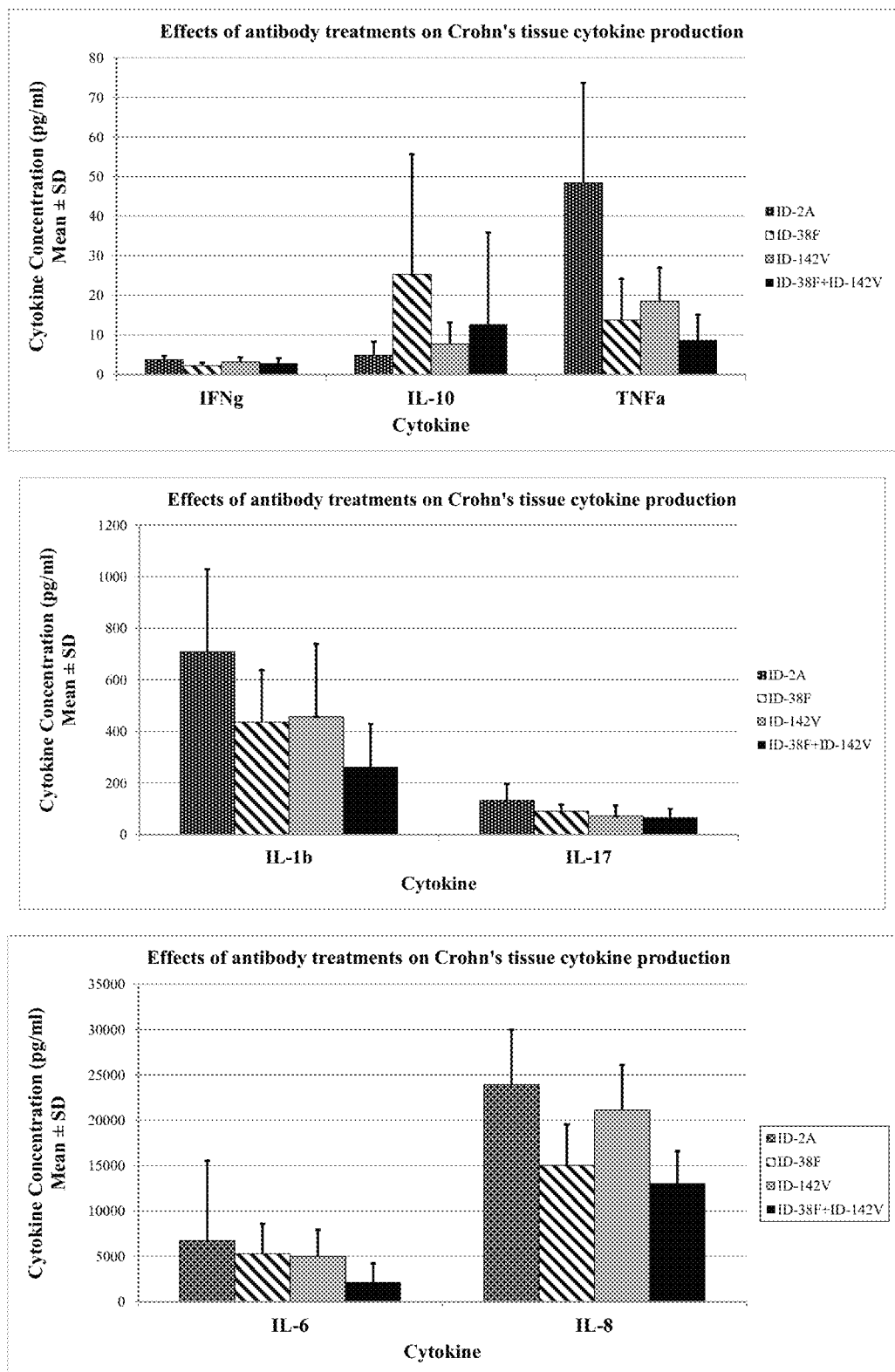
FIG. 5—Effects of TNF-alpha and IL-6R neutralising ICVDs, alone and in combination, on Crohn's biopsy tissue cytokine production (cytokine concentration (pg/ml))

The levels of spontaneous production of six different pro-inflammatory cytokines (IFN-gamma, TNF-alpha, IL-17A, IL-1-beta, IL-6 and IL-8), and of IL-10 (which has anti-inflammatory activities), are presented in FIG. 5.

When compared with the production levels of cytokines measured for the control ID-2A treated tissue, both ID-38F- and ID-142V-treatments resulted in some inhibition of each of the six pro-inflammatory cytokines. The spontaneous production of IL-1-beta, IL-17 and TNF-alpha were inhibited by ID-38F and ID-142V most strongly. The control-normalised cytokine data presented in FIG. 6 also show that both ID-38F- and ID-142V-treatments were inhibitory.

When ID-38F and ID-142V treatments were combined, the spontaneous production of each of the inflammatory cytokines IFN-gamma, TNF-alpha, IL-17A, IL-1-beta, IL-6 and IL-8 was inhibited to a greater extent than that achieved with either ICVD individually.

In contrast to the inhibitory effects of these ICVDs on production of the pro-inflammatory cytokines, treatment with ID-38F, ID-142V or the combination increased production of the anti-inflammatory cytokine IL-10 relative to the control (ID-2A).

In summary, treatment with an anti-TNF-alpha binding polypeptide and an anti-IL-6R binding polypeptide together was surprisingly more effective than treatment with each binding polypeptide alone.

Example 12: Production and Cleavage of a Heterobihead Construct Comprising ID-38F and ID-142V Linked by a Labile Linker and a Heterobihead Construct Comprising ID-38F and ID-142V Linked by a Non-Labile Linker This experiment demonstrates the liberation by trypsin of ID-38F and ID-142V from a heterobihead construct in which these ICVDs are linked by a labile peptide linker and also the stability to trypsin of a heterobihead construct comprising ID-38F and ID-142V ICVDs linked by a non-labile peptide linker.

Heterobihead constructs comprising ID-38F and ID-142V, linked by either labile or non-labile peptide linkers, were expressed in *S. cerevisiae*. ID-9K and ID-10K in this example were designed for secretion using the invertase (SUC2) signal sequence, whereas ID-11K was fused to the yeast mating factor alpha leader sequence at the N-terminus. These constructs were of the following formats, shown in Table 13:

TABLE 13

| Construct | Target(s) | Monomers | Linker |
|---|---|---|---|
| ID-9K (residues 87-335 of SEQ ID NO: 19) | TNF-alpha/ IL-6R | ID-38F/ ID-142V | GGGGSKGGGGS (SEQ ID NO: 32) |
| ID-10K (residues 87-335 of SEQ ID NO: 20) | IL-6R/ TNF-alpha | ID-142V/ ID-38F | GGGGSKGGGGS (SEQ ID NO: 32) |

TABLE 13-continued

| Construct | Target(s) | Monomers | Linker |
|---|---|---|---|
| ID-11K (residues 87-354 of SEQ ID NO: 21) | TNF-alpha/ IL-6R | ID-38F/ ID-142V | GGGGSGGGGS GGGGSGGGGS GGGGSGGGGS (SEQ ID NO: 33) |

Residues 1-86 of these sequences are the export signal sequence. Residues 87-335 of SEQ ID NO: 19 and residues 87-335 SEQ ID NO: 20 are the ID-9K and ID-10K polypeptide constructs, respectively. Residues 87-354 of SEQ ID NO: 21 is the ID-11K polypeptide construct.

ID9K and ID10K were cloned into the SacI/BsteII sites of episomal expression vector pYQVQ07, which employs a similar technology to that described for plasmids pUR4547 (as described in EP 1002861 A1) and pSY1 (Harmsen et al., 1993). pYQVQ07 is a shuttle vector, capable of replication in E. coli and S. cerevisiae for episomal expression. ID11K was cloned into the SacI/HindIII sites of integration vector pUR9013. pUR9013 encodes S. cerevisiae DNA that facilitates high copy number integration into the chromosomal rDNA locus, following linearization of the plasmid, via a similar mechanism to that described by Lopes et al. 1989. Cloning into both vectors introduces a galactose-inducible promoter upstream of the expression cassette. Expression, and full secretion into the supernatant, from S. cerevisiae was achieved via galactose induction. Finally, ID9K and ID10K constructs were purified using Protein A affinity resin (GE) and ID11K was purified using Capto S cation exchange resin (GE) and dialysed into 1×PBS.

Figure 7:
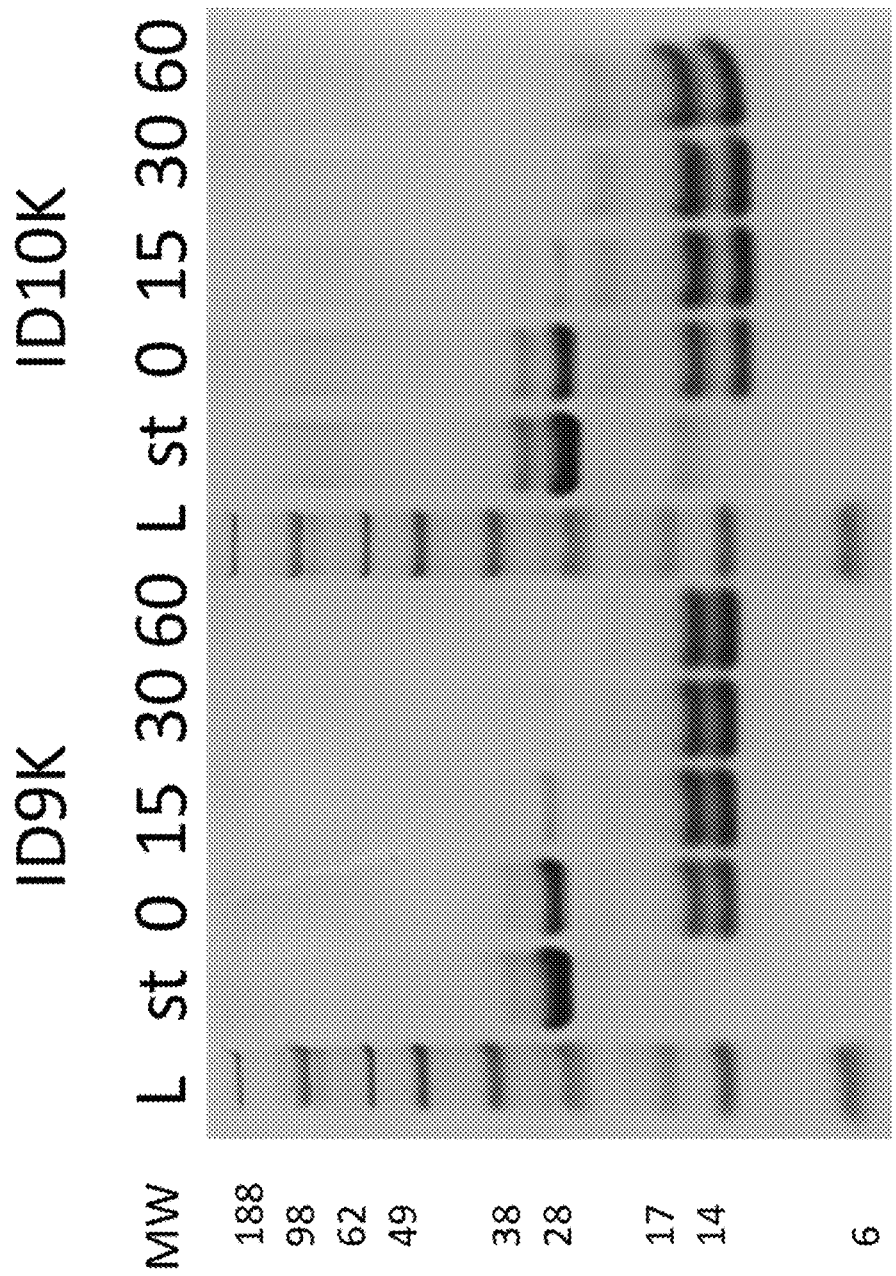
FIG. 7—Polyacrylamide gel image demonstrating liberation of ID-38F and ID-142V from heterobihead constructs comprising a labile linker FIG. 8—Polyacrylamide gel image demonstrating stability of non-labile linker used in heterobihead construct ID-11K
Figure 8:
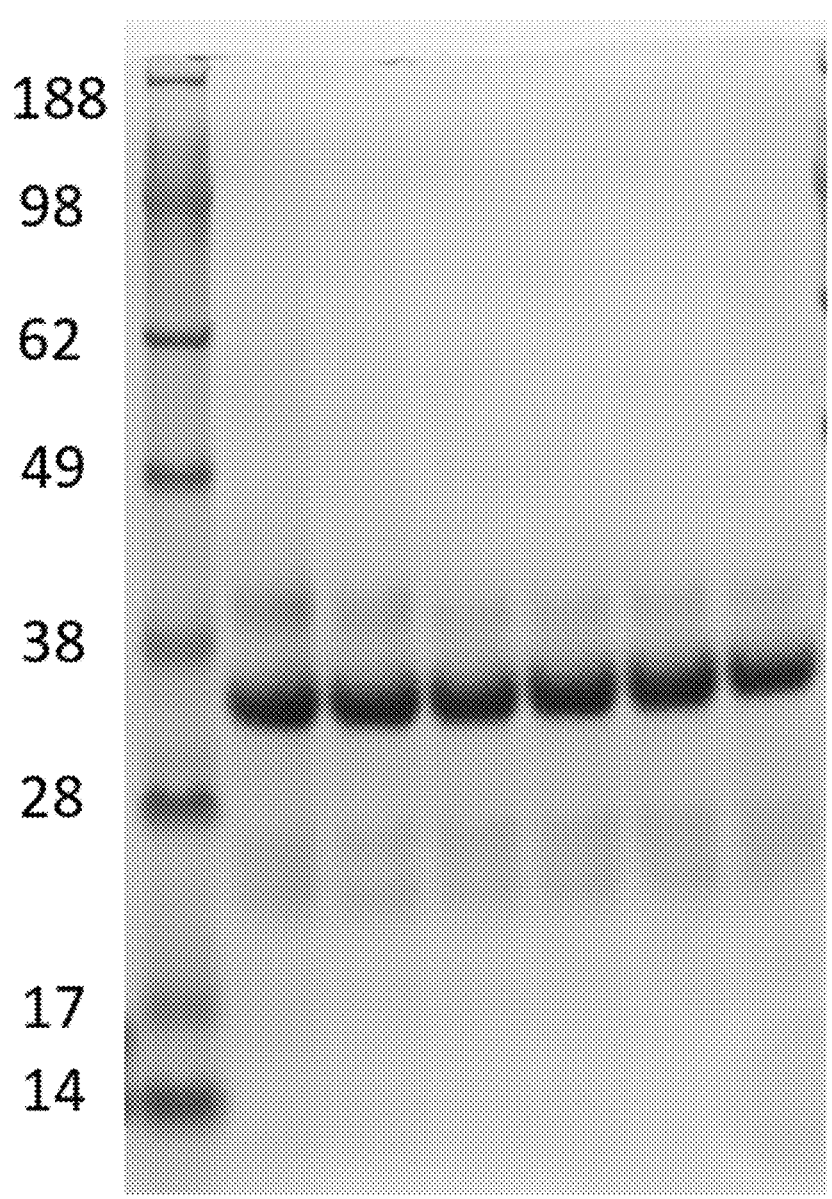

To test the lability of the peptide linkers, these constructs were incubated in the presence of trypsin-agarose beads (Sigma, T4019). After time intervals of 0, 15, 30, 45 (ID-11K only) and 60 minutes of incubation at 37° C. in a convection water bath, samples were taken. Equal volumes from each timepoint were analysed on a denaturing SDS-polyacrylamide gel. The gels were then stained with coomassie, destained and imaged by ImageQuant (GE). The quantity of intact constructs relative to cleaved constituent polypeptides can be assessed by comparing the corresponding bands in each time point lane. Images of the gels are shown in FIGS. 7 and 8, wherein st indicates a non-treated bihead standard (no exposure to trypsin beads), MW indicates molecular weight (kDa) and lanes correspond to 0, 15, 30, 45 and 60 minutes' incubation at 37° C. with trypsin beads. Time zero samples were kept on ice prior to sampling.

It can be seen from FIG. 7 that both ID-9K and ID-10K (molecular weights of around 28 kDa) had successfully liberated almost all of their constituent ICVD monomers (each having molecular weights of around 14 kDa) after 30 minutes of incubation with trypsin. ID-11K by contrast is fully stable to trypsin digestion over a 1 hour time period (FIG. 8).

Miscellaneous

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

REFERENCES

Achstetter et al 1992 Gene 110(1):25-31
Arbabi-Ghahroudi et al FEBS Lett 1997 414:521-526
Blattler et al Biochemistry 1985 24:1517-1524
Biancheri et al Gastroenterology 2015 November; 149(6): 1564-1574
Binz et al. Journal of Molecular Biology 2003 332(2):489-503
Coppieters et al 2006 Arthritis & Rheumatism 54(6):1856-1866
Chomezynnski et al Anal Biochem 1987 162:156-159
Desmet et al 2014 Nature Communications 5:5237
Ebersbach et al. J. Mol. Biol. 372 (1): 172-185
Faisst et al J Virol 1995 69:4538-4543
Frenken et al J Biotech 2000 78:11-21
Goldberg et al 2016 Protein Eng Des Sel. 29(12):563-572
Green and Sambrook Molecular Cloning: A Laboratory Manual 2012 4$^{th}$ Edition Cold Spring Harbour Laboratory Press
Grabulovski 2007 J Biol Chem. 282(5):3196-3204
Griffiths et al Antibodies 2013 2:66-81
Grundstrom et al 1985 Nucl. Acids Res 13:3305-3316
Gustot et al Gut 2005; 54(4):488-95
Hamers-Casterman et al Nature 1993 363(6428):446-448
Harmsen et al Gene 1993 125:115-123
Harmsen et al Appl Microbiol Biotechnol 2007 77(1):13-22)
Hendrickson et al Clin Microbiol Rev 2002 15(1):79-94
Hoogenboom et al Nucl Acid Res 1991 19:4133-4137
Hosokawa et al J Gastroenterol Hepatol. 1999; 14(10):987-96
Humphreys and Wilson 1999 Cytokine 11(10):773-782
Huse et al Science 1989 246 (4935):1275-1281
Ito et al Gastroenterology 2004; 126(4):989-96
Johnson et al 2012 Anal. Chem. 84(15):6553-6560
Kabat et al Sequences of Proteins of Immunological Interest, Fifth Edition U.S. Department of Health and Human Services, 1991 NIH Publication Number 91-3242
Knezevic et al J. Am. Chem. Soc. 2012, 134(37):15225-15228
Köhler et al Nature 1975 256:495-497
Koide and Koide 2007 Methods Mol. Biol. 352: 95-109
Krehenbrink et al 2008 J. Mol. Biol. 383 (5):1058-1068.
Kusugami et al Dig Dis Sci. 1995; 40(5):949-59
Ling et al Anal Biochem 1997 254(2):157-178
Lipovsek 2011 Protein Eng Des Sel. 24(1-2):3-9
Lopes et al. 1989 Gene, 79. 199-206
McCoy et al Retrovirology 2014 11:83
Merchlinsky et al J. Virol. 1983 47:227-232
Miethe et al J Biotech 2013 163(2):105-111
Mitsuyama et al Anticancer Res. 2007; 27(6A):3749-56
Muyldermans et al Protein Eng 1994 7(9):1129-1135
Muyldermans Annu Rev Biochem 2013 82:775-797
Nambiar et al Science 1984 223:1299-1301
Nelson et al Molecular Pathology 2000 53(3):111-117
Nguyen et al Adv Immunol 2001 79:261-296
Nixon and Wood 2006 Curr Opin Drug Discov Devel. 9(2):261-268

Nygren *FEBS J.* 2008 275(11):2668-76
Ortonne, *Brit J Dermatol* 1999 140 (suppl 54):1-7
Padlan *Mol Immunol* 1994 31:169-217
Reimund et al *J Clin Immunol.* 1996; 16(3):144-50
Reinecker et al *Clin Exp Immunol.* 1993; 94(1):174-81
Romanos et al 1992 Yeast 8:423-488
Rose-John *Int J Biol Sci.* 2012; 8(9):1237-47
Roux et al *Proc Natl Acad Sci USA* 1998 95:11804-11809
Sakamar et al *Nucl. Acids Res* 1988 14:6361-6372
Silverman et al 2005 *Nat. Biotechnol.* 23(12):1556-1561
Skerra et al *Science* 1988 240(4855):1038-1041
Skerra et al 2008 *FEBS J.* 275 (11): 2677-83
Suderman 2017 *Protein Expression and Purification* 134: 114-124
Tanha et al *J Immunol Methods* 2002 263:97-109
Thomassen et al *Enzyme and Micro Tech* 2002 30:273-278
Ungar et al. 2016 *Clin Gastroenterol Hepatol.* 14(4):550-557
Vandenbroucke et al *Mucosal Immunology* 2010 3(1):49-56
Verma et al *Annu Rev Biochem* 1998 67:99-134
Waetzig & Rose-John *Expert Opin Ther Targets* 2012; 16(2):225-36
Ward et al *Nature* 1989 341:544-546
Wells et al *Gene* 1985 34:315-323

The invention claimed is:

1. A composition comprising:
   (a) an TNF-alpha-binding VHH, said TNF-alpha-binding VHH comprising three complementarity determining regions (CDR1-CDR3), wherein CDR1 comprises SEQ ID NO: 1, CDR2 comprises SEQ ID NO: 2 and CDR3 comprises SEQ ID NO: 3; and
   (b) an IL-6R-binding VHH, said IL-6R-binding VHH comprising three complementarity determining regions (CDR1-CDR3), wherein CDR1 comprises SEQ ID NO: 9, CDR2 comprises SEQ ID NO: 10 and CDR3 comprises SEQ ID NO: 11.

2. The composition according to claim 1, wherein said TNF-alpha-binding VHH binds to TNF-alpha with a Kd of 10-7 M or less, and said IL-6R-binding VHH binds to IL-6R with a Kd of $10^{-7}$ M or less.

3. The composition according to claim 2, wherein said TNF-alpha-binding VHH neutralizes human TNF-alpha cytotoxicity in an L929 assay with an EC50 of 1 nM or less, and said antibody or said IL-6R-binding VHH neutralizes IL-6R in a standard gp130 ELISA assay with an EC50 of 1 nM or less.

4. The composition according to claim 1, wherein TNF-alpha-binding VHH neutralizes human TNF-alpha cytotoxicity in an L929 assay with an EC50 of 1 nM or less, and said IL-6R-binding VHH neutralizes IL-6R in a standard gp130 ELISA assay with an EC50 of 1 nM or less.

5. The composition according to claim 1, wherein said TNF-alpha-binding VHH and said IL-6R-binding VHH are linked.

6. The composition according to claim 5, wherein said TNF-alpha-binding VHH and said IL-6R-binding VHH are linked by a protease-labile peptide linker.

7. The composition according to claim 1, wherein said composition retains binding to TNF-alpha and IL-6R after 16 hours incubation in a human faecal supernatant.

8. The composition according to claim 1 wherein the composition is suitable for oral administration.

9. The composition according to claim 1, wherein the composition comprises an enteric coating.

10. A pharmaceutical composition comprising the composition according to claim 1 and a pharmaceutically acceptable excipient.

11. A method of treating an autoimmune disease and/or an inflammatory disease comprising administering to a person in need thereof a therapeutically effective amount of the composition according to claim 1.

12. The method according to claim 11, wherein the autoimmune disease and/or inflammatory disease is inflammatory bowel disease and/or mucositis.

13. The method according to claim 12, wherein the inflammatory bowel disease is ulcerative colitis or Crohn's disease.

14. The method according to claim 11, wherein the composition is administered orally.

* * * * *